US012630643B2

(12) United States Patent　　(10) Patent No.:　US 12,630,643 B2
Mangsbo et al.　　　　　　　　(45) Date of Patent:　May 19, 2026

(54) CD40 BINDING PROTEIN, BISPECIFIC CONJUGATE THEREOF AND METHOD OF TREATING CANCER

(71) Applicant: STRIKE PHARMA AB, Lund (SE)

(72) Inventors: Sara Mangsbo, Uppsala (SE); Helena Persson Lotsholm, Järfälla (SE); Oskar Andersson, Lidingö (SE)

(73) Assignee: STRIKE PHARMA AB, Lund (SE)

( * ) Notice: Subject to any disclaimer, the term of this patent is extended or adjusted under 35 U.S.C. 154(b) by 731 days.

(21) Appl. No.: 17/922,781

(22) PCT Filed: May 28, 2021

(86) PCT No.: PCT/EP2021/064390
§ 371 (c)(1),
(2) Date: Nov. 1, 2022

(87) PCT Pub. No.: WO2021/239968
PCT Pub. Date: Dec. 2, 2021

(65) Prior Publication Data
US 2023/0167185 A1　　Jun. 1, 2023

(30) Foreign Application Priority Data

May 28, 2020　(GB) .................................... 2008003

(51) Int. Cl.
*A61K 39/395* 　(2006.01)
*A61K 39/00* 　(2006.01)
*C07K 16/28* 　(2006.01)

(52) U.S. Cl.
CPC ...... *C07K 16/2878* (2013.01); *A61K 39/0011* (2013.01); *C07K 2317/31* (2013.01); *C07K 2317/565* (2013.01); *C07K 2317/622* (2013.01); *C07K 2317/77* (2013.01)

(58) Field of Classification Search
None
See application file for complete search history.

(56) References Cited

U.S. PATENT DOCUMENTS

2022/0175920 A1 *　6/2022　Levy ................. C07K 16/2878

FOREIGN PATENT DOCUMENTS

CN　　　104918957 A　　9/2015
WO　WO 03/040170 A2　　5/2003
WO　WO 2017/184619 A2　10/2017
(Continued)

OTHER PUBLICATIONS

Wu et al., Building blocks for bispecific and trispecific antibodies, Methods, 154:3-9, 7 pages, 2019.*
(Continued)

*Primary Examiner* — Claire Kaufman
(74) *Attorney, Agent, or Firm* — James S. Keddie; Bozicevic, Field & Francis LLP

(57) ABSTRACT

Provided is a binding protein that binds CD40 and is an agonist thereof. In a particular embodiment the invention provides an agonistic anti-CD40 antibody. Also provided are bispecific conjugates comprising the binding protein, and complexes comprising the bispecific conjugates non-covalently bound to a tag construct comprising an antigen, for antigen delivery to immune cells. Medical uses of the binding proteins, conjugates and complexes of the invention are also provided.

25 Claims, 16 Drawing Sheets
Specification includes a Sequence Listing.

(56) References Cited

FOREIGN PATENT DOCUMENTS

| WO | WO 2017/184619 A3 | 10/2017 | |
| WO | WO 2017/205742 A1 | 11/2017 | |
| WO | WO 2018/011421 A1 | 1/2018 | |
| WO | WO 2018/213747 A1 | 11/2018 | |
| WO | WO 2019/093342 A1 | 5/2019 | |
| WO | WO-2020104690 A1 * | 5/2020 | ............. A61K 39/12 |

OTHER PUBLICATIONS

Andersson et al., Next-generation CD40 agonists for cancer immunotherapy, Expert Opin. Biol. Ther. 24(5):351-363, 2024.*

Ara et al., Multiple effects of CD40-CD40L axis in immunity against infection and cancer, , Immuno Targets Ther., 55-61, 2018.*

Bartholdy et al. , Agonistic Anti-CD40 Antibody Profoundly Suppressesthe Immune Response to Infection with Lymphocytic Choriomeningitis Virus1, J. Immunol. 178:1662-1670, 2007.*

McVey et al., Facts and Hopes of CD40 Agonists in Cancer Immunotherapy, Clin. Cancer Res; 31(11) Jun. 1, 2025.*

Mebrahtu et al., A bispecific CD40 agonistic antibody allowing for antibody-peptide conjugate formation to enable cancer-specific peptide delivery, resulting in improved T Cell Nat. Comm. 15:9542, 20 pages, 2024.*

Dahan et al., "Therapeutic Activity of Agonistic, Human Anti-CD40 Monoclonal Antibodies Requires Selective FcyR Engagement", Cancer Cell, 2016, 29: 820-831.

Gladue et al., "The CD40 agonist antibody CP-870,893 enhances dendritic cell and B-cell activity and promotes anti-tumor efficacy in SCID-hu mice", Cancer Immunol Immunother, 2011, 60: 1009-1017.

Yu et al., "Isotype Switching Converts Anti-CD40 Antagonism to Agonism to Elicit Potent Antitumor Activity", Cancer Cell, Jun. 2020, 37: 850-866.

* cited by examiner 200 nM                          1.6 nM 200 nM                                    1.6 nM

A

B

SEQUENCE LISTING

<160> NUMBER OF SEQ ID NOS: 87

<210> SEQ ID NO 1
<211> LENGTH: 6
<212> TYPE: PRT
<213> ORGANISM: Artificial Sequence
<220> FEATURE:
<223> OTHER INFORMATION: VLCDR1

<400> SEQUENCE: 1

Gln Ser Ile Ser Ser Tyr
1               5

<210> SEQ ID NO 2

<400> SEQUENCE: 2

000

<210> SEQ ID NO 3
<211> LENGTH: 9
<212> TYPE: PRT
<213> ORGANISM: Artificial Sequence
<220> FEATURE:
<223> OTHER INFORMATION: VLCDR3

<400> SEQUENCE: 3

Gln Gln Gly Tyr Pro Tyr Pro Phe Thr
1               5

<210> SEQ ID NO 4
<211> LENGTH: 8
<212> TYPE: PRT
<213> ORGANISM: Artificial Sequence
<220> FEATURE:
<223> OTHER INFORMATION: VHCDR1

<400> SEQUENCE: 4

Gly Phe Thr Phe Ser Ser Tyr Ala
1               5

<210> SEQ ID NO 5
<211> LENGTH: 8
<212> TYPE: PRT
<213> ORGANISM: Artificial Sequence
<220> FEATURE:
<223> OTHER INFORMATION: VHCDR2

<400> SEQUENCE: 5

Ile Ser Gly Tyr Ser Gly Ser Thr
1               5

<210> SEQ ID NO 6
<211> LENGTH: 14
<212> TYPE: PRT
<213> ORGANISM: Artificial Sequence
<220> FEATURE:
<223> OTHER INFORMATION: VHCDR3

<400> SEQUENCE: 6

Ala Arg Tyr Tyr Ser Tyr Tyr Gly Tyr Tyr Tyr Phe Asp Tyr
1               5                   10

<210> SEQ ID NO 7
<211> LENGTH: 107
<212> TYPE: PRT
<213> ORGANISM: Artificial Sequence

```
<220> FEATURE:
<223> OTHER INFORMATION: Light chain variable domain

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Pro Tyr Pro Phe
                85                  90                  95

Thr Phe Gly Gln Gly Thr Lys Leu Glu Ile Lys
            100                 105

<210> SEQ ID NO 8
<211> LENGTH: 121
<212> TYPE: PRT
<213> ORGANISM: Artificial Sequence
<220> FEATURE:
<223> OTHER INFORMATION: Heavy chain variable domain

<400> SEQUENCE: 8

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Ser Gly Tyr Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Ser Tyr Tyr Gly Tyr Tyr Tyr Phe Asp Tyr Trp Gly
            100                 105                 110

Gln Gly Thr Leu Val Thr Val Ser Ser
        115                 120

<210> SEQ ID NO 9
<211> LENGTH: 214
<212> TYPE: PRT
<213> ORGANISM: Artificial Sequence
<220> FEATURE:
<223> OTHER INFORMATION: Light chain

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45
```

-continued

```
Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Pro Tyr Pro Phe
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210
```

```
<210> SEQ ID NO 10
<211> LENGTH: 447
<212> TYPE: PRT
<213> ORGANISM: Artificial Sequence
<220> FEATURE:
<223> OTHER INFORMATION: Heavy chain

<400> SEQUENCE: 10
```

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Gly Ile Ser Gly Tyr Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Ser Tyr Tyr Gly Tyr Tyr Tyr Phe Asp Tyr Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
            180                 185                 190
```

```
Pro Ser Ser Asn Phe Gly Thr Gln Thr Tyr Thr Cys Asn Val Asp His
        195                 200             205

Lys Pro Ser Asn Thr Lys Val Asp Lys Thr Val Glu Arg Lys Cys Cys
        210             215             220

Val Glu Cys Pro Pro Cys Pro Ala Pro Pro Val Ala Gly Pro Ser Val
225                 230             235                 240

Phe Leu Phe Pro Pro Lys Pro Lys Asp Thr Leu Met Ile Ser Arg Thr
                245             250             255

Pro Glu Val Thr Cys Val Val Val Asp Val Ser His Glu Asp Pro Glu
            260             265             270

Val Gln Phe Asn Trp Tyr Val Asp Gly Val Glu Val His Asn Ala Lys
        275             280             285

Thr Lys Pro Arg Glu Glu Gln Phe Asn Ser Thr Phe Arg Val Val Ser
        290             295             300

Val Leu Thr Val Val His Gln Asp Trp Leu Asn Gly Lys Glu Tyr Lys
305             310             315             320

Cys Lys Val Ser Asn Lys Gly Leu Pro Ala Pro Ile Glu Lys Thr Ile
            325             330             335

Ser Lys Thr Lys Gly Gln Pro Arg Glu Pro Gln Val Tyr Thr Leu Pro
            340             345             350

Pro Ser Arg Glu Glu Met Thr Lys Asn Gln Val Ser Leu Thr Cys Leu
        355             360             365

Val Lys Gly Phe Tyr Pro Ser Asp Ile Ala Val Glu Trp Glu Ser Asn
        370             375             380

Gly Gln Pro Glu Asn Asn Tyr Lys Thr Thr Pro Pro Met Leu Asp Ser
385             390             395             400

Asp Gly Ser Phe Phe Leu Tyr Ser Lys Leu Thr Val Asp Lys Ser Arg
                405             410             415

Trp Gln Gln Gly Asn Val Phe Ser Cys Ser Val Met His Glu Ala Leu
            420             425             430

His Asn His Tyr Thr Gln Lys Ser Leu Ser Leu Ser Pro Gly Lys
            435             440             445

<210> SEQ ID NO 11
<211> LENGTH: 22
<212> TYPE: PRT
<213> ORGANISM: Clostridium tetani
<220> FEATURE:
<223> OTHER INFORMATION: Peptide

<400> SEQUENCE: 11

Gly Ile Leu Phe Leu Gln Trp Val Arg Asp Ile Ile Asp Asp Phe Thr
1               5               10              15

Asn Glu Ser Ser Gln Lys
            20

<210> SEQ ID NO 12
<211> LENGTH: 21
<212> TYPE: PRT
<213> ORGANISM: Clostridium tetani
<220> FEATURE:
<223> OTHER INFORMATION: Peptide

<400> SEQUENCE: 12

Asp Ser Asp Lys Asp Arg Phe Leu Gln Thr Met Val Lys Leu Phe Asn
1               5               10              15

Arg Ile Lys Asn Asn
            20
```

```
<210> SEQ ID NO 13
<211> LENGTH: 25
<212> TYPE: PRT
<213> ORGANISM: Clostridium tetani
<220> FEATURE:
<223> OTHER INFORMATION: Peptide

<400> SEQUENCE: 13

Ile Asp Ile Lys Asn Asp Leu Tyr Glu Lys Thr Leu Asn Asp Tyr Lys
1               5                   10                  15

Ala Ile Ala Asn Lys Leu Ser Gln Val
            20                  25

<210> SEQ ID NO 14
<211> LENGTH: 21
<212> TYPE: PRT
<213> ORGANISM: Clostridium tetani
<220> FEATURE:
<223> OTHER INFORMATION: Peptide

<400> SEQUENCE: 14

Gln Asp Pro Ala Leu Leu Leu Met His Glu Leu Ile His Val Leu His
1               5                   10                  15

Gly Leu Tyr Gly Met
            20

<210> SEQ ID NO 15
<211> LENGTH: 24
<212> TYPE: PRT
<213> ORGANISM: Clostridium tetani
<220> FEATURE:
<223> OTHER INFORMATION: Peptide

<400> SEQUENCE: 15

Asp Gly Ile Leu Phe Leu Gln Trp Val Arg Asp Ile Ile Asp Asp Phe
1               5                   10                  15

Thr Asn Glu Ser Ser Gln Lys Arg
            20

<210> SEQ ID NO 16
<211> LENGTH: 12
<212> TYPE: PRT
<213> ORGANISM: Artificial Sequence
<220> FEATURE:
<223> OTHER INFORMATION: Peptide

<400> SEQUENCE: 16

Phe Ile Gly Ile Thr Glu Leu Lys Lys Leu Glu Ser
1               5                   10

<210> SEQ ID NO 17
<211> LENGTH: 277
<212> TYPE: PRT
<213> ORGANISM: Homo sapiens
<220> FEATURE:
<223> OTHER INFORMATION: CD40

<400> SEQUENCE: 17

Met Val Arg Leu Pro Leu Gln Cys Val Leu Trp Gly Cys Leu Leu Thr
1               5                   10                  15

Ala Val His Pro Glu Pro Pro Thr Ala Cys Arg Glu Lys Gln Tyr Leu
            20                  25                  30

Ile Asn Ser Gln Cys Cys Ser Leu Cys Gln Pro Gly Gln Lys Leu Val
```

```
          35                    40                    45

Ser Asp Cys Thr Glu Phe Thr Glu Thr Glu Cys Leu Pro Cys Gly Glu
    50                    55                    60

Ser Glu Phe Leu Asp Thr Trp Asn Arg Glu Thr His Cys His Gln His
65                    70                    75                    80

Lys Tyr Cys Asp Pro Asn Leu Gly Leu Arg Val Gln Gln Lys Gly Thr
                85                    90                    95

Ser Glu Thr Asp Thr Ile Cys Thr Cys Glu Glu Gly Trp His Cys Thr
                100                   105                   110

Ser Glu Ala Cys Glu Ser Cys Val Leu His Arg Ser Cys Ser Pro Gly
                115                   120                   125

Phe Gly Val Lys Gln Ile Ala Thr Gly Val Ser Asp Thr Ile Cys Glu
    130                   135                   140

Pro Cys Pro Val Gly Phe Phe Ser Asn Val Ser Ser Ala Phe Glu Lys
145                   150                   155                   160

Cys His Pro Trp Thr Ser Cys Glu Thr Lys Asp Leu Val Val Gln Gln
                165                   170                   175

Ala Gly Thr Asn Lys Thr Asp Val Val Cys Gly Pro Gln Asp Arg Leu
                180                   185                   190

Arg Ala Leu Val Val Ile Pro Ile Ile Phe Gly Ile Leu Phe Ala Ile
                195                   200                   205

Leu Leu Val Leu Val Phe Ile Lys Lys Val Ala Lys Lys Pro Thr Asn
    210                   215                   220

Lys Ala Pro His Pro Lys Gln Glu Pro Gln Glu Ile Asn Phe Pro Asp
225                   230                   235                   240

Asp Leu Pro Gly Ser Asn Thr Ala Ala Pro Val Gln Glu Thr Leu His
                245                   250                   255

Gly Cys Gln Pro Val Thr Gln Glu Asp Gly Lys Glu Ser Arg Ile Ser
                260                   265                   270

Val Gln Glu Arg Gln
        275
```

```
<210> SEQ ID NO 18
<211> LENGTH: 326
<212> TYPE: PRT
<213> ORGANISM: Homo sapiens
<220> FEATURE:
<223> OTHER INFORMATION: IgG2 constant region

<400> SEQUENCE: 18

Ala Ser Thr Lys Gly Pro Ser Val Phe Pro Leu Ala Pro Cys Ser Arg
1                 5                     10                    15

Ser Thr Ser Glu Ser Thr Ala Ala Leu Gly Cys Leu Val Lys Asp Tyr
                20                    25                    30

Phe Pro Glu Pro Val Thr Val Ser Trp Asn Ser Gly Ala Leu Thr Ser
        35                    40                    45

Gly Val His Thr Phe Pro Ala Val Leu Gln Ser Ser Gly Leu Tyr Ser
    50                    55                    60

Leu Ser Ser Val Val Thr Val Pro Ser Ser Asn Phe Gly Thr Gln Thr
65                    70                    75                    80

Tyr Thr Cys Asn Val Asp His Lys Pro Ser Asn Thr Lys Val Asp Lys
                85                    90                    95

Thr Val Glu Arg Lys Cys Cys Val Glu Cys Pro Pro Cys Pro Ala Pro
                100                   105                   110

Pro Val Ala Gly Pro Ser Val Phe Leu Phe Pro Pro Lys Pro Lys Asp
```

-continued

```
                    115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
            245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
    275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325
```

<210> SEQ ID NO 19
<211> LENGTH: 107
<212> TYPE: PRT
<213> ORGANISM: Homo sapiens
<220> FEATURE:
<223> OTHER INFORMATION: A9 light chain constant region

<400> SEQUENCE: 19

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 20
<211> LENGTH: 326
<212> TYPE: PRT
<213> ORGANISM: Artificial Sequence
<220> FEATURE:
<223> OTHER INFORMATION: IgG2 C127S constant region

<400> SEQUENCE: 20

Ala Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
                100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
            130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
            210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
            245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
            290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 21
<211> LENGTH: 5
<212> TYPE: PRT
<213> ORGANISM: Artificial Sequence
<220> FEATURE:
<223> OTHER INFORMATION: Linker

<400> SEQUENCE: 21

Gly Gly Gly Gly Ser
1               5

```
<210> SEQ ID NO 22
<211> LENGTH: 10
<212> TYPE: PRT
<213> ORGANISM: Artificial Sequence
<220> FEATURE:
<223> OTHER INFORMATION: Linker

<400> SEQUENCE: 22

Gly Gly Gly Gly Ser Gly Gly Gly Ser
1               5                   10

<210> SEQ ID NO 23
<211> LENGTH: 1315
<212> TYPE: PRT
<213> ORGANISM: Clostridium tetani
<220> FEATURE:
<223> OTHER INFORMATION: Tetanus toxin

<400> SEQUENCE: 23

Met Pro Ile Thr Ile Asn Asn Phe Arg Tyr Ser Asp Pro Val Asn Asn
1               5                   10                  15

Asp Thr Ile Ile Met Met Glu Pro Pro Tyr Cys Lys Gly Leu Asp Ile
                20                  25                  30

Tyr Tyr Lys Ala Phe Lys Ile Thr Asp Arg Ile Trp Ile Val Pro Glu
            35                  40                  45

Arg Tyr Glu Phe Gly Thr Lys Pro Glu Asp Phe Asn Pro Pro Ser Ser
        50                  55                  60

Leu Ile Glu Gly Ala Ser Glu Tyr Tyr Asp Pro Asn Tyr Leu Arg Thr
65                  70                  75                  80

Asp Ser Asp Lys Asp Arg Phe Leu Gln Thr Met Val Lys Leu Phe Asn
                85                  90                  95

Arg Ile Lys Asn Asn Val Ala Gly Glu Ala Leu Leu Asp Lys Ile Ile
                100                 105                 110

Asn Ala Ile Pro Tyr Leu Gly Asn Ser Tyr Ser Leu Leu Asp Lys Phe
            115                 120                 125

Asp Thr Asn Ser Asn Ser Val Ser Phe Asn Leu Leu Glu Gln Asp Pro
        130                 135                 140

Ser Gly Ala Thr Thr Lys Ser Ala Met Leu Thr Asn Leu Ile Ile Phe
145                 150                 155                 160

Gly Pro Gly Pro Val Leu Asn Lys Asn Glu Val Arg Gly Ile Val Leu
                165                 170                 175

Arg Val Asp Asn Lys Asn Tyr Phe Pro Cys Arg Asp Gly Phe Gly Ser
                180                 185                 190

Ile Met Gln Met Ala Phe Cys Pro Glu Tyr Val Pro Thr Phe Asp Asn
            195                 200                 205

Val Ile Glu Asn Ile Thr Ser Leu Thr Ile Gly Lys Ser Lys Tyr Phe
        210                 215                 220

Gln Asp Pro Ala Leu Leu Leu Met His Glu Leu Ile His Val Leu His
225                 230                 235                 240

Gly Leu Tyr Gly Met Gln Val Ser Ser His Glu Ile Ile Pro Ser Lys
                245                 250                 255

Gln Glu Ile Tyr Met Gln His Thr Tyr Pro Ile Ser Ala Glu Glu Leu
                260                 265                 270

Phe Thr Phe Gly Gly Gln Asp Ala Asn Leu Ile Ser Ile Asp Ile Lys
            275                 280                 285

Asn Asp Leu Tyr Glu Lys Thr Leu Asn Asp Tyr Lys Ala Ile Ala Asn
        290                 295                 300
```

```
Lys Leu Ser Gln Val Thr Ser Cys Asn Asp Pro Asn Ile Asp Ile Asp
305                 310                 315                 320

Ser Tyr Lys Gln Ile Tyr Gln Gln Lys Tyr Gln Phe Asp Lys Asp Ser
                325                 330                 335

Asn Gly Gln Tyr Ile Val Asn Glu Asp Lys Phe Gln Ile Leu Tyr Asn
                340                 345                 350

Ser Ile Met Tyr Gly Phe Thr Glu Ile Glu Leu Gly Lys Lys Phe Asn
                355                 360                 365

Ile Lys Thr Arg Leu Ser Tyr Phe Ser Met Asn His Asp Pro Val Lys
        370                 375                 380

Ile Pro Asn Leu Leu Asp Asp Thr Ile Tyr Asn Asp Thr Glu Gly Phe
385                 390                 395                 400

Asn Ile Glu Ser Lys Asp Leu Lys Ser Glu Tyr Lys Gly Gln Asn Met
                405                 410                 415

Arg Val Asn Thr Asn Ala Phe Arg Asn Val Asp Gly Ser Gly Leu Val
                420                 425                 430

Ser Lys Leu Ile Gly Leu Cys Lys Lys Ile Ile Pro Pro Thr Asn Ile
        435                 440                 445

Arg Glu Asn Leu Tyr Asn Arg Thr Ala Ser Leu Thr Asp Leu Gly Gly
        450                 455                 460

Glu Leu Cys Ile Lys Ile Lys Asn Glu Asp Leu Thr Phe Ile Ala Glu
465                 470                 475                 480

Lys Asn Ser Phe Ser Glu Glu Pro Phe Gln Asp Glu Ile Val Ser Tyr
                485                 490                 495

Asn Thr Lys Asn Lys Pro Leu Asn Phe Asn Tyr Ser Leu Asp Lys Ile
                500                 505                 510

Ile Val Asp Tyr Asn Leu Gln Ser Lys Ile Thr Leu Pro Asn Asp Arg
                515                 520                 525

Thr Thr Pro Val Thr Lys Gly Ile Pro Tyr Ala Pro Glu Tyr Lys Ser
        530                 535                 540

Asn Ala Ala Ser Thr Ile Glu Ile His Asn Ile Asp Asp Asn Thr Ile
545                 550                 555                 560

Tyr Gln Tyr Leu Tyr Ala Gln Lys Ser Pro Thr Thr Leu Gln Arg Ile
                565                 570                 575

Thr Met Thr Asn Ser Val Asp Asp Ala Leu Ile Asn Ser Thr Lys Ile
                580                 585                 590

Tyr Ser Tyr Phe Pro Ser Val Ile Ser Lys Val Asn Gln Gly Ala Gln
                595                 600                 605

Gly Ile Leu Phe Leu Gln Trp Val Arg Asp Ile Ile Asp Asp Phe Thr
        610                 615                 620

Asn Glu Ser Ser Gln Lys Thr Thr Ile Asp Lys Ile Ser Asp Val Ser
625                 630                 635                 640

Thr Ile Val Pro Tyr Ile Gly Pro Ala Leu Asn Ile Val Lys Gln Gly
                645                 650                 655

Tyr Glu Gly Asn Phe Ile Gly Ala Leu Glu Thr Thr Gly Val Val Leu
                660                 665                 670

Leu Leu Glu Tyr Ile Pro Glu Ile Thr Leu Pro Val Ile Ala Ala Leu
        675                 680                 685

Ser Ile Ala Glu Ser Ser Thr Gln Lys Glu Lys Ile Ile Lys Thr Ile
        690                 695                 700

Asp Asn Phe Leu Glu Lys Arg Tyr Glu Lys Trp Ile Glu Val Tyr Lys
705                 710                 715                 720
```

-continued

```
Leu Val Lys Ala Lys Trp Leu Gly Thr Val Asn Thr Gln Phe Gln Lys
                725                 730                 735

Arg Ser Tyr Gln Met Tyr Arg Ser Leu Glu Tyr Gln Val Asp Ala Ile
            740                 745                 750

Lys Lys Ile Ile Asp Tyr Glu Tyr Lys Ile Tyr Ser Gly Pro Asp Lys
            755                 760                 765

Glu Gln Ile Ala Asp Glu Ile Asn Asn Leu Lys Asn Lys Leu Glu Glu
        770                 775                 780

Lys Ala Asn Lys Ala Met Ile Asn Ile Asn Ile Phe Met Arg Glu Ser
785                 790                 795                 800

Ser Arg Ser Phe Leu Val Asn Gln Met Ile Asn Glu Ala Lys Lys Gln
                805                 810                 815

Leu Leu Glu Phe Asp Thr Gln Ser Lys Asn Ile Leu Met Gln Tyr Ile
            820                 825                 830

Lys Ala Asn Ser Lys Phe Ile Gly Ile Thr Glu Leu Lys Lys Leu Glu
            835                 840                 845

Ser Lys Ile Asn Lys Val Phe Ser Thr Pro Ile Pro Phe Ser Tyr Ser
    850                 855                 860

Lys Asn Leu Asp Cys Trp Val Asp Asn Glu Glu Asp Ile Asp Val Ile
865                 870                 875                 880

Leu Lys Lys Ser Thr Ile Leu Asn Leu Asp Ile Asn Asn Asp Ile Ile
                885                 890                 895

Ser Asp Ile Ser Gly Phe Asn Ser Ser Val Ile Thr Tyr Pro Asp Ala
            900                 905                 910

Gln Leu Val Pro Gly Ile Asn Gly Lys Ala Ile His Leu Val Asn Asn
            915                 920                 925

Glu Ser Ser Glu Val Ile Val His Lys Ala Met Asp Ile Glu Tyr Asn
    930                 935                 940

Asp Met Phe Asn Asn Phe Thr Val Ser Phe Trp Leu Arg Val Pro Lys
945                 950                 955                 960

Val Ser Ala Ser His Leu Glu Gln Tyr Gly Thr Asn Glu Tyr Ser Ile
                965                 970                 975

Ile Ser Ser Met Lys Lys His Ser Leu Ser Ile Gly Ser Gly Trp Ser
            980                 985                 990

Val Ser Leu Lys Gly Asn Asn Leu Ile Trp Thr Leu Lys Asp Ser Ala
            995                 1000                1005

Gly Glu Val Arg Gln Ile Thr Phe Arg Asp Leu Pro Asp Lys Phe Asn
        1010                1015                1020

Ala Tyr Leu Ala Asn Lys Trp Val Phe Ile Thr Ile Thr Asn Asp Arg
1025                1030                1035                1040

Leu Ser Ser Ala Asn Leu Tyr Ile Asn Gly Val Leu Met Gly Ser Ala
                1045                1050                1055

Glu Ile Thr Gly Leu Gly Ala Ile Arg Glu Asp Asn Asn Ile Thr Leu
            1060                1065                1070

Lys Leu Asp Arg Cys Asn Asn Asn Asn Gln Tyr Val Ser Ile Asp Lys
            1075                1080                1085

Phe Arg Ile Phe Cys Lys Ala Leu Asn Pro Lys Glu Ile Glu Lys Leu
        1090                1095                1100

Tyr Thr Ser Tyr Leu Ser Ile Thr Phe Leu Arg Asp Phe Trp Gly Asn
1105                1110                1115                1120

Pro Leu Arg Tyr Asp Thr Glu Tyr Tyr Leu Ile Pro Val Ala Ser Ser
                1125                1130                1135

Ser Lys Asp Val Gln Leu Lys Asn Ile Thr Asp Tyr Met Tyr Leu Thr
```

-continued

```
              1140              1145              1150

Asn Ala Pro Ser Tyr Thr Asn Gly Lys Leu Asn Ile Tyr Tyr Arg Arg
        1155              1160              1165

Leu Tyr Asn Gly Leu Lys Phe Ile Ile Lys Arg Tyr Thr Pro Asn Asn
        1170              1175              1180

Glu Ile Asp Ser Phe Val Lys Ser Gly Asp Phe Ile Lys Leu Tyr Val
1185              1190              1195              1200

Ser Tyr Asn Asn Asn Glu His Ile Val Gly Tyr Pro Lys Asp Gly Asn
                1205              1210              1215

Ala Phe Asn Asn Leu Asp Arg Ile Leu Arg Val Gly Tyr Asn Ala Pro
                1220              1225              1230

Gly Ile Pro Leu Tyr Lys Lys Met Glu Ala Val Lys Leu Arg Asp Leu
        1235              1240              1245

Lys Thr Tyr Ser Val Gln Leu Lys Leu Tyr Asp Asp Lys Asn Ala Ser
        1250              1255              1260

Leu Gly Leu Val Gly Thr His Asn Gly Gln Ile Gly Asn Asp Pro Asn
1265              1270              1275              1280

Arg Asp Ile Leu Ile Ala Ser Asn Trp Tyr Phe Asn His Leu Lys Asp
                1285              1290              1295

Lys Ile Leu Gly Cys Asp Trp Tyr Phe Val Pro Thr Asp Glu Gly Trp
        1300              1305              1310

Thr Asn Asp
        1315
```

```
<210> SEQ ID NO 24
<211> LENGTH: 567
<212> TYPE: PRT
<213> ORGANISM: Corynebacterium diphtheriae
<220> FEATURE:
<223> OTHER INFORMATION: Diphtheria toxin

<400> SEQUENCE: 24

Met Leu Val Arg Gly Tyr Val Val Ser Arg Lys Leu Phe Ala Ser Ile
1               5                  10                  15

Leu Ile Gly Ala Leu Leu Gly Ile Gly Ala Pro Pro Ser Ala His Ala
                20                  25                  30

Gly Ala Asp Asp Val Val Asp Ser Ser Lys Ser Phe Val Met Glu Asn
        35                  40                  45

Phe Ser Ser Tyr His Gly Thr Lys Pro Gly Tyr Val Asp Ser Ile Gln
        50                  55                  60

Lys Gly Ile Gln Lys Pro Lys Ser Gly Thr Gln Gly Asn Tyr Asp Asp
65                  70                  75                  80

Asp Trp Lys Gly Phe Tyr Ser Thr Asp Asn Lys Tyr Asp Ala Ala Gly
                85                  90                  95

Tyr Ser Val Asp Asn Glu Asn Pro Leu Ser Gly Lys Ala Gly Gly Val
                100                 105                 110

Val Lys Val Thr Tyr Pro Gly Leu Thr Lys Val Leu Ala Leu Lys Val
        115                 120                 125

Asp Asn Ala Glu Thr Ile Lys Lys Glu Leu Gly Leu Ser Leu Thr Glu
        130                 135                 140

Pro Leu Met Glu Gln Val Gly Thr Glu Glu Phe Ile Lys Arg Phe Gly
145                 150                 155                 160

Asp Gly Ala Ser Arg Val Val Leu Ser Leu Pro Phe Ala Glu Gly Ser
                165                 170                 175

Ser Ser Val Glu Tyr Ile Asn Asn Trp Glu Gln Ala Lys Ala Leu Ser
```

-continued

```
                180              185              190
Val Glu Leu Glu Ile Asn Phe Glu Thr Arg Gly Lys Arg Gly Gln Asp
        195              200              205

Ala Met Tyr Glu Tyr Met Ala Gln Ala Cys Ala Gly Asn Arg Val Arg
        210              215              220

Arg Ser Val Gly Ser Ser Leu Ser Cys Ile Asn Leu Asp Trp Asp Val
225              230              235              240

Ile Arg Asp Lys Thr Lys Thr Lys Ile Glu Ser Leu Lys Glu His Gly
            245              250              255

Pro Ile Lys Asn Lys Met Ser Glu Ser Pro Asn Lys Thr Val Ser Glu
            260              265              270

Glu Lys Ala Lys Gln Tyr Leu Glu Glu Phe His Gln Thr Ala Leu Glu
            275              280              285

His Pro Glu Leu Ser Glu Leu Lys Thr Val Thr Gly Thr Asn Pro Val
            290              295              300

Phe Ala Gly Ala Asn Tyr Ala Ala Trp Ala Val Asn Val Ala Gln Val
305              310              315              320

Ile Asp Ser Glu Thr Ala Asp Asn Leu Glu Lys Thr Thr Ala Ala Leu
            325              330              335

Ser Ile Leu Pro Gly Ile Gly Ser Val Met Gly Ile Ala Asp Gly Ala
            340              345              350

Val His His Asn Thr Glu Glu Ile Val Ala Gln Ser Ile Ala Leu Ser
            355              360              365

Ser Leu Met Val Ala Gln Ala Ile Pro Leu Val Gly Glu Leu Val Asp
            370              375              380

Ile Gly Phe Ala Ala Tyr Asn Phe Val Glu Ser Ile Ile Asn Leu Phe
385              390              395              400

Gln Val Val His Asn Ser Tyr Asn Arg Pro Ala Tyr Ser Pro Gly His
            405              410              415

Lys Thr Gln Pro Phe Leu His Asp Gly Tyr Ala Val Ser Trp Asn Thr
            420              425              430

Val Glu Asp Ser Ile Ile Arg Thr Gly Phe Gln Gly Glu Ser Gly His
            435              440              445

Asp Ile Lys Ile Thr Ala Glu Asn Thr Pro Leu Pro Ile Ala Gly Val
            450              455              460

Leu Leu Pro Thr Ile Pro Gly Lys Leu Asp Val Asn Lys Ser Lys Thr
465              470              475              480

His Ile Ser Val Asn Gly Arg Lys Ile Arg Met Arg Cys Arg Ala Ile
            485              490              495

Asp Gly Asp Val Thr Phe Cys Arg Pro Lys Ser Pro Val Tyr Val Gly
            500              505              510

Asn Gly Val His Ala Asn Leu His Val Ala Phe His Arg Ser Ser Ser
            515              520              525

Glu Lys Ile His Ser Asn Glu Ile Ser Ser Asp Ser Ile Gly Val Leu
            530              535              540

Gly Tyr Gln Lys Thr Val Asp His Thr Lys Val Asn Ser Lys Leu Ser
545              550              555              560

Leu Phe Phe Glu Ile Lys Ser
            565
```

<210> SEQ ID NO 25
<211> LENGTH: 18
<212> TYPE: PRT
<213> ORGANISM: Clostridium tetani -continued

```
<220> FEATURE:
<223> OTHER INFORMATION: MTTE

<400> SEQUENCE: 25

Phe Ile Gly Ile Thr Glu Leu Lys Lys Leu Glu Ser Lys Ile Asn Lys
1               5                   10                  15

Val Phe

<210> SEQ ID NO 26
<211> LENGTH: 13
<212> TYPE: PRT
<213> ORGANISM: Artificial Sequence
<220> FEATURE:
<223> OTHER INFORMATION: Peptide

<400> SEQUENCE: 26

Phe Ile Gly Ile Thr Glu Leu Lys Lys Leu Glu Ser Lys
1               5                   10

<210> SEQ ID NO 27
<211> LENGTH: 14
<212> TYPE: PRT
<213> ORGANISM: Artificial Sequence
<220> FEATURE:
<223> OTHER INFORMATION: Peptide

<400> SEQUENCE: 27

Phe Ile Gly Ile Thr Glu Leu Lys Lys Leu Glu Ser Lys Ile
1               5                   10

<210> SEQ ID NO 28
<211> LENGTH: 15
<212> TYPE: PRT
<213> ORGANISM: Artificial Sequence
<220> FEATURE:
<223> OTHER INFORMATION: Peptide

<400> SEQUENCE: 28

Phe Ile Gly Ile Thr Glu Leu Lys Lys Leu Glu Ser Lys Ile Asn
1               5                   10                  15

<210> SEQ ID NO 29
<211> LENGTH: 16
<212> TYPE: PRT
<213> ORGANISM: Artificial Sequence
<220> FEATURE:
<223> OTHER INFORMATION: Peptide

<400> SEQUENCE: 29

Phe Ile Gly Ile Thr Glu Leu Lys Lys Leu Glu Ser Lys Ile Asn Lys
1               5                   10                  15

<210> SEQ ID NO 30
<211> LENGTH: 12
<212> TYPE: PRT
<213> ORGANISM: Artificial Sequence
<220> FEATURE:
<223> OTHER INFORMATION: Peptide

<400> SEQUENCE: 30

Tyr Ile Gly Ile Thr Glu Leu Lys Lys Leu Glu Ser
1               5                   10

<210> SEQ ID NO 31
<211> LENGTH: 12
<212> TYPE: PRT
```

```
<213> ORGANISM: Artificial Sequence
<220> FEATURE:
<223> OTHER INFORMATION: Peptide

<400> SEQUENCE: 31

Phe Val Gly Ile Thr Glu Leu Lys Lys Leu Glu Ser
1               5                   10

<210> SEQ ID NO 32
<211> LENGTH: 12
<212> TYPE: PRT
<213> ORGANISM: Artificial Sequence
<220> FEATURE:
<223> OTHER INFORMATION: Peptide

<400> SEQUENCE: 32

Phe Ile Val Ile Thr Glu Leu Lys Lys Leu Glu Ser
1               5                   10

<210> SEQ ID NO 33
<211> LENGTH: 12
<212> TYPE: PRT
<213> ORGANISM: Artificial Sequence
<220> FEATURE:
<223> OTHER INFORMATION: Peptide

<400> SEQUENCE: 33

Phe Ile Gly Val Thr Glu Leu Lys Lys Leu Glu Ser
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Peptide

<400> SEQUENCE: 34

Phe Ile Gly Ile Ser Glu Leu Lys Lys Leu Glu Ser
1               5                   10

<210> SEQ ID NO 35
<211> LENGTH: 12
<212> TYPE: PRT
<213> ORGANISM: Artificial Sequence
<220> FEATURE:
<223> OTHER INFORMATION: Peptide

<400> SEQUENCE: 35

Phe Ile Gly Ile Thr Asp Leu Lys Lys Leu Glu Ser
1               5                   10

<210> SEQ ID NO 36
<211> LENGTH: 12
<212> TYPE: PRT
<213> ORGANISM: Artificial Sequence
<220> FEATURE:
<223> OTHER INFORMATION: Peptide

<400> SEQUENCE: 36

Phe Ile Gly Ile Thr Glu Val Lys Lys Leu Glu Ser
1               5                   10

<210> SEQ ID NO 37
<211> LENGTH: 12
<212> TYPE: PRT
<213> ORGANISM: Artificial Sequence
```

<220> FEATURE:
<223> OTHER INFORMATION: Peptide

<400> SEQUENCE: 37

Phe Ile Gly Ile Thr Glu Leu Val Lys Leu Glu Ser
1               5                   10

<210> SEQ ID NO 38
<211> LENGTH: 12
<212> TYPE: PRT
<213> ORGANISM: Artificial Sequence
<220> FEATURE:
<223> OTHER INFORMATION: Peptide

<400> SEQUENCE: 38

Phe Ile Gly Ile Thr Glu Leu Lys Val Leu Glu Ser
1               5                   10

<210> SEQ ID NO 39
<211> LENGTH: 12
<212> TYPE: PRT
<213> ORGANISM: Artificial Sequence
<220> FEATURE:
<223> OTHER INFORMATION: Peptide

<400> SEQUENCE: 39

Phe Ile Gly Ile Thr Glu Leu Lys Lys Val Glu Ser
1               5                   10

<210> SEQ ID NO 40
<211> LENGTH: 12
<212> TYPE: PRT
<213> ORGANISM: Artificial Sequence
<220> FEATURE:
<223> OTHER INFORMATION: Peptide

<400> SEQUENCE: 40

Phe Ile Gly Ile Thr Glu Leu Lys Lys Leu Asp Ser
1               5                   10

<210> SEQ ID NO 41
<211> LENGTH: 12
<212> TYPE: PRT
<213> ORGANISM: Artificial Sequence
<220> FEATURE:
<223> OTHER INFORMATION: Peptide

<400> SEQUENCE: 41

Phe Ile Gly Ile Thr Glu Leu Lys Lys Leu Glu Thr
1               5                   10

<210> SEQ ID NO 42
<211> LENGTH: 11
<212> TYPE: PRT
<213> ORGANISM: Artificial Sequence
<220> FEATURE:
<223> OTHER INFORMATION: Peptide

<400> SEQUENCE: 42

Asn Asp Tyr Lys Ala Ile Ala Asn Lys Leu Ser
1               5                   10

<210> SEQ ID NO 43
<211> LENGTH: 13
<212> TYPE: PRT
<213> ORGANISM: Artificial Sequence
<220> FEATURE:

```
<223> OTHER INFORMATION: Peptide

<400> SEQUENCE: 43

Leu Met His Glu Leu Ile His Val Leu His Gly Leu Tyr
1               5                   10

<210> SEQ ID NO 44
<211> LENGTH: 15
<212> TYPE: PRT
<213> ORGANISM: Artificial Sequence
<220> FEATURE:
<223> OTHER INFORMATION: Peptide

<400> SEQUENCE: 44

Leu Met His Glu Leu Ile His Val Leu His Gly Leu Tyr Gly Met
1               5                   10                  15

<210> SEQ ID NO 45
<211> LENGTH: 9
<212> TYPE: PRT
<213> ORGANISM: Artificial Sequence
<220> FEATURE:
<223> OTHER INFORMATION: Peptide

<400> SEQUENCE: 45

Leu Ile His Val Leu His Gly Leu Tyr
1               5

<210> SEQ ID NO 46
<211> LENGTH: 14
<212> TYPE: PRT
<213> ORGANISM: Artificial Sequence
<220> FEATURE:
<223> OTHER INFORMATION: Peptide

<400> SEQUENCE: 46

Pro Ala Leu Leu Leu Met His Glu Leu Ile His Val Leu His
1               5                   10

<210> SEQ ID NO 47
<211> LENGTH: 244
<212> TYPE: PRT
<213> ORGANISM: Artificial Sequence
<220> FEATURE:
<223> OTHER INFORMATION: scFv 14GIIICII-b

<400> SEQUENCE: 47

Gln Val Gln Leu Gln Gln Pro Gly Ala Glu Leu Val Met Pro Gly Ala
1               5                   10                  15

Ser Val Asn Leu Ser Cys Lys Ala Ser Gly Tyr Thr Phe Thr Asp Tyr
            20                  25                  30

Trp Met His Trp Val Lys Gln Arg Pro Gly Gln Gly Leu Glu Trp Ile
        35                  40                  45

Gly Glu Ile Asp Pro Ser Asp Asn Phe Ser Asn Leu Asn Gln Asn Phe
    50                  55                  60

Arg Gly Lys Ala Thr Leu Thr Val Asp Lys Ser Ser Arg Thr Ala Phe
65                  70                  75                  80

Leu Gln Leu Ser Ser Leu Thr Ser Glu Asp Ser Ala Val Tyr Tyr Cys
                85                  90                  95

Ala Val Glu Asp Tyr Trp Gly Gln Gly Thr Thr Leu Thr Val Ser Ser
            100                 105                 110

Gly Gly Gly Gly Ser Gly Gly Gly Gly Ser Gly Gly Gly Gly Ser Gly
        115                 120                 125
```

```
Gly Gly Gly Ser Asp Ile Val Met Thr Gln Ala Thr Pro Ser Val Leu
    130             135             140
```

```
Val Thr Pro Gly Glu Ala Val Ser Ile Ser Cys Arg Ala Ser Arg Ser
145             150             155             160
```

```
Leu Leu His Ser Asn Gly Ile Thr Tyr Leu Tyr Trp Phe Leu Gln Arg
                165             170             175
```

```
Pro Gly Gln Ser Pro Gln Val Leu Ile Tyr Arg Met Ser Asn Leu Val
                180             185             190
```

```
Ser Gly Val Pro Asp Arg Phe Ser Gly Ser Gly Ser Gly Thr Ala Phe
                195             200             205
```

```
Thr Leu Arg Ile Ser Arg Val Glu Ala Glu Asp Val Gly Val Tyr Tyr
    210             215             220
```

```
Cys Met Gln His Leu Glu Phe Pro Tyr Thr Phe Gly Gly Gly Thr Lys
225             230             235             240
```

```
Leu Glu Ile Lys
```

```
<210> SEQ ID NO 48
<211> LENGTH: 245
<212> TYPE: PRT
<213> ORGANISM: Artificial Sequence
<220> FEATURE:
<223> OTHER INFORMATION: scFv 1BIIICI-b
```

```
<400> SEQUENCE: 48
```

```
Glu Val Arg Leu Leu Gln Ser Gly Ala Ala Leu Val Arg Pro Gly Ala
1               5               10              15
```

```
Ser Val Lys Leu Ser Cys Thr Ala Ser Gly Phe Asn Ile Lys Asp Phe
                20              25              30
```

```
Asn Ile His Trp Val Lys Gln Arg Pro Glu Gln Gly Leu Glu Trp Ile
                35              40              45
```

```
Gly Arg Ile Asp Pro Glu Asn Gly Asp Ala Glu Tyr Val Pro Lys Phe
    50              55              60
```

```
Gln Val Arg Ala Thr Met Thr Thr Asp Thr Ser Ser Asn Thr Val Tyr
65              70              75              80
```

```
Leu His Leu Ser Ser Leu Thr Ser Gly Asp Thr Ala Val Tyr Tyr Cys
                85              90              95
```

```
Thr Thr Gly Ser Tyr Asp Leu Asp Val Glu Tyr Trp Gly Gln Gly Thr
                100             105             110
```

```
Thr Leu Thr Val Ser Ser Gly Gly Gly Gly Ser Gly Gly Gly Gly Ser
    115             120             125
```

```
Gly Gly Gly Gly Ser Gly Gly Gly Gly Ser Glu Leu Gln Met Thr Gln
    130             135             140
```

```
Ser Pro Ser Ser Leu Ser Ala Ser Leu Gly Asp Thr Val Thr Ile Thr
145             150             155             160
```

```
Cys His Ala Ser Gln Asn Ile Asn Val Trp Leu Ser Trp Tyr Gln Gln
                165             170             175
```

```
Arg Pro Gly Asn Ile Pro Lys Leu Leu Ile Tyr Lys Ala Ser Thr Leu
                180             185             190
```

```
His Thr Gly Val Pro Ser Arg Phe Arg Gly Ser Gly Ser Gly Thr Gly
                195             200             205
```

```
Phe Thr Leu Thr Ile Ser Ser Leu Gln Pro Glu Asp Ile Ala Thr Tyr
    210             215             220
```

```
Tyr Cys Gln Gln Gly Gln Ser Tyr Pro Leu Thr Phe Gly Ala Gly Thr
225             230             235             240
```

-continued

```
Lys Leu Glu Leu Lys
            245

<210> SEQ ID NO 49
<211> LENGTH: 8
<212> TYPE: PRT
<213> ORGANISM: Artificial Sequence
<220> FEATURE:
<223> OTHER INFORMATION: 14GIIICII-b VHCDR1

<400> SEQUENCE: 49

Gly Tyr Thr Phe Thr Asp Tyr Trp
1               5

<210> SEQ ID NO 50
<211> LENGTH: 8
<212> TYPE: PRT
<213> ORGANISM: Artificial Sequence
<220> FEATURE:
<223> OTHER INFORMATION: 14GIIICII-b VHCDR2

<400> SEQUENCE: 50

Ile Asp Pro Ser Asp Asn Phe Ser
1               5

<210> SEQ ID NO 51
<211> LENGTH: 5
<212> TYPE: PRT
<213> ORGANISM: Artificial Sequence
<220> FEATURE:
<223> OTHER INFORMATION: 14GIIICII-b VHCDR3

<400> SEQUENCE: 51

Ala Val Glu Asp Tyr
1               5

<210> SEQ ID NO 52
<211> LENGTH: 11
<212> TYPE: PRT
<213> ORGANISM: Artificial Sequence
<220> FEATURE:
<223> OTHER INFORMATION: 14GIIICII-b VLCDR1

<400> SEQUENCE: 52

Arg Ser Leu Leu His Ser Asn Gly Ile Thr Tyr
1               5                   10

<210> SEQ ID NO 53

<400> SEQUENCE: 53

000

<210> SEQ ID NO 54
<211> LENGTH: 9
<212> TYPE: PRT
<213> ORGANISM: Artificial Sequence
<220> FEATURE:
<223> OTHER INFORMATION: 14GIIICII-b VLCDR3

<400> SEQUENCE: 54

Met Gln His Leu Glu Phe Pro Tyr Thr
1               5

<210> SEQ ID NO 55
<211> LENGTH: 8
<212> TYPE: PRT
```

-continued

```
<213> ORGANISM: Artificial Sequence
<220> FEATURE:
<223> OTHER INFORMATION: 1BIIICI-b VHCDR1

<400> SEQUENCE: 55

Gly Phe Asn Ile Lys Asp Phe Asn
1               5

<210> SEQ ID NO 56
<211> LENGTH: 8
<212> TYPE: PRT
<213> ORGANISM: Artificial Sequence
<220> FEATURE:
<223> OTHER INFORMATION: 1BIIICI-b VHCDR2

<400> SEQUENCE: 56

Ile Asp Pro Glu Asn Gly Asp Ala
1               5

<210> SEQ ID NO 57
<211> LENGTH: 11
<212> TYPE: PRT
<213> ORGANISM: Artificial Sequence
<220> FEATURE:
<223> OTHER INFORMATION: 1BIIICI-b VHCDR3

<400> SEQUENCE: 57

Thr Thr Gly Ser Tyr Asp Leu Asp Val Glu Tyr
1               5                   10

<210> SEQ ID NO 58
<211> LENGTH: 6
<212> TYPE: PRT
<213> ORGANISM: Artificial Sequence
<220> FEATURE:
<223> OTHER INFORMATION: 1BIIICI-b VLCDR1

<400> SEQUENCE: 58

Gln Asn Ile Asn Val Trp
1               5

<210> SEQ ID NO 59

<400> SEQUENCE: 59

000

<210> SEQ ID NO 60
<211> LENGTH: 9
<212> TYPE: PRT
<213> ORGANISM: Artificial Sequence
<220> FEATURE:
<223> OTHER INFORMATION: 1BIIICI-b VLCDR3

<400> SEQUENCE: 60

Gln Gln Gly Gln Ser Tyr Pro Leu Thr
1               5

<210> SEQ ID NO 61
<211> LENGTH: 108
<212> TYPE: PRT
<213> ORGANISM: Artificial Sequence
<220> FEATURE:
<223> OTHER INFORMATION: Y-SM083-B8 VL

<400> SEQUENCE: 61

Asp Ile Gln Met Thr Gln Ser Pro Ser Ser Leu Ser Ala Ser Val Gly
```

-continued

```
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Gly Tyr Pro Pro
                85                  90                  95

Phe Thr Phe Gly Gln Gly Thr Lys Leu Glu Ile Lys
            100                 105
```

<210> SEQ ID NO 62
<211> LENGTH: 116
<212> TYPE: PRT
<213> ORGANISM: Artificial Sequence
<220> FEATURE:
<223> OTHER INFORMATION: Y-SM083-B8 VH

<400> SEQUENCE: 62

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Val Trp Gly Ile Asp Tyr Trp Gly Gln Gly Thr Leu Val
            100                 105                 110

Thr Val Ser Ser
        115
```

<210> SEQ ID NO 63
<211> LENGTH: 10
<212> TYPE: PRT
<213> ORGANISM: Artificial Sequence
<220> FEATURE:
<223> OTHER INFORMATION: Peptide

<400> SEQUENCE: 63

```
Glu Pro Pro Thr Ala Cys Arg Glu Lys Gln
1               5                   10
```

<210> SEQ ID NO 64
<211> LENGTH: 12
<212> TYPE: PRT
<213> ORGANISM: Artificial Sequence
<220> FEATURE:
<223> OTHER INFORMATION: Peptide

<400> SEQUENCE: 64

```
Glu Pro Pro Thr Ala Cys Arg Glu Lys Gln Tyr Leu
1               5                   10
```

```
<210> SEQ ID NO 65
<211> LENGTH: 10
<212> TYPE: PRT
<213> ORGANISM: Artificial Sequence
<220> FEATURE:
<223> OTHER INFORMATION: Peptide

<400> SEQUENCE: 65

Glu Cys Leu Pro Cys Gly Glu Ser Glu Phe
1               5                   10

<210> SEQ ID NO 66
<211> LENGTH: 248
<212> TYPE: PRT
<213> ORGANISM: Artificial Sequence
<220> FEATURE:
<223> OTHER INFORMATION: FITC8 scFv

<400> SEQUENCE: 66

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Ser Trp Val Arg Gln Ala Pro Gly Lys Gly Leu Glu Trp Val
        35                  40                  45

Ser Gly Ile Ser Gly Asn Gly Gly Tyr Thr Tyr Phe Ala Asp Ser Val
    50                  55                  60

Lys Asp Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Gly Gly Asp Gly Ser Gly Trp Ser Phe Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Gly Ser Gly Gly Gly Gly Ser Gln Ser Val Leu Thr Gln Pro
    130                 135                 140

Pro Ser Ala Ser Gly Thr Pro Gly Gln Arg Val Thr Ile Ser Cys Thr
145                 150                 155                 160

Gly Ser Ser Ser Asn Ile Gly Ala Gly Tyr Asp Val His Trp Tyr Gln
                165                 170                 175

Gln Leu Pro Gly Thr Ala Pro Lys Leu Leu Ile Tyr Gly Asn Asn Asn
            180                 185                 190

Arg Pro Ser Gly Val Pro Asp Arg Phe Ser Gly Ser Lys Ser Gly Thr
        195                 200                 205

Ser Ala Ser Leu Ala Ile Ser Gly Leu Arg Ser Glu Asp Glu Ala Asp
    210                 215                 220

Tyr Tyr Cys Ala Ala Trp Asp Asp Ser Leu Ser Gly Arg Val Phe Gly
225                 230                 235                 240

Gly Gly Thr Lys Leu Thr Val Leu
                245

<210> SEQ ID NO 67
<211> LENGTH: 38
<212> TYPE: PRT
<213> ORGANISM: Artificial Sequence
<220> FEATURE:
<223> OTHER INFORMATION: Peptide
```

-continued

<400> SEQUENCE: 67

Phe Ile Gly Ile Thr Glu Leu Lys Lys Leu Glu Ser Lys Ile Asn Lys
1               5                   10                  15

Val Phe Ala Val Gly Ala Leu Lys Val Pro Arg Asn Gln Asp Trp Leu
            20                  25                  30

Gly Val Pro Arg Gln Leu
        35

<210> SEQ ID NO 68
<211> LENGTH: 240
<212> TYPE: PRT
<213> ORGANISM: Artificial Sequence
<220> FEATURE:
<223> OTHER INFORMATION: scFv Y-SM083-p03-C06

<400> SEQUENCE: 68

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ser Ile Ser Ser Ser Ser Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Gly Arg Trp Gly Tyr Tyr Phe Asp Tyr Trp Gly Gln Gly
            100                 105                 110

Thr Leu Val Thr Val Ser Ser Gly Gly Gly Gly Ser Gly Gly Gly Gly
            115                 120                 125

Ser Gly Gly Gly Gly Ser Asp Ile Gln Met Thr Gln Ser Pro Ser Ser
        130                 135                 140

Leu Ser Ala Ser Val Gly Asp Arg Val Thr Ile Thr Cys Arg Ala Ser
145                 150                 155                 160

Gln Ser Ile Ser Ser Tyr Leu Asn Trp Tyr Gln Gln Lys Pro Gly Lys
                165                 170                 175

Ala Pro Lys Leu Leu Ile Tyr Ala Ala Ser Ser Leu Gln Ser Gly Val
            180                 185                 190

Pro Ser Arg Phe Ser Gly Ser Gly Ser Gly Thr Asp Phe Thr Leu Thr
            195                 200                 205

Ile Ser Ser Leu Gln Pro Glu Asp Phe Ala Thr Tyr Tyr Cys Gln Gln
        210                 215                 220

Ile Ser Gly Pro Phe Thr Phe Gly Gln Gly Thr Lys Leu Glu Ile Lys
225                 230                 235                 240

<210> SEQ ID NO 69
<211> LENGTH: 243
<212> TYPE: PRT
<213> ORGANISM: Artificial Sequence
<220> FEATURE:
<223> OTHER INFORMATION: scFv Y-SM083-p04-C04

<400> SEQUENCE: 69

Glu Val Gln Leu Leu Glu Ser Gly Gly Gly Leu Val Gln Pro Gly Gly
1               5                   10                  15

-continued

```
Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Pro Pro Pro Ser Ser Ser Arg Ser Tyr Leu Asp Tyr Trp
            100                 105                 110

Gly Gln Gly Thr Leu Val Thr Val Ser Ser Gly Gly Gly Gly Ser Gly
            115                 120                 125

Gly Gly Gly Ser Gly Gly Gly Ser Asp Ile Gln Met Thr Gln Ser
        130                 135                 140

Pro Ser Ser Leu Ser Ala Ser Val Gly Asp Arg Val Thr Ile Thr Cys
145                 150                 155                 160

Arg Ala Ser Gln Ser Ile Ser Ser Tyr Leu Asn Trp Tyr Gln Gln Lys
                165                 170                 175

Pro Gly Lys Ala Pro Lys Leu Leu Ile Tyr Ala Ala Ser Ser Leu Gln
            180                 185                 190

Ser Gly Val Pro Ser Arg Phe Ser Gly Ser Gly Ser Gly Thr Asp Phe
            195                 200                 205

Thr Leu Thr Ile Ser Ser Leu Gln Pro Glu Asp Phe Ala Thr Tyr Tyr
        210                 215                 220

Cys Gln Gln Tyr Tyr Pro Leu Phe Thr Phe Gly Gln Gly Thr Lys Leu
225                 230                 235                 240

Glu Ile Lys
```

```
<210> SEQ ID NO 70
<211> LENGTH: 239
<212> TYPE: PRT
<213> ORGANISM: Artificial Sequence
<220> FEATURE:
<223> OTHER INFORMATION: scFV Y-SM083-p04-D04

<400> SEQUENCE: 70

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Tyr Met Tyr Trp Val Arg Gln Ala Pro Gly Lys Gly Leu Glu Trp Val
            35                  40                  45

Ser Tyr Ile Gly Tyr Ser Gly Gly Thr Gly Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Pro Phe Gly Ala Phe Asp Tyr Trp Gly Gln Gly Thr Leu
            100                 105                 110

Val Thr Val Ser Ser Gly Gly Gly Gly Ser Gly Gly Gly Gly Ser Gly
        115                 120                 125
```

```
Gly Gly Gly Ser Asp Ile Gln Met Thr Gln Ser Pro Ser Ser Leu Ser
    130             135             140
```

```
Ala Ser Val Gly Asp Arg Val Thr Ile Thr Cys Arg Ala Ser Gln Ser
145             150             155             160
```

```
Ile Ser Ser Tyr Leu Asn Trp Tyr Gln Gln Lys Pro Gly Lys Ala Pro
            165             170             175
```

```
Lys Leu Leu Ile Tyr Ala Ala Ser Ser Leu Gln Ser Gly Val Pro Ser
            180             185             190
```

```
Arg Phe Ser Gly Ser Gly Ser Gly Thr Asp Phe Thr Leu Thr Ile Ser
            195             200             205
```

```
Ser Leu Gln Pro Glu Asp Phe Ala Thr Tyr Tyr Cys Gln Gln Tyr Tyr
    210             215             220
```

```
Gly Phe Pro Tyr Thr Phe Gly Gln Gly Thr Lys Leu Glu Ile Lys
225             230             235
```

<210> SEQ ID NO 71
<211> LENGTH: 244
<212> TYPE: PRT
<213> ORGANISM: Artificial Sequence
<220> FEATURE:
<223> OTHER INFORMATION: scFv Y-SM083-p04-F04

<400> SEQUENCE: 71

```
Glu Val Gln Leu Leu Glu Ser Gly Gly Gly Leu Val Gln Pro Gly Gly
1               5               10              15
```

```
Ser Leu Arg Leu Ser Cys Ala Ala Ser Gly Phe Thr Phe Ser Ser Tyr
            20              25              30
```

```
Ala Met Ser Trp Val Arg Gln Ala Pro Gly Lys Gly Leu Glu Trp Val
            35              40              45
```

```
Ser Ala Ile Ser Gly Ser Gly Gly Ser Thr Tyr Tyr Ala Asp Ser Val
    50              55              60
```

```
Lys Gly Arg Phe Thr Ile Ser Arg Asp Asn Ser Lys Asn Thr Leu Tyr
65              70              75              80
```

```
Leu Gln Met Asn Ser Leu Arg Ala Glu Asp Thr Ala Val Tyr Tyr Cys
            85              90              95
```

```
Ala Arg Tyr Pro Arg Pro Tyr Ser Ile Phe Ile Ser Ile Asp Tyr Trp
            100             105             110
```

```
Gly Gln Gly Thr Leu Val Thr Val Ser Ser Gly Gly Gly Gly Ser Gly
            115             120             125
```

```
Gly Gly Gly Ser Gly Gly Gly Gly Ser Asp Ile Gln Met Thr Gln Ser
    130             135             140
```

```
Pro Ser Ser Leu Ser Ala Ser Val Gly Asp Arg Val Thr Ile Thr Cys
145             150             155             160
```

```
Arg Ala Ser Gln Ser Ile Ser Ser Tyr Leu Asn Trp Tyr Gln Gln Lys
            165             170             175
```

```
Pro Gly Lys Ala Pro Lys Leu Leu Ile Tyr Ala Ala Ser Ser Leu Gln
            180             185             190
```

```
Ser Gly Val Pro Ser Arg Phe Ser Gly Ser Gly Ser Gly Thr Asp Phe
            195             200             205
```

```
Thr Leu Thr Ile Ser Ser Leu Gln Pro Glu Asp Phe Ala Thr Tyr Tyr
    210             215             220
```

```
Cys Gln Gln Thr Tyr Gly Thr Pro Phe Thr Phe Gly Gln Gly Thr Lys
225             230             235             240
```

```
Leu Glu Ile Lys
```

-continued

<210> SEQ ID NO 72
<211> LENGTH: 243
<212> TYPE: PRT
<213> ORGANISM: Artificial Sequence
<220> FEATURE:
<223> OTHER INFORMATION: scFv Y SM083-p04-G04

<400> SEQUENCE: 72

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Ser Val Pro Tyr Ser Pro Tyr Tyr Ser Phe Asp Tyr Trp
            100                 105                 110

Gly Gln Gly Thr Leu Val Thr Val Ser Ser Gly Gly Gly Gly Ser Gly
            115                 120                 125

Gly Gly Gly Ser Gly Gly Gly Gly Ser Asp Ile Gln Met Thr Gln Ser
    130                 135                 140

Pro Ser Ser Leu Ser Ala Ser Val Gly Asp Arg Val Thr Ile Thr Cys
145                 150                 155                 160

Arg Ala Ser Gln Ser Ile Ser Ser Tyr Leu Asn Trp Tyr Gln Gln Lys
                165                 170                 175

Pro Gly Lys Ala Pro Lys Leu Leu Ile Tyr Ala Ala Ser Ser Leu Gln
            180                 185                 190

Ser Gly Val Pro Ser Arg Phe Ser Gly Ser Gly Ser Gly Thr Asp Phe
            195                 200                 205

Thr Leu Thr Ile Ser Ser Leu Gln Pro Glu Asp Phe Ala Thr Tyr Tyr
    210                 215                 220

Cys Gln Gln Thr Tyr Ser Pro Pro Thr Phe Gly Gln Gly Thr Lys Leu
225                 230                 235                 240

Glu Ile Lys

<210> SEQ ID NO 73
<211> LENGTH: 243
<212> TYPE: PRT
<213> ORGANISM: Artificial Sequence
<220> FEATURE:
<223> OTHER INFORMATION: scFv Y-SM083-p04-H04

<400> SEQUENCE: 73

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr

-continued

```
65              70              75              80

Leu Gln Met Asn Ser Leu Arg Ala Glu Asp Thr Ala Val Tyr Tyr Cys
                85              90              95

Ala Arg Tyr Thr Tyr Gly Gly Phe Pro Phe Ser Ser Phe Asp Tyr Trp
            100             105             110

Gly Gln Gly Thr Leu Val Thr Val Ser Ser Gly Gly Gly Ser Gly
            115             120             125

Gly Gly Gly Ser Gly Gly Gly Ser Asp Ile Gln Met Thr Gln Ser
    130             135             140

Pro Ser Ser Leu Ser Ala Ser Val Gly Asp Arg Val Thr Ile Thr Cys
145             150             155             160

Arg Ala Ser Gln Ser Ile Ser Ser Tyr Leu Asn Trp Tyr Gln Gln Lys
            165             170             175

Pro Gly Lys Ala Pro Lys Leu Leu Ile Tyr Ala Ala Ser Ser Leu Gln
            180             185             190

Ser Gly Val Pro Ser Arg Phe Ser Gly Ser Gly Ser Gly Thr Asp Phe
            195             200             205

Thr Leu Thr Ile Ser Ser Leu Gln Pro Glu Asp Phe Ala Thr Tyr Tyr
    210             215             220

Cys Gln Gln Tyr Arg Phe Leu Ser Thr Phe Gly Gln Gly Thr Lys Leu
225             230             235             240

Glu Ile Lys

<210> SEQ ID NO 74
<211> LENGTH: 447
<212> TYPE: PRT
<213> ORGANISM: Artificial Sequence
<220> FEATURE:
<223> OTHER INFORMATION: A9 VH domain and IgG2 C127S constant domain

<400> SEQUENCE: 74

Glu Val Gln Leu Leu Glu Ser Gly Gly Gly Leu Val Gln Pro Gly Gly
1               5               10              15

Ser Leu Arg Leu Ser Cys Ala Ala Ser Gly Phe Thr Phe Ser Ser Tyr
            20              25              30

Ala Met Ser Trp Val Arg Gln Ala Pro Gly Lys Gly Leu Glu Trp Val
            35              40              45

Ser Gly Ile Ser Gly Tyr Ser Gly Ser Thr Tyr Tyr Ala Asp Ser Val
    50              55              60

Lys Gly Arg Phe Thr Ile Ser Arg Asp Asn Ser Lys Asn Thr Leu Tyr
65              70              75              80

Leu Gln Met Asn Ser Leu Arg Ala Glu Asp Thr Ala Val Tyr Tyr Cys
                85              90              95

Ala Arg Tyr Tyr Ser Tyr Tyr Gly Tyr Tyr Tyr Phe Asp Tyr Trp Gly
            100             105             110

Gln Gly Thr Leu Val Thr Val Ser Ser Ala Ser Thr Lys Gly Pro Ser
            115             120             125

Val Phe Pro Leu Ala Pro Ser Ser Arg Ser Thr Ser Glu Ser Thr Ala
            130             135             140

Ala Leu Gly Cys Leu Val Lys Asp Tyr Phe Pro Glu Pro Val Thr Val
145             150             155             160

Ser Trp Asn Ser Gly Ala Leu Thr Ser Gly Val His Thr Phe Pro Ala
            165             170             175

Val Leu Gln Ser Ser Gly Leu Tyr Ser Leu Ser Ser Val Val Thr Val
            180             185             190
```

```
Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Cys Cys
    210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
                260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
    290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
        340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
        435                 440                 445
```

<210> SEQ ID NO 75
<211> LENGTH: 321
<212> TYPE: DNA
<213> ORGANISM: Artificial Sequence
<220> FEATURE:
<223> OTHER INFORMATION: A9 light chain variable domain

<400> SEQUENCE: 75

```
gacatccaga tgacccagtc tccatcctcc ctgagcgcat ctgtaggaga ccgcgtcacc      60
atcacctgca gggcaagtca gagcattagc agctatttaa attggtatca gcagaaacca     120
gggaaagccc ctaagctcct gatctatgct gcatccagtt tgcaaagtgg ggtcccatca     180
cgtttcagtg gcagtggaag cgggacagat ttcactctca ccatcagcag tctgcaacct     240
gaagattttg caacttatta ctgtcaacag ggttacccgt acccgttcac ttttggccag     300
gggaccaagc tggagatcaa a                                               321
```

<210> SEQ ID NO 76
<211> LENGTH: 363
<212> TYPE: DNA
<213> ORGANISM: Artificial Sequence
<220> FEATURE:
<223> OTHER INFORMATION: A9 heavy chain variable domain

<400> SEQUENCE: 76
gaggtgcaat tgttggagag cggggggaggc ttggtacagc ctgggggggtc cctgcgcctc        60 tcctgtgcag ccagcggatt caccttttagc agctatgcca tgagctgggt ccgccaggct       120
ccagggaagg ggctggagtg ggtctcaggt atttctggtt acagtggttc tacatactat       180
gcagactccg tgaagggccg gttcaccatc tcccgtgaca attccaagaa cacgctgtat       240
ctgcaaatga acagcctgcg tgccgaggac acggctgtat attattgtgc gcgctactac       300
tcttactacg gttactacta ctttgactat tgggggccaag gaaccctggt caccgtctcc       360
tca                                                                       363

<210> SEQ ID NO 77
<211> LENGTH: 330
<212> TYPE: PRT
<213> ORGANISM: Artificial Sequence
<220> FEATURE:
<223> OTHER INFORMATION: IgG hybrid constant region

<400> SEQUENCE: 77

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Arg Lys Cys Cys Val Glu Cys Pro Pro Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

-continued

```
Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 78
<211> LENGTH: 330
<212> TYPE: PRT
<213> ORGANISM: Artificial Sequence
<220> FEATURE:
<223> OTHER INFORMATION: IgG1 constant region sequence

<400> SEQUENCE: 78

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320
```

```
Gln Lys Ser Leu Ser Leu Ser Pro Gly Lys
            325                 330

<210> SEQ ID NO 79
<211> LENGTH: 40
<212> TYPE: PRT
<213> ORGANISM: Artificial Sequence
<220> FEATURE:
<223> OTHER INFORMATION: UU-01

<400> SEQUENCE: 79

Phe Ile Gly Ile Thr Glu Leu Lys Lys Leu Glu Ser Lys Ile Asn Lys
1               5                   10                  15

Val Phe Ala Gly Ile Leu Ala Arg Asn Leu Val Pro Met Val Ala Thr
            20                  25                  30

Val Gln Gly Gln Asn Leu Lys Tyr
        35                  40

<210> SEQ ID NO 80
<211> LENGTH: 5
<212> TYPE: PRT
<213> ORGANISM: Artificial Sequence
<220> FEATURE:
<223> OTHER INFORMATION: Linker

<400> SEQUENCE: 80

Glu Ala Ala Ala Lys
1               5

<210> SEQ ID NO 81
<211> LENGTH: 10
<212> TYPE: PRT
<213> ORGANISM: Artificial Sequence
<220> FEATURE:
<223> OTHER INFORMATION: Linker

<400> SEQUENCE: 81

Glu Ala Ala Ala Lys Glu Ala Ala Ala Lys
1               5                   10

<210> SEQ ID NO 82
<211> LENGTH: 12
<212> TYPE: PRT
<213> ORGANISM: Artificial Sequence
<220> FEATURE:
<223> OTHER INFORMATION: Linker

<400> SEQUENCE: 82

Gly Gly Gly Ser Gly Gly Gly Ser Gly Gly Gly Ser
1               5                   10

<210> SEQ ID NO 83
<211> LENGTH: 16
<212> TYPE: PRT
<213> ORGANISM: Artificial Sequence
<220> FEATURE:
<223> OTHER INFORMATION: Linker

<400> SEQUENCE: 83

Gly Gly Gly Ser Gly Gly Gly Ser Gly Gly Gly Ser Gly Gly Gly Ser
1               5                   10                  15

<210> SEQ ID NO 84
<211> LENGTH: 20
<212> TYPE: PRT
```

<213> ORGANISM: Artificial Sequence
<220> FEATURE:
<223> OTHER INFORMATION: Linker

<400> SEQUENCE: 84

Gly Gly Gly Ser Gly Gly Gly Ser Gly Gly Gly Ser Gly Gly Gly Ser
1               5                   10                  15

Gly Gly Gly Ser
            20

<210> SEQ ID NO 85
<211> LENGTH: 451
<212> TYPE: PRT
<213> ORGANISM: Artificial Sequence
<220> FEATURE:
<223> OTHER INFORMATION: IgG hybrid

<400> SEQUENCE: 85

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Ser Gly Tyr Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Ser Tyr Tyr Gly Tyr Tyr Tyr Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Arg Lys Cys Cys
    210                 215                 220

Val Glu Cys Pro Pro Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

```
Arg Val Val Ser Val Leu Thr Val Leu His Gln Asp Trp Leu Asn Gly
305             310             315             320

Lys Glu Tyr Lys Cys Lys Val Ser Asn Lys Ala Leu Pro Ala Pro Ile
                325             330             335

Glu Lys Thr Ile Ser Lys Ala Lys Gly Gln Pro Arg Glu Pro Gln Val
            340             345             350

Tyr Thr Leu Pro Pro Ser Arg Asp Glu Leu Thr Lys Asn Gln Val Ser
        355             360             365

Leu Thr Cys Leu Val Lys Gly Phe Tyr Pro Ser Asp Ile Ala Val Glu
        370             375             380

Trp Glu Ser Asn Gly Gln Pro Glu Asn Asn Tyr Lys Thr Thr Pro Pro
385             390             395             400

Val Leu Asp Ser Asp Gly Ser Phe Phe Leu Tyr Ser Lys Leu Thr Val
            405             410             415

Asp Lys Ser Arg Trp Gln Gln Gly Asn Val Phe Ser Cys Ser Val Met
            420             425             430

His Glu Ala Leu His Asn His Tyr Thr Gln Lys Ser Leu Ser Leu Ser
        435             440             445

Pro Gly Lys
    450

<210> SEQ ID NO 86
<211> LENGTH: 451
<212> TYPE: PRT
<213> ORGANISM: Artificial Sequence
<220> FEATURE:
<223> OTHER INFORMATION: IgG1

<400> SEQUENCE: 86

Glu Val Gln Leu Leu Glu Ser Gly Gly Gly Leu Val Gln Pro Gly Gly
1               5               10              15

Ser Leu Arg Leu Ser Cys Ala Ala Ser Gly Phe Thr Phe Ser Ser Tyr
            20              25              30

Ala Met Ser Trp Val Arg Gln Ala Pro Gly Lys Gly Leu Glu Trp Val
        35              40              45

Ser Gly Ile Ser Gly Tyr Ser Gly Ser Thr Tyr Tyr Ala Asp Ser Val
    50              55              60

Lys Gly Arg Phe Thr Ile Ser Arg Asp Asn Ser Lys Asn Thr Leu Tyr
65              70              75              80

Leu Gln Met Asn Ser Leu Arg Ala Glu Asp Thr Ala Val Tyr Tyr Cys
            85              90              95

Ala Arg Tyr Tyr Ser Tyr Tyr Gly Tyr Tyr Phe Asp Tyr Trp Gly
            100             105             110

Gln Gly Thr Leu Val Thr Val Ser Ser Ala Ser Thr Lys Gly Pro Ser
        115             120             125

Val Phe Pro Leu Ala Pro Ser Ser Lys Ser Thr Ser Gly Gly Thr Ala
    130             135             140

Ala Leu Gly Cys Leu Val Lys Asp Tyr Phe Pro Glu Pro Val Thr Val
145             150             155             160

Ser Trp Asn Ser Gly Ala Leu Thr Ser Gly Val His Thr Phe Pro Ala
            165             170             175

Val Leu Gln Ser Ser Gly Leu Tyr Ser Leu Ser Ser Val Val Thr Val
            180             185             190

Pro Ser Ser Ser Leu Gly Thr Gln Thr Tyr Ile Cys Asn Val Asn His
        195             200             205
```

-continued

```
Lys Pro Ser Asn Thr Lys Val Asp Lys Lys Val Glu Pro Lys Ser Cys
    210             215             220

Asp Lys Thr His Thr Cys Pro Pro Cys Pro Ala Pro Glu Leu Leu Gly
225             230             235             240

Gly Pro Ser Val Phe Leu Phe Pro Pro Lys Pro Lys Asp Thr Leu Met
            245             250             255

Ile Ser Arg Thr Pro Glu Val Thr Cys Val Val Val Asp Val Ser His
            260             265             270

Glu Asp Pro Glu Val Lys Phe Asn Trp Tyr Val Asp Gly Val Glu Val
            275             280             285

His Asn Ala Lys Thr Lys Pro Arg Glu Glu Gln Tyr Asn Ser Thr Tyr
    290             295             300

Arg Val Val Ser Val Leu Thr Val Leu His Gln Asp Trp Leu Asn Gly
305             310             315             320

Lys Glu Tyr Lys Cys Lys Val Ser Asn Lys Ala Leu Pro Ala Pro Ile
            325             330             335

Glu Lys Thr Ile Ser Lys Ala Lys Gly Gln Pro Arg Glu Pro Gln Val
            340             345             350

Tyr Thr Leu Pro Pro Ser Arg Asp Glu Leu Thr Lys Asn Gln Val Ser
            355             360             365

Leu Thr Cys Leu Val Lys Gly Phe Tyr Pro Ser Asp Ile Ala Val Glu
    370             375             380

Trp Glu Ser Asn Gly Gln Pro Glu Asn Asn Tyr Lys Thr Thr Pro Pro
385             390             395             400

Val Leu Asp Ser Asp Gly Ser Phe Phe Leu Tyr Ser Lys Leu Thr Val
            405             410             415

Asp Lys Ser Arg Trp Gln Gln Gly Asn Val Phe Ser Cys Ser Val Met
            420             425             430

His Glu Ala Leu His Asn His Tyr Thr Gln Lys Ser Leu Ser Leu Ser
            435             440             445

Pro Gly Lys
    450

<210> SEQ ID NO 87
<211> LENGTH: 16
<212> TYPE: PRT
<213> ORGANISM: Artificial Sequence
<220> FEATURE:
<223> OTHER INFORMATION: UU-44

<400> SEQUENCE: 87

Ala Gly Ile Leu Ala Arg Asn Leu Val Pro Met Val Ala Thr Val Gln
1               5               10              15
```

CD40 BINDING PROTEIN, BISPECIFIC CONJUGATE THEREOF AND METHOD OF TREATING CANCER

CROSS-REFERENCE TO RELATED APPLICATIONS

This application is a § 371 national phase of International Application No. PCT/EP2021/064390, filed on May 28, 2021, which claims the benefit of United Kingdom Application No. 2008003.2, filed on May 28, 2020, which applications are incorporated by reference herein.

INCORPORATION BY REFERENCE OF SEQUENCE LISTING PROVIDED AS A TEXT FILE

A Sequence Listing is provided herewith in a text file, AWAP-044_SequenceListing_PCT.txt, created on Nov. 1, 2022, and having a size of 84,124 bytes. The contents of the text file are incorporated herein by reference in its entirety.

FIELD

The present invention provides a binding protein that binds CD40 and is an agonist thereof. In a particular embodiment the invention provides an agonistic anti-CD40 antibody. Also provided are bispecific conjugates comprising the binding protein, and complexes comprising the bispecific conjugates non-covalently bound to a tag construct comprising an antigen, for antigen delivery to immune cells. Medical uses of the binding proteins, conjugates and complexes of the invention are also provided.

BACKGROUND

Monoclonal antibodies (mAbs) which modulate immune responses are proving highly effective in cancer treatment, with increasing evidence that such responses can be harnessed to provide durable eradication of tumours. Various antibodies against different targets have been developed, e.g. targeting the immune checkpoints CTLA-4 and PD-1, which support the view that T-cell immunity can provide an effective treatment for cancer. Promising clinical data have also been obtained with immunostimulatory mAbs that bind agonistically to the co-stimulatory receptor CD40 on antigen-presenting cells (APCs).

CD40 is a member of the TNF receptor superfamily (it is alternatively known as TNF receptor superfamily member 5; TNFRSF5) and is expressed on antigen-presenting cells (APCs) such as B-cells, dendritic cells (DCs), macrophages and monocytes, as well as epithelial and endothelial cells and certain tumour cells. When activated by its ligand (CD40 ligand; CD40L, also known as CD154), which is mainly expressed on mature T-cells, CD40 activates APCs and induces both innate and adaptive immune responses. Agonistic CD40 agents, such as anti-CD40 antibodies, can be used to induce the immune system to prevent proliferation of and/or kill cancer cells and thus provide an effective therapeutic treatment for cancer. In particular, APCs activated by an agonistic CD40 agent may stimulate T-cells, including effector T-cells, particularly CD8+ cytotoxic T-cells, leading to T-cell mediated destruction of cancer cells (e.g. tumours). There may also be direct cancer cell killing if the APC is a macrophage, and direct anti-tumour mechanisms may be observed for CD40-positive tumours, where the binding of anti-CD40 antibody to the tumour cell may induce apoptosis. In the context of a viral infection, T-cell activation may alternatively promote the killing of infected cells.

Various anti-CD40 antibodies are in pre-clinical or clinical development, including antibodies ADC-1013, CP-870, 893, Chi Lob 7/4, SEA-CD40 and APX005M. Antibody ADC-1013 is described in WO 2016/023960, and various other anti-CD40 antibodies are proposed for anti-cancer use in WO 2015/091853 and US 2017/0342159. ChiLob 7/4 is described in US 2009/0074711, SEA-CD40 is described in US 2017/0137528, CP-870,893 is described in US 2017/0342159 and APX005M (sometimes alternatively referred to simply as APX005) is described in WO 2014/070934.

The present application provides a further agonistic antibody (or related binding protein) against CD40. The binding protein has been shown to bind CD40 with a high affinity and to display strong agonistic activity, and may thus be used as a stand-alone cancer therapeutic, as described above. The binding protein is also particularly suited to use in the context of a therapeutic bispecific conjugate, which may similarly be used for cancer therapy or, alternatively, for treatment of or vaccination against an infection.

Effective stimulation (or priming) of T-cells requires not only application of a CD40 stimulus to an APC, but also the presentation of antigen by the APC (in the context of an MHC) for recognition and binding by a T-cell receptor (TCR). Thus, it is advantageous for the APC to cross-present antigen to T-cells for the purpose of T-cell stimulation, in other words to take up, process and present antigen (of extracellular origin) to the T-cells. However, antigenic material may not always be present (for example if a tumour has been resected, or in the context of a vaccine against an infection), and CD40 agonists may have poor efficacy in driving effective T-cell stimulation in such a situation. CD40 stimulation may also be insufficient for T-cell activation (for example if there is a dose-limiting toxicity of the CD40 agonist as an infusion product).

For these reasons, it is advantageous to deliver antigen to the APC at the same time as activating CD40 on the APC surface with an agonist. Bispecific conjugates for this purpose are described in WO 2020/104690. The bispecific conjugates described therein comprise two binding proteins covalently coupled together. The first binding protein is specific for CD40; the second binding protein, rather than being directly specific for an antigen, is instead specific for a tag. A tag construct is provided in which the tag is covalently coupled to an antigen, and forms a complex with the bispecific conjugate. Hence, by binding to the tag, the second binding protein is bound indirectly to the antigen, providing a flexible, modular approach by which the antigen can be varied, since there is no chemical linkage between the antigen and the antibody.

WO 2020/104690 thus provides a complex formed between the bispecific conjugate and the tag construct, which complex provides both a CD40 agonist (for activation of an APC) and an antigen (for presentation by the APC). This ensures that APC activation by the CD40 agonist leads to activation of T cells specific for the target antigen, and advantageously allows for flexibility in preparing conjugates and complexes for use in personalised medicine, as well as the use of this flexible platform for vaccine development for vaccination of individuals using the CD40-pathway to mount an effective anti-pathogen immune response.

The complex of WO 2020/104690 can also stimulate B cell responses against an antigen. The complex can form two interactions with a B cell: the anti-CD40 binding protein can bind CD40 on the surface of a B cell and the antigen in the tag construct can bind a specific B cell receptor. The combination of these two interactions activates B cells which recognise the antigen. Indeed, B cells activated in this manner using complexes as described in WO 2020/104690 may not require co-stimulation by helper T cells for full activation.

Rather than preparing conjugates comprising an antigen directly fused to a CD40 agonist, or an antigen-specific binder fused to the agonist, which would require the laborious synthesis and production of a separate conjugate for each patient (or at least each different tumour antigen) or for each pathogenic serotype, the bi-specific conjugate can be tailored for individual, personalised use by binding to different tag constructs containing different antigens but the same tag, according to the need of a particular, individual, patient. The bispecific conjugate is by this strategy tailored to also adapt a personalised strategy to vaccinate against a pathogen with a high antigen drift ensuring a flexible vaccination strategy. In this way, only separate tag constructs need to be prepared, providing a benefit in the ease and costs of preparing patient/pathogen-specific therapeutic agents. It is further believed that the non-covalent binding of antigen to the CD40 agonist may be advantageous for the efficacy of the complex, as compared to a conjugate comprising antigen fused directly and covalently to the CD40 agonist, or as compared to providing the CD40 agonist and antigen separately.

The inventors have now discovered that not all agonistic CD40 antibodies are equally suitable for use in the bispecific conjugates of WO 2020/104690. It has been found that many agonistic CD40 antibodies have reduced agonistic activity when used in the context of such a bispecific conjugate. Without being bound by theory, it may be the case that retention of agonistic activity in the context of a bispecific conjugate is dependent on the location within CD40 of the epitope recognised by the antibody. It is hypothesised that antibodies which bind CD40 at a location distal to the membrane retain agonistic activity in the context of a bispecific conjugate, whereas antibodies which bind CD40 at a location proximal to the membrane lose activity in the context of a bispecific conjugate because the bulky second binding protein covalently attached to the anti-CD40 antibody sterically hinders its access to its epitope.

The CD40 binding protein of the present invention (often in the form of an antibody known as A9) has been found to bind CD40 at an epitope close to the N-terminus of CD40, distant from the membrane, and to retain a high level of agonistic activity when used in the context of a bispecific conjugate as described above. Thus the antibody of the invention may advantageously be used in the context of a bispecific conjugate.

SUMMARY OF INVENTION

Accordingly, in a first aspect the invention provides a binding protein that specifically binds CD40, wherein said binding protein is an agonist of CD40 and comprises a binding domain of an antibody, the binding domain comprising a heavy chain variable domain and a light chain variable domain, each comprising three complementarity determining domains (CDRs), wherein:

VLCDR1 has the sequence set forth in SEQ ID NO: 1;
VLCDR2 has the sequence AAS;
VLCDR3 has the sequence set forth in SEQ ID NO: 3;
VHCDR1 has the sequence set forth in SEQ ID NO: 4;
VHCDR2 has the sequence set forth in SEQ ID NO: 5; and
VHCDR3 has the sequence set forth in SEQ ID NO: 6.

In a second aspect, the invention provides a bispecific conjugate comprising:
(i) at least one first binding protein as defined in any one of claims 1 to 8; and
(ii) at least one second binding protein, which comprises a binding domain of an antibody and binds a peptide moiety;
wherein the first and second binding proteins are covalently linked.

In a third aspect, the invention provides a complex comprising a bispecific conjugate of the invention and a tag construct, the tag construct comprising a peptide moiety recognised by the second binding protein of the conjugate covalently attached to an antigen;
wherein the peptide moiety of said tag construct is non-covalently bound to the second binding protein of the bispecific conjugate.

In a fourth aspect, the invention provides a pharmaceutical composition comprising:
(i) a binding protein of the invention;
(ii) a bispecific conjugate of the invention; or
(iii) a complex of the invention;
and at least one pharmaceutically-acceptable carrier or excipient.

In a fifth aspect, the invention provides a product comprising a bispecific conjugate of the invention and a tag construct as defined above as a combined preparation for separate, simultaneous or sequential use in therapy.

In a sixth aspect, the invention provides a kit comprising a bispecific conjugate of the invention and a tag construct as defined above.

In a seventh aspect, the invention provides a binding protein of the invention, a bispecific conjugate of the invention, a complex of the invention, a composition of the invention or a kit of the invention, for use in therapy.

In an eighth aspect, the invention provides a binding protein of the invention, a bispecific conjugate of the invention, a complex of the invention, a composition of the invention or a kit of the invention, for use in the treatment or prevention of cancer.

Similarly, the invention provides a method of treating or preventing cancer, comprising administering to a subject a binding protein of the invention, a bispecific conjugate of the invention, a complex of the invention or a composition of the invention.

Also provided is the use of a binding protein of the invention, a bispecific conjugate of the invention or a complex of the invention in the manufacture of a medicament for the treatment or prevention of cancer.

In a ninth aspect, the invention provides a binding protein of the invention, a bispecific conjugate of the invention, a complex of the invention, a composition of the invention or a kit of the invention, for use in the treatment or prevention of an infection.

Similarly, the invention provides a method of treating or preventing an infection, comprising administering to a subject a binding protein of the invention, a bispecific conjugate of the invention, a complex of the invention or a composition of the invention.

Also provided is the use of a binding protein of the invention, a bispecific conjugate of the invention or a complex of the invention in the manufacture of a medicament for the treatment or prevention of an infection.

In a tenth aspect, the invention provides a nucleic acid molecule comprising a nucleotide sequence encoding a binding protein of the invention.

In an eleventh aspect, the invention provides a recombinant construct comprising a nucleic acid molecule of the invention.

In a twelfth aspect, the invention provides a vector comprising a nucleic acid molecule of the invention or a recombinant construct of the invention.

In a thirteenth aspect, the invention provides a cell comprising a nucleic acid molecule of the invention, a recombinant construct of the invention or a vector of the invention.

In a fourteenth aspect, the invention provides an in vitro or ex vivo method of activating a T-cell expressing a TCR which recognises an antigen, said method comprising contacting an antigen-presenting cell with:

i) a bispecific conjugate of the invention and a tag construct as defined above, wherein said tag construct comprises the antigen recognised by said TCR; or ii) a complex of the invention, wherein the tag construct of said complex comprises the antigen recognised by said TCR.

6 conjugates Bi-24, Bi-25 and Bi-26, as measured by ELISA. A range of antibody/conjugate concentrations was tested, as shown in the legend.

Figure 9A:
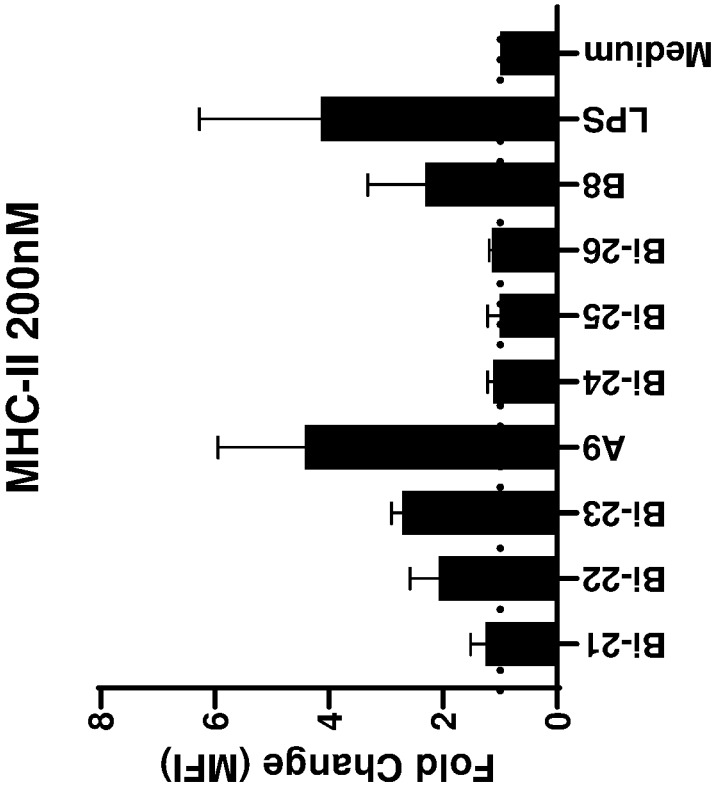
Figure 9B:
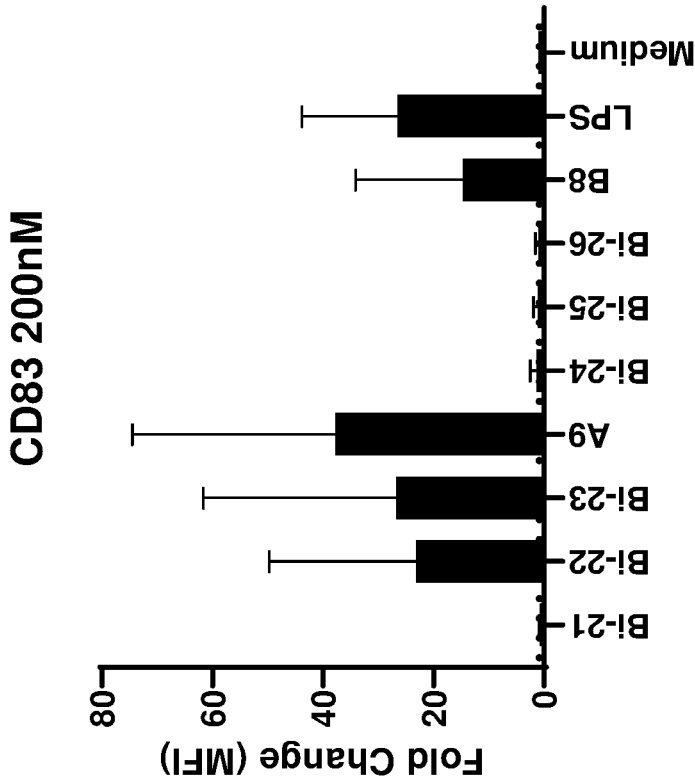

FIG. 9 shows the expression of the dendritic cell activation markers HLA-DR (denoted "MHC-II"; A), CD83 (B) and CD86 (C) as measured by flow cytometry, following dendritic cell stimulation with 200 nM A9 and B8 antibodies, Bi-21, Bi-22, Bi-23, Bi-24, Bi-25 and Bi-26 bispecific conjugates. LPS was used as a positive control. Fold change is defined in relation to the value for the negative control (medium).

Figure 10:
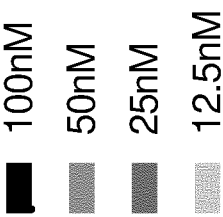
Figure 10:
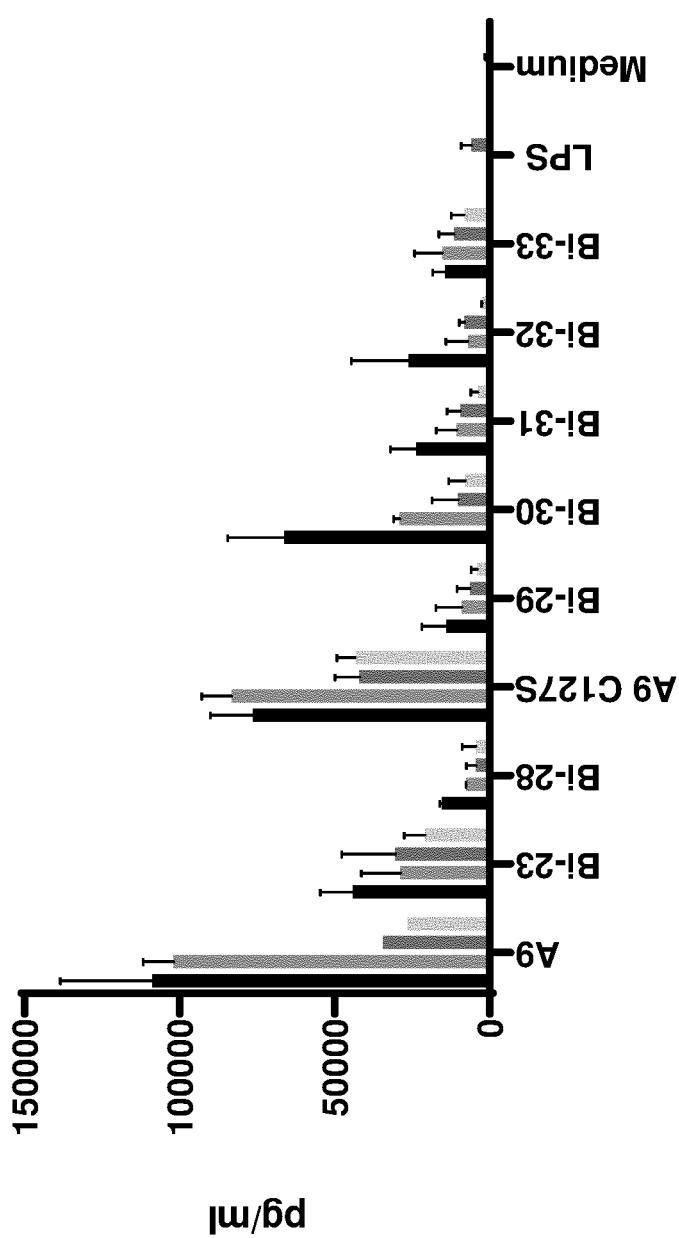

FIG. 10 shows IL-12 production in pg/ml (y axis) from dendritic cells stimulated with the anti-CD40 antibody A9 (as IgG2 or IgG2 C127S) and bispecific conjugates as indicated. LPS: Positive control. Medium: negative control.

Figure 11:
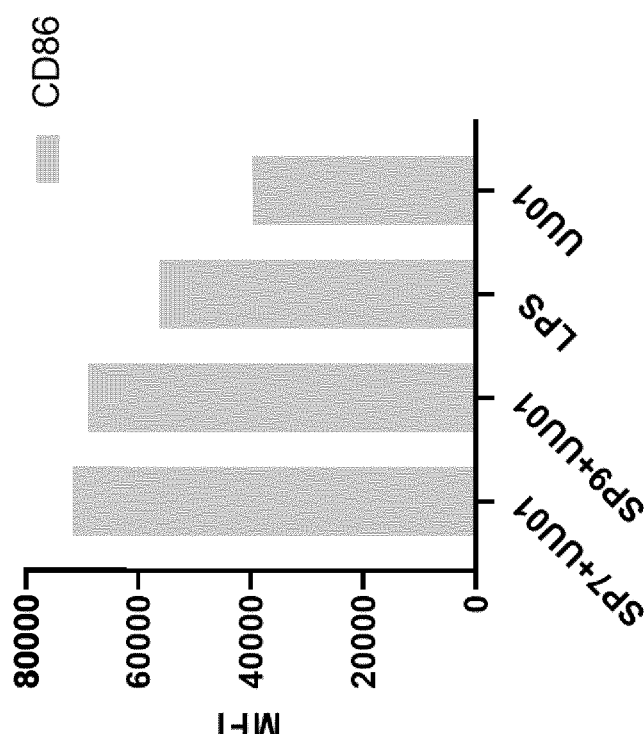
Figure 11:
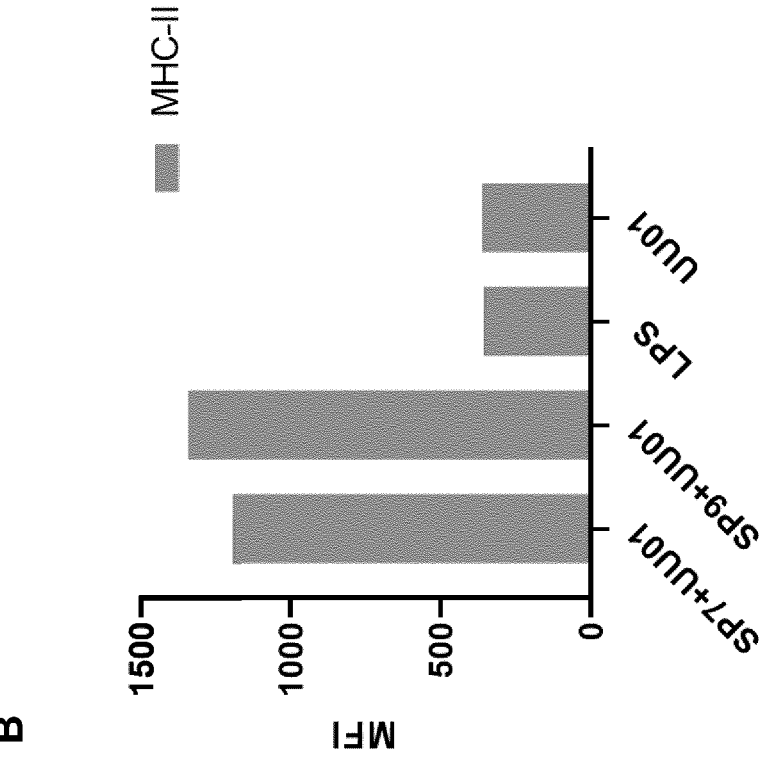

FIG. 11 shows the expression of the dendritic cell activation markers CD86 (A) and HLA-DR (denoted "MHC-II"; B), as measured by flow cytometry, following dendritic cell stimulation with constructs SP-7 and SP-9 in the presence of the tag peptide UU01 or peptide alone (negative control reference), as described in Example 15. LPS was used as a positive control.

Figure 12:
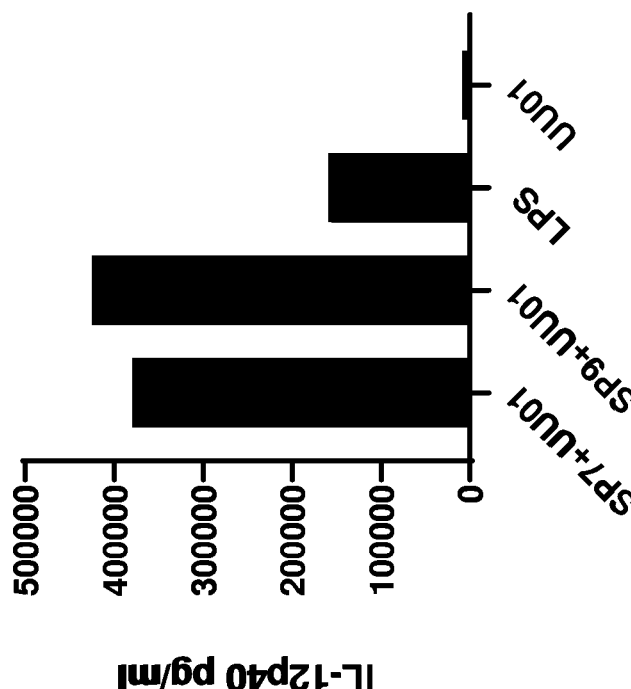

FIG. 12 shows IL-12 production from dendritic cells stimulated with constructs SP-7 and SP-9 in complex with tag peptide UU01 or peptide alone, as described in Example 15. LPS was used as a positive control.

Figure 13:
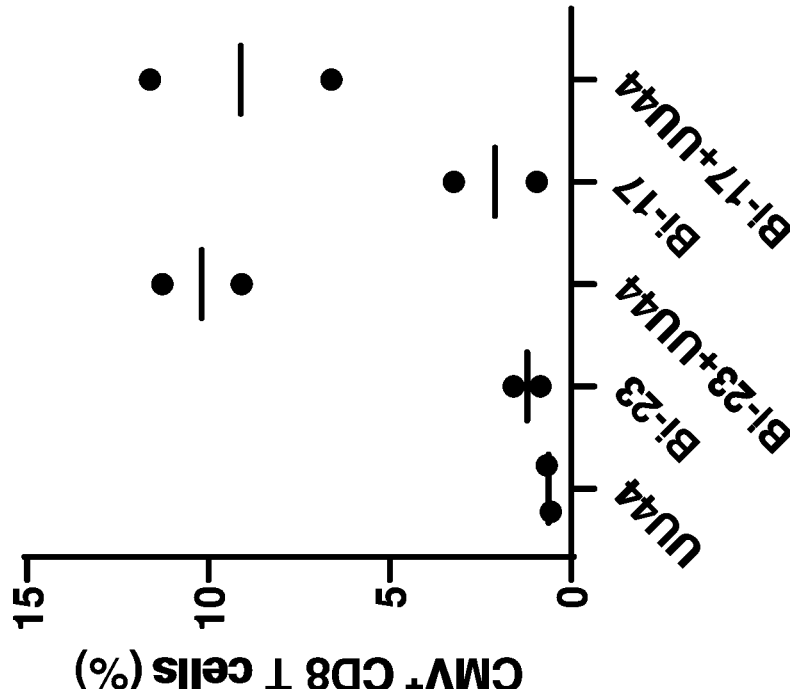

FIG. 13 shows expansion of CMV specific CD8+ T cells as described in Example 16, with MoDC:s stimulated with either of the two bispecific conjugates alone ("Bi-23" and "Bi-17", respectively) or in complex with the peptide UU44 ("Bi-23+UU44" and "Bi-17+UU44", respectively) or with the UU44 peptide alone.

Figure 14:
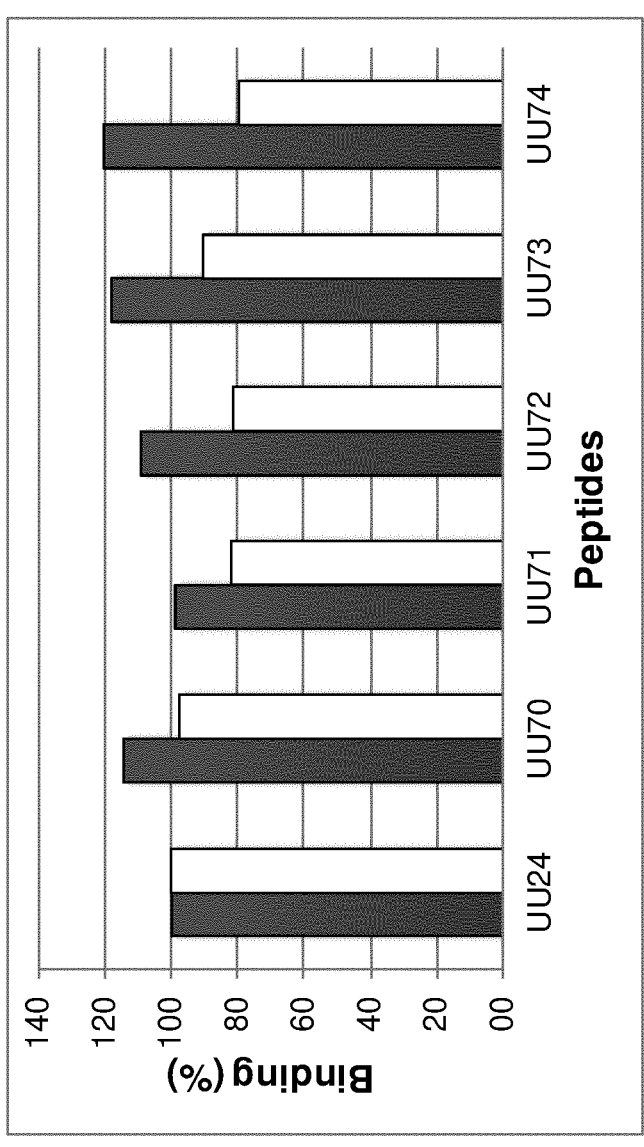

FIG. 14 shows the normalised binding response of the scFvs IBIIICI (grey bars) and 14GIIICII (white bars) to various shortened MTTE peptides, as measured by SPR. The binding response values are normalised to the signal obtained for binding of the scFvs to peptide UU24. The values have also been normalised for differences in scFv capture levels and target peptide molecular weights. The binding response for each sample was taken at the start of the dissociation phase.

DETAILED DESCRIPTION OF INVENTION

As is known to the skilled person, antibodies are proteins which comprise four polypeptide chains: two heavy chains and two light chains. Typically, the heavy chains are identical to each other and the light chains are identical to each other. The light chains are shorter (and thus lighter) than the heavy chains. The heavy chains comprise four or five domains: at the N-terminus a variable ($V_H$) domain is located, followed by three or four constant domains (from N-terminus to C-terminus $C_H1$, $C_H2$, $C_H3$ and, where present, $C_H4$, respectively). The light chains comprise two domains: at the N-terminus a variable ($V_L$) domain is located and at the C-terminus a constant ($C_L$) domain is located. In the heavy chain an unstructured hinge region is located between the $C_H1$ and $C_H2$ domains. The two heavy chains of an antibody are joined by disulphide bonds formed between cysteine residues present in the hinge region, and each heavy chain is joined to one light chain by a disulphide bond between cysteine residues present in the $C_H1$ and $C_L$ domains, respectively.

In mammals two types of light chain are produced, known as lambda (λ) and kappa (κ). For kappa light chains, the variable and constant domains can be referred to as Vκ and Cκ domains, respectively. Whether a light chain is a λ or κ light chain is determined by its constant region: the constant regions of λ and κ light chains differ, but are the same in all light chains of the same type in any given species.

The constant regions of the heavy chains are the same in all antibodies of any given isotype in a species, but differ between isotypes (examples of antibody isotypes are classes IgG, IgE, IgM, IgA and IgD; there are also a number of antibody sub-types, e.g. there are four sub-types of IgG antibodies: IgG1, IgG2, IgG3 and IgG4). The specificity of an antibody is determined by the sequence of its variable region. The sequence of variable regions varies between antibodies of the same type in any individual. In particular, both the light and heavy chains of an antibody comprise three hypervariable complementarity-determining regions (CDRs). In a pair of a light chain and a heavy chain, the CDRs of the two chains form the antigen-binding site. The CDR sequences determine the specificity of an antibody. A pair of a light chain variable region and a heavy chain variable region, comprising an (antigen) binding site, is known as an (antigen) binding domain.

The three CDRs of a heavy chain are known as VHCDR1, VHCDR2 and VHCDR3, from N-terminus to C-terminus, and the three CDRs of a light chain are known as VLCDR1, VLCDR2 and VLCDR3, from N-terminus to C-terminus.

The present invention provides a new binding protein that specifically binds CD40, and is an agonist of CD40. The term "binding protein" is used herein to denote a binding protein comprising a binding domain of an antibody (that is to say, a binding domain obtained or derived from an antibody, or based on a binding domain of an antibody). Thus, the binding protein is an antibody-based, or antibody-like, molecule comprising the binding site of, or a binding site derived from, an antibody. It is thus an immunological binding agent.

As noted above, a binding domain of an antibody is composed of a light chain variable domain and a heavy chain variable domain (thus a classical bivalent antibody has two binding domains). A binding protein may thus be a native antibody or a fragment thereof, or an artificial or synthetic antibody, or an antibody construct, or derivative (e.g. a single chain antibody, as discussed further below). In summary, the binding protein of the invention comprises a binding domain of an antibody, said binding domain of an antibody comprising a light chain variable domain and a heavy chain variable domain.

The binding protein of the present invention specifically binds CD40. By "specifically" it is meant that the binding protein binds to its target (i.e. CD40) in a manner that can be distinguished from binding to non-target molecules, more particularly that the binding protein binds its target (CD40) with greater binding affinity than with which it binds other molecules. That is, the binding protein does not bind to other, non-target, molecules, or does not do so to an appreciable or significant degree, or binds with lower affinity to such other molecules than with which it binds CD40. A binding protein "that specifically binds" CD40 may alternatively be referred to as "directed against" or "that recognises" CD40. In other words, CD40 is the antigen of the binding protein of the present invention, and the binding protein is thus an "antigen binding protein" in the sense that it binds CD40 as its antigen.

The term "CD40" refers to CD40 from any species. Thus, it may be human CD40 or its equivalent or corresponding molecule in other species, most notably other mammals. Preferably the CD40 is human CD40, such that the binding protein of the invention specifically binds, and is an agonist of, human CD40. Human CD40 has the UniProt accession number P25942, and the amino acid sequence shown in SEQ ID NO: 17. In particular, the first binding protein of the invention binds to CD40 (particularly human CD40) in its native state, i.e. when expressed on the surface of cell.

The binding protein of the invention is an agonist of CD40. That is, the molecule is capable of agonising, or activating, CD40 (i.e. when the binding protein of the invention binds CD40, it activates it). This means that the binding protein of the invention is capable of enhancing CD40 signalling. The binding protein can thus increase the activity of (i.e. activate or stimulate) a cell expressing CD40, notably an APC expressing CD40, such as a dendritic cell, or a B cell, macrophage, monocyte or any myeloid cell. The cell may be CD11 b-positive or CD11c-positive. In a particular embodiment, the binding protein is capable of activating DCs.

Professional APCs, such as DCs, are activated when signalling via CD40 occurs, which triggers several biological events, including immune cell activation, proliferation, and production of cytokines and chemokines. Methods for determining DC, or other APC, activation by CD40 are known in the art (see for example Schonbeck et al. 2001, Cell Mol Life Sci., 58:40-43, and WO 2015/091853 and US 2017/0342159) and are described in the Examples below.

It is also known and reported in the art how to determine the ability of a specific anti-CD40 binding molecule to modulate (or increase) the activity of an APC such as a DC, for example by measuring the level of cell-surface markers such as CD86 and CD80, measuring cytokine release (e.g. IL-12 release by DC), and/or by measuring anti-CD40 binding molecule-induced T-cell activity (e.g. secretion of IFN-γ). An in vitro DC activation assay is described in the Examples below, and utilises IL-12 release as an activation marker.

As is well known in the art, CD40 is a cell surface protein. Upon engagement by a ligand or agonist, CD40 may be internalised. TNFR internalisation can be a way of regulating immune activation. Antibodies to CD40 may have different internalisation properties. Internalisation of CD40 following antibody binding will lead to antibody internalisation, and therefore any cargo linked (non-covalently or covalently) to that antibody can be taken up by a cell via CD40-mediated antibody uptake. The CD40 receptor can then recycle back to the cell surface and without being bound by theory, it is possible that CD40 internalisation and recycling can affect the agonistic activity of an anti-CD40 antibody. For the current invention, it is preferred that the binding protein induces CD40 internalisation upon binding to CD40, followed by CD40 recycling to the cell surface where agonistic activation can be triggered by CD40 clustering on the surface. Antagonistic antibodies however may not induce recycling and thereby receptor (CD40) internalisation may hamper immune activation.

As detailed above, the specific binding molecule of the invention comprises six CDR sequences. The light and heavy chain variable domains comprise 3 CDRs each: the light chain variable domain comprises VLCDR1, VLCDR2 and VLCDR3, and the heavy chain variable domain comprises VHCDR1, VHCDR2 and VHCDR3. The six CDRs have the following amino acid sequences:

VLCDR1 has the sequence set forth in SEQ ID NO: 1;
VLCDR2 has the sequence AAS;
VLCDR3 has the sequence set forth in SEQ ID NO: 3;
VHCDR1 has the sequence set forth in SEQ ID NO: 4;
VHCDR2 has the sequence set forth in SEQ ID NO: 5; and
VHCDR3 has the sequence set forth in SEQ ID NO: 6.

The binding protein of the invention may be synthesised by any method known in the art. Preferably, the binding protein is synthesised using a protein expression system, such as a cellular expression system using prokaryotic (e.g. bacterial) cells or eukaryotic (e.g. yeast, fungus, insect or mammalian) cells. An alternative protein expression system is a cell-free, in vitro expression system, in which a nucleotide sequence encoding the binding protein is transcribed into mRNA, and the mRNA translated into a protein, in vitro. Cell-free expression system kits are widely available, and can be purchased from e.g. Thermo Fisher Scientific®. Alternatively, binding proteins may be chemically synthesised in a non-biological system. Liquid-phase synthesis or solid-phase synthesis may be used to generate polypeptides which may form or be comprised within the binding protein of the invention.

The skilled person can readily produce binding proteins using appropriate methodology common in the art. In particular, the binding protein may be recombinantly expressed in mammalian cells, such as CHO cells. A binding protein synthesised in a protein expression system may be purified using standard techniques in the art, e.g. it may be synthesised with an affinity tag and purified by affinity chromatography. If the binding protein is an antibody, it can be purified using affinity chromatography using one or more antibody-binding proteins, such as Protein G, Protein A, Protein A/G or Protein L.

As noted above, the binding protein is an antibody-based, or antibody-like, molecule. Thus a binding protein may be a native antibody or a fragment thereof, or an artificial or synthetic antibody, or an antibody construct or derivative (e.g. a single chain antibody).

In a preferred embodiment the binding protein is an antibody, in particular a monoclonal antibody. By "monoclonal antibody" is meant an antibody preparation consisting of a single antibody species, i.e. all antibodies in the preparation have the same amino acid sequences, including the same CDRs, and thus bind the same epitope on their target antigen (by "target antigen" is meant the antigen containing the epitope bound by a particular antibody, i.e. the target antigen of the binding protein of the invention is CD40) with the same effect. In other words, the antibody of the invention is preferably not part of a polyclonal mix of antibodies.

In an antibody, as described above, the CDR sequences are located in the variable domains of the heavy and light chains. The CDR sequences sit within a polypeptide framework, which positions the CDRs appropriately for antigen binding. Thus the remainder of the variable domains (i.e. the parts of the variable domain sequences which do not form a part of any one of the CDRs) constitute framework regions. The N-terminus of a mature variable domain forms framework region 1 (FR1); the polypeptide sequence between CDR1 and CDR2 forms FR2; the polypeptide sequence between CDR2 and CDR3 forms FR3; and the polypeptide sequence linking CDR3 to the constant domain forms FR4. In a binding protein of the invention the variable region framework regions may have any appropriate amino acid sequence such that the binding protein binds to CD40 via its CDRs.

If the binding protein is an antibody, the antibody may be of any isotype and sub-type. Thus it may be an IgA, IgD, IgE, IgG, or IgM antibody. The heavy-chain constant domains that correspond to the different isotypes of immunoglobulins are termed $\alpha$, $\delta$, $\epsilon$, $\gamma$ and $\mu$, respectively. The subunit structures and three-dimensional configurations of different isotypes of immunoglobulins are well known.

Preferably the antibody is an IgG antibody. As noted above, there are four sub-types of IgG antibody: IgG1, IgG2, IgG3 and IgG4. The IgG anti-CD40 antibody of the invention may be of any IgG sub-type, i.e. it may be an IgG1, IgG2, IgG3 or IgG4 antibody.

However, the present inventors have demonstrated that IgG antibodies of the IgG2 sub-type (i.e. IgG2 antibodies) have a particularly strong agonistic effect on CD40 and also induce effective CD40 internalisation and recycling. Binding of an agonistic IgG2 antibody to CD40 is particularly effective in driving internalisation of CD40 (and the cargo attached to it). Importantly, agonistic IgG2 antibodies are more effective at driving CD40 internalisation, and thereby stimulating T-cell activation against the attached peptide cargo molecules, than IgG1 antibodies, as demonstrated in WO 2020/104690. This means that an IgG2 antibody generally has a higher agonistic effect than an IgG1 antibody with the same variable domain, as shown in the present Examples. Accordingly, in one embodiment, the binding protein of the invention is an IgG2 antibody (in particular an IgG2 monoclonal antibody). However, in another embodiment, the binding protein is an IgG1 antibody. In yet another embodiment, the binding protein has a constant region that is a hybrid between IgG1 and IgG2, such as a hybrid constant region in which the hinge region is of the IgG2 subtype while the remaining parts of the constant region are of the IgG1 subtype.

As detailed above, antibody light chains belong to either the kappa ($\kappa$) and lambda (A) types. The binding protein of the present invention may contain $\kappa$ or $\lambda$ light chains. In a particular embodiment the binding protein of the present invention comprises a $\kappa$ light chain.

Alternatively, the binding protein may be a binding fragment of an antibody (i.e. an antibody fragment), that is a fragment which retains the ability of the antibody to bind specifically to CD40. Such fragments are well known and examples include Fab', Fab, F(ab')$_2$, Fv, Fd, or dAb fragments, which may be prepared according to techniques well known in the art.

A Fab fragment consists of the antigen binding domain of an antibody, i.e. an individual antibody may be seen to contain two Fab fragments, each consisting of a light chain and its conjoined N-terminal section of a heavy chain. Thus a Fab fragment contains an entire light chain and the $V_H$ and $C_H1$ domains of the heavy chain to which it is bound. Fab fragments may be obtained by digesting an antibody with papain.

F(ab')$_2$ fragments consist of the two Fab fragments of an antibody, plus the hinge regions of the heavy domains, including the disulphide bonds linking the two heavy chains together. In other words, a F(ab')$_2$ fragment can be seen as two covalently joined Fab fragments. F(ab')$_2$ fragments may be obtained by digesting an antibody with pepsin. Reduction of F(ab')$_2$ fragments yields two Fab' fragments, which can be seen as Fab fragments containing an additional sulfhydryl group which can be useful for conjugation of the fragment to other molecules.

Alternatively, the binding protein may be a synthetic or artificial construct, i.e. an antibody-like molecule which comprises a binding domain, but which is genetically engineered or artificially constructed. This includes chimeric or CDR-grafted antibodies, as well as single chain antibodies and other constructs, e.g. scFv, dsFv, ds-scFv, dimers, mini-bodies, diabodies, single domain antibodies (DABs), Tand-Abs dimers and heavy chain antibodies such as $V_HH$, etc. In a particular embodiment the artificial construct is a single chain variable fragment (scFv). An scFv is a fusion protein in which a single polypeptide comprises both the $V_H$ and $V_L$ domains of an antibody. scFv fragments generally include a peptide linker covalently joining the $V_H$ and $V_L$ regions, which contributes to the stability of the molecule. The linker may comprise from 1 to 20 amino acids, such as for example 1, 2, 3 or 4 amino acids, 5, 10 or 15 amino acids, or other intermediate numbers in the range 1 to 20 as convenient. The peptide linker may be formed from any generally convenient amino acid residues, such as glycine and/or serine. One example of a suitable linker is Gly$_4$Ser (SEQ ID NO: 21). Multimers of such linkers may be used, such as for example a dimer, a trimer, a tetramer or a pentamer, e.g. (Gly$_4$Ser)$_2$ (SEQ ID NO: 22), (Gly$_4$Ser)$_3$ (SEQ ID NO: 82), (Gly$_4$Ser)$_4$ (SEQ ID NO: 83) or (Gly$_4$Ser)$_5$ (SEQ ID NO: 84). However, it is not essential that a linker be present, and the $V_L$ domain may be linked to the $V_H$ domain by a peptide bond. An scFv typically comprises, N-terminal to C-terminal, a $V_H$ region linked to a $V_L$ region by a linker sequence. The preparation of scFv molecules is well known in the art.

In a preferred embodiment, the binding protein is a human protein, in particular a human monoclonal antibody, antibody fragment or scFv. A human binding protein may comprise $V_H$ and $V_L$ regions in which both framework and CDR regions are derived from human germline immunoglobulin sequences, and also a human constant region, if a constant region is contained in the protein. Such proteins may however include amino acids not encoded by human germline Ig sequences, for example mutations introduced by random or site-specific mutagenesis.

As detailed above, the binding protein of the invention comprises a binding domain of an antibody, the binding domain comprising a heavy chain variable domain (or variable region) and a light chain variable domain. In a particular embodiment, the binding protein comprises the heavy and light chain variable domains of the A9 antibody, or variants thereof. The A9 antibody has a light chain with a variable domain with the amino acid sequence set forth in SEQ ID NO: 7, and a heavy chain with a variable domain with the amino acid sequence set forth in SEQ ID NO: 8. Thus in a particular embodiment the binding protein of the invention comprises:

(i) a light chain variable domain comprising (or consisting of) the amino acid sequence set forth in SEQ ID NO: 7, or a variant thereof; and (ii) a heavy chain variable domain comprising (or consisting of) the amino acid sequence set forth in SEQ ID NO: 8, or a variant thereof.

In the present disclosure, a variant of SEQ ID NO: 7 is defined as an amino acid sequence having at least 80% sequence identity to SEQ ID NO: 7, e.g. at least 80%, 85%, 90% or 95% sequence identity to SEQ ID NO: 7. This is of course with the proviso that the CDR sequences of the variant of SEQ ID NO: 7 are unaltered relative to the native VLCDR1, VLCDR2 and VLCDR3 sequences of the A9 antibody, set out in SEQ ID NO: 1, the amino acid sequence AAS, and SEQ ID NO: 3. Similarly, a variant of SEQ ID NO: 8 is defined as an amino acid sequence having at least 80% sequence identity to SEQ ID NO: 8, e.g. at least 80%, 85%, 90% or 95% sequence identity to SEQ ID NO: 8. This is of course with the proviso that the CDR sequences of the variant of SEQ ID NO: 8 are unaltered relative to the native VHCDR1, VHCDR2 and VHCDR3 sequences of the A9 antibody, set out in SEQ ID NOs: 4-6.

As noted above, in a preferred embodiment of the invention the binding protein is a monoclonal antibody. The monoclonal antibody may have a light chain with a variable region comprising the amino acid sequence set forth in a SEQ ID NO: 7, or a variant thereof, and a heavy chain with a variable region comprising the amino acid sequence set forth in SEQ ID NO: 8, or a variant thereof.

As noted above, the monoclonal antibody is preferably human, and while the monoclonal antibody may be of any isotype, it is preferred that it is an IgG antibody, for example selected from IgG1 antibodies, IgG2 antibodies and antibodies with a hybrid IgG1/2 constant region, most preferably an IgG2 antibody.

The human IgG2 constant region sequence is set forth in SEQ ID NO: 18 (UniProt accession number P01859). The full length A9 heavy chain sequence is set forth in SEQ ID NO: 10 and comprises a variable region of SEQ ID NO: 8 and a constant region of SEQ ID NO: 18. The full length A9 light chain sequence is a κ light chain with the amino acid sequence set forth in SEQ ID NO: 9, and comprises a variable region of SEQ ID NO: 7 and a constant region of SEQ ID NO: 19 (the human K light chain constant region, UniProt accession number P01834).

In an embodiment of the invention the binding protein is a monoclonal antibody comprising (or consisting of):

(i) a light chain comprising (or consisting of):
   (a) a variable domain comprising (or consisting of) the amino acid sequence set forth in SEQ ID NO: 7, or a variant thereof; and
   (b) a constant domain comprising (or consisting of) the amino acid sequence set forth in SEQ ID NO: 19, or a variant thereof; and (ii) a heavy chain comprising (or consisting of):
   (a) a variable domain comprising (or consisting of) the amino acid sequence set forth in SEQ ID NO: 8, or a variant thereof; and
   (b) a constant domain comprising (or consisting of) the amino acid sequence set forth in SEQ ID NO: 18, or a variant thereof.

Variants of SEQ ID NOs: 7 and 8 are defined above. In the present disclosure, a variant of SEQ ID NO: 19 is defined as an amino acid sequence having at least 80% sequence identity to SEQ ID NO: 19, e.g. at least 80%, 85%, 90% or 95% sequence identity to SEQ ID NO: 19. Similarly, a variant of SEQ ID NO: 18 is defined as an amino acid sequence having at least 80% sequence identity to SEQ ID NO: 18, e.g. at least 80%, 85%, 90% or 95% sequence identity to SEQ ID NO: 18.

Variants of the native IgG2 constant region are known which, for example, alter or affect the properties of an antibody or antibody construct containing the modified (mutated) constant region. One such variant (or mutant) IgG2 constant region is IgG2 C127S, the use of which is demonstrated in WO 2020/104690. This mutant is locked in to the IgG2B conformation, which has been found to enhance the ability of IgG2 antibodies to initiate immune responses. The amino acid sequence of the IgG2 C127S variant is presented in SEQ ID NO: 20. As will be apparent from comparison of the sequences, the cysteine residue at position 14 of the native IgG2 constant sequence (set forth in SEQ ID NO: 18) is substituted for serine in the C127S variant (set forth in SEQ ID NO: 20). The IgG2 C127S constant region may be used in the binding protein of the invention. It was recently shown by Yu et al (Cancer Cell 37(6):850-866, 2020) that the IgG2 format can turn an antagonistic CD40 antibody into a super agonistic antibody, an effect dependent on the IgG2B hinge-CH1 region.

Thus in another embodiment of the invention the binding protein is a monoclonal antibody comprising (or consisting of):

(i) a light chain comprising (or consisting of):
   (a) a variable domain comprising (or consisting of) the amino acid sequence set forth in SEQ ID NO: 7, or a variant thereof; and (b) a constant domain comprising (or consisting of) the amino acid sequence set forth in SEQ ID NO: 19, or a variant thereof; and (ii) a heavy chain comprising (or consisting of):

(a) a variable domain comprising (or consisting of) the amino acid sequence set forth in SEQ ID NO: 8, or a variant thereof; and (b) a constant domain comprising (or consisting of) the amino acid sequence set forth in SEQ ID NO: 20.

Similarly, an IgG1 constant region may also be used in the binding protein of the invention, and is shown in the Examples that follow to have agonistic activity. Thus, in another embodiment of the invention the binding protein is a monoclonal antibody comprising (or consisting of):

(i) a light chain comprising (or consisting of):

(a) a variable domain comprising (or consisting of) the amino acid sequence set forth in SEQ ID NO: 7, or a variant thereof; and (b) a constant domain comprising (or consisting of) the amino acid sequence set forth in SEQ ID NO: 19, or a variant thereof; and (ii) a heavy chain comprising (or consisting of):

(a) a variable domain comprising (or consisting of) the amino acid sequence set forth in SEQ ID NO: 8, or a variant thereof; and (b) a constant domain comprising (or consisting of) the amino acid sequence set forth in SEQ ID NO: 78.

Similarly, a constant region which is a hybrid between subclasses IgG1 and IgG2 may also be used in the binding protein of the invention, and is shown in the Examples that follow to have agonistic activity. Thus, in another embodiment of the invention the binding protein is a monoclonal antibody comprising (or consisting of):

(i) a light chain comprising (or consisting of):

(a) a variable domain comprising (or consisting of) the amino acid sequence set forth in SEQ ID NO: 7, or a variant thereof; and (b) a constant domain comprising (or consisting of) the amino acid sequence set forth in SEQ ID NO: 19, or a variant thereof; and (ii) a heavy chain comprising (or consisting of):

(a) a variable domain comprising (or consisting of) the amino acid sequence set forth in SEQ ID NO: 8, or a variant thereof; and (b) a constant domain comprising (or consisting of) the amino acid sequence set forth in SEQ ID NO: 77.

In a particular embodiment of the invention, the binding protein is a monoclonal antibody comprising (or consisting of):

(i) a light chain comprising (or consisting of) the amino acid sequence set forth in SEQ ID NO: 9, or a variant thereof; and (ii) a heavy chain comprising (or consisting of) the amino acid sequence set forth in SEQ ID NO: 10, or a variant thereof.

In a particular embodiment, the binding protein is the A9 antibody, comprising a light chain of SEQ ID NO: 9 and a heavy chain of SEQ ID NO: 10.

In the present disclosure, a variant of SEQ ID NO: 9 is defined as an amino acid sequence having at least 80% sequence identity to SEQ ID NO: 9, e.g. at least 80%, 85%, 90% or 95% sequence identity to SEQ ID NO: 9. This is of course with the proviso that the CDR sequences of the variant of SEQ ID NO: 9 are unaltered relative to the native VLCDR1, VLCDR2 and VLCDR3 sequences of the A9 antibody, set out in SEQ ID NO: 1, the amino acids sequence AAS, and SEQ ID NO: 3. Similarly, a variant of SEQ ID NO: 10 is defined as an amino acid sequence having at least 80% sequence identity to SEQ ID NO: 10, e.g. at least 80%, 85%, 90% or 95% sequence identity to SEQ ID NO: 10. This is of course with the proviso that the CDR sequences of the variant of SEQ ID NO: 10 are unaltered relative to the native VHCDR1, VHCDR2 and VHCDR3 sequences of the A9 antibody, set out in SEQ ID NOs: 4-6.

An antibody heavy chain consisting of the A9 $V_H$ domain and the IgG2 C127S constant domain has the amino acid sequence set forth in SEQ ID NO: 74. Thus in a particular embodiment, the binding protein comprises a light chain of SEQ ID NO: 9 and a heavy chain of SEQ ID NO: 74.

An antibody heavy chain consisting of the A9 $V_H$ domain and the IgG1 constant domain has the amino acid sequence set forth in SEQ ID NO: 86. Thus in a particular embodiment, the binding protein comprises a light chain of SEQ ID NO: 9 and a heavy chain of SEQ ID NO: 86.

An antibody heavy chain consisting of the A9 $V_H$ domain and hybrid IgG1/IgG2 constant domain has the amino acid sequence set forth in SEQ ID NO: 85. Thus in a particular embodiment, the binding protein comprises a light chain of SEQ ID NO: 9 and a heavy chain of SEQ ID NO: 85.

Binding proteins with variants of the sequences of the A9 variable and/or constant domains are functional variants, having the activities described above (i.e. they specifically bind, and are agonists of, CD40, in particular human CD40). Variant sequences may be modified relative to the native A9 sequences by substitution, insertion and/or deletion of one or more amino acids.

An amino acid substitution relative to the native A9 sequence may be a conservative amino acid substitution. The term "conservative amino acid substitution", as used herein, refers to an amino acid substitution in which one amino acid residue is replaced with another amino acid residue having a similar side chain. Amino acids with similar side chains tend to have similar properties, and thus a conservative substitution of an amino acid important for the structure or function of a polypeptide may be expected to affect polypeptide structure/function less than a non-conservative amino acid substitution at the same position. Families of amino acid residues having similar side chains have been defined in the art, including basic side chains (e.g. lysine, arginine, histidine), acidic side chains (e.g. aspartic acid, glutamic acid), uncharged polar side chains (e.g. asparagine, glutamine, serine, threonine, tyrosine), non-polar side chains (e.g. glycine, cysteine, alanine, valine, leucine, isoleucine, proline, phenylalanine, methionine, tryptophan) and aromatic side chains (e.g. tyrosine, phenylalanine, tryptophan, histidine). Thus a conservative amino acid substitution may be considered to be a substitution in which a particular amino acid residue is substituted for a different amino acid in the same family. However, an amino acid substitution may equally be a non-conservative substitution, in which one amino acid is substituted for another with a side-chain belonging to a different family.

As detailed above, according to the present disclosure variants of native A9 sequences have at least 80% sequence identity to the native sequences. Sequence identity may be assessed by any convenient method. However, for determining the degree of sequence identity between sequences, computer programmes that make pairwise or multiple alignments of sequences are useful, for instance EMBOSS Needle or EMBOSS stretcher (both Rice, P. et al., Trends Genet., 16, (6) pp 276-277, 2000) may be used for pairwise sequence alignments while Clustal Omega (Sievers F et al., Mol. Syst. Biol. 7:539, 2011) or MUSCLE (Edgar, R. C., Nucleic Acids Res. 32(5):1792-1797, 2004) may be used for multiple sequence alignments, though any other appropriate programme may be used. Whether the alignment is pairwise or multiple, it must be performed globally (i.e. across the entirety of the reference sequence) rather than locally.

Sequence alignments and % identity calculations may be determined using for instance standard Clustal Omega parameters: matrix Gonnet, gap opening penalty 6, gap extension penalty 1. Alternatively the standard EMBOSS Needle parameters may be used: matrix BLOSUM62, gap opening penalty 10, gap extension penalty 0.5. Any other suitable parameters may alternatively be used.

For the purposes of this application, where there is dispute between sequence identity values obtained by different methods, the value obtained by global pairwise alignment using EMBOSS Needle with default parameters shall be considered valid.

As discussed above, a further aspect of the present invention is a bispecific conjugate comprising at least one first binding protein of the invention as described above; and at least one second binding protein which comprises a binding domain of an antibody and binds a peptide moiety;

wherein the first and second binding proteins are covalently linked.

As described above, the bispecific conjugate of the invention is a component of a modular system. The bispecific conjugate recognises (i.e. specifically binds) (1) CD40; and (2) a peptide moiety, also referred to as a peptide tag, or a tag moiety. As further described below, the peptide tag may be essentially any peptide or amino acid sequence. By combining the bispecific conjugate of the invention with a tag construct, comprising both a peptide moiety and an antigen, a vaccine complex is formed which can induce a specific immune response against the antigen. As detailed above, the vaccine complex both activates target antigen presenting cells (APCs), such as dendritic cells, by binding and agonising CD40 on their surface, and delivers the antigen to the interior of the APC following internalisation of the complex, resulting in presentation of the antigen and activation of T-cells which recognise the antigen.

The bispecific conjugate of the invention comprises at least one first binding protein and at least one second binding protein. As detailed above, the first and second binding proteins recognise different targets, and thus are different proteins. The bispecific conjugate, comprising at least one first and at least one second binding protein, may comprise two or more first and/or second binding proteins. In an embodiment the conjugate comprises one first binding protein and two or more, e.g. 2-4, second binding proteins. In such an embodiment the first binding protein may be bivalent, or it may have a valency of 2 or more. In such an embodiment the second binding protein may be monovalent.

Regardless, it is preferred for the conjugate to have more than one binding domain for each of its two targets, i.e. for each of CD40 and the tag moiety. In other words it is preferred for the conjugate to have a valency of at least 2 for each target. In this context, valency can be seen as equivalent to the number of binding domains that recognise a particular target. Accordingly, the first and/or second binding protein may each have more than one binding domain and/or the conjugate may comprise more than one first and/or second binding protein. A binding protein as used in the bispecific conjugate may thus be monovalent, or it may have a valency of two or more, i.e. it may comprise one, or two or more binding domains, for example 2-6, or 2-4 binding domains.

Furthermore, the bispecific conjugate may comprise one first or second binding protein, or it may comprise two or more first and/or second binding proteins, e.g. 2-6, or 2-4 first and/or second binding protein. In the case where a binding protein has a valency of more than one, in an embodiment the bispecific conjugate may comprise one of that binding protein, e.g. one first binding protein with a valency of 2 or more. In a case where a binding protein has a valency of one, in an embodiment the bispecific conjugate may comprise two or more of that binding protein, e.g. two or more monovalent second binding proteins, for example 2-4. It will be understood that in the case where there are multiple second binding proteins they will be specific for the same target peptide moiety. Where there are multiple first or second binding proteins in the conjugate, each first binding protein and each second binding protein will generally be the same, but can be different (e.g. each conjugate could contain a single, bivalent first binding protein which binds CD40, and two, different, monovalent second binding proteins, each of which binds a different tag moiety, or each of which is directed towards the same tag moiety, but e.g. binds to a different site therein or uses different CDRs to recognise the same epitope).

In one preferred embodiment the bispecific conjugate comprises one bivalent first binding protein, and two monovalent second binding proteins. As mentioned above, it is preferred that the two monovalent second binding proteins are identical. Thus, in such an embodiment the conjugate is tetravalent.

The term "binding affinity" refers to the ability of a binding molecule to bind, or not bind, its binding partner or target. Binding affinity may be quantified by determining the affinity constant ($K_d$) for a binding partner. Similarly, the specificity of binding of a binding molecule to its target may be defined in terms of the affinity constant of the binding molecule for its target compared to the affinity constant with respect to the binding molecule and a non-target molecule. Typically the $K_d$ of the binding molecule for its target will be at least 2-fold, preferably at least 5, 10, 15, 20, 30, 40, 50, 100 or 200-fold, less than its $K_d$ with respect to another non-target molecule. Binding affinities and dissociation constants may readily be determined using well known methods, as demonstrated in the Examples below. The first and second binding proteins may be capable of binding to their targets with an affinity that is at least 2, 5, 10, 50, 100 or 200-fold higher than their affinity for binding to another non-target molecule.

The first and second binding proteins may bind their respective targets with an affinity constant of 10, 5, 4, 3, 2 or 1 μM, or 1000 nM or less, but may exhibit higher affinity, for example having an affinity constant of about 900, 800, 700, 600, 500, 400, 300, 200, 150, 100, 90, 80, 70, 60, 50, 40, 30, 25, 20, 15, 10, 7, 5, 4, 3, 2, 1, 0.5, 0.2, 0.1, 0.05. 0.01 nM or less. Affinity can be determined using for example ELISA, isothermal titration calorimetry (ITC), surface plasmon resonance (e.g. BIAcore) or fluorescent polarisation assay. As demonstrated below, the A9 antibody binds human CD40 with an affinity constant of about 5 nM.

As mentioned above, the first binding protein of the bispecific conjugate of the invention is a binding protein of the first aspect of the invention, that specifically binds and agonises CD40. In a preferred embodiment, the first binding protein is a monoclonal antibody. As detailed above, the inventors have found that antibodies of the IgG2 isotype are particularly effective in driving internalisation of CD40 and the cargo attached to the receptor. The receptor can subsequently recirculate back to the cell surface. This is particularly important in the context of the bispecific conjugates of the invention, since when administered as a vaccine complex (as described above) internalisation of the conjugates with CD40 is required to internalise the tag construct, and thus for processing and presentation of the antigen. It is thus preferred that the first binding protein is a monoclonal antibody of the IgG2 isotype (or a variant thereof, such as the IgG2 C127S variant). In a particular and preferred embodiment, the first binding protein is the A9 antibody.

The second binding protein comprises a binding domain of an antibody. As described above, such domains are obtained or derived from an antibody, or based on an antigen binding domain of an antibody. Thus, the second binding protein is also an antibody-based, or antibody-like, molecule comprising the binding site of, or a binding site derived from, an antibody. Since it contains a binding domain, the second binding protein also comprises a heavy chain variable domain and a light chain variable domain, each comprising three CDRs.

The second binding protein may be any type of binding protein as set out above. However, in a certain particular embodiment it is a synthetic antibody construct, and in particular a single chain antibody. In a preferred embodiment the second binding protein is an scFv. Preferably, the first binding protein is a monoclonal antibody (most preferably of the IgG2 isotype) and the second binding protein is an scFv. In a particular embodiment, the bispecific conjugate comprises, as first binding protein, one monoclonal antibody; and as the second binding proteins, two scFvs.

The first and second binding proteins are covalently linked. As noted above, it is preferred that the second binding protein is a single chain antibody derivate (e.g. an scFv) and that the first binding protein is a monoclonal antibody. In this instance the second binding protein (scFv) may be covalently linked to a light or heavy chain of the first binding protein (monoclonal antibody). The second binding protein may be linked to either end of either chain of the monoclonal antibody, i.e. to the N- or C-terminus of the heavy or light chain of the monoclonal antibody. In a particular embodiment the second binding protein is linked to the C-terminal end of a heavy or light chain of a first binding protein (monoclonal antibody). Accordingly, the second binding protein may be linked to the constant region of the light chain ($C_L$) or to a constant domain of the constant region of the heavy chain (a $C_H$ domain), for example the $C_H3$ domain.

In a particular embodiment the first binding protein is a monoclonal antibody and the second binding protein is an scFv, and the scFv is covalently linked to either the $C_H3$ domain of the heavy chain of the antibody, or the $C_L$ domain of the light chain of the antibody. When the first binding protein is a monoclonal antibody and the second binding protein is an scFv, it is particularly preferred that the bispecific conjugate comprises one monoclonal antibody and two scFvs. In this case it is preferred that the two scFvs are conjugated to separate chains of the antibody (i.e. that the two scFvs are not conjugated to the same chain of the antibody). It is particularly preferred that the two scFvs are conjugated to corresponding chains of the antibody, i.e. that one scFv is conjugated to each of the two heavy chains of the antibody or that one scFv is conjugated to each of the two light chains of the antibody. However, this is not necessarily the case, i.e. one scFv may be conjugated to a heavy chain and one to a light chain.

It is particularly preferred that the two scFvs are conjugated to corresponding chains of the antibody at equivalent locations. In particular embodiments either (i) one scFv is conjugated to the $C_H3$ domain of each heavy chain of the antibody; or (ii) one scFv is conjugated to the $C_L$ domain of each light chain of the antibody.

As previously mentioned, it is alternatively possible for the second binding protein (e.g. an scFv) to be attached to the N-terminal end of the heavy or light chain of the monoclonal antibody which constitutes the first binding protein of the conjugate. In embodiments of the invention in which the first binding protein is a single chain antibody derivative, the second binding protein may be attached to the N- or C-terminus of the first binding protein. Conversely to the above, if the second binding protein comprises a heavy and a light chain and the first binding protein comprises only a single chain, the first binding protein may be attached to the N- or C-terminus of either the heavy or light chain of the second binding protein, equivalently to the description above.

Either end of the second binding protein may be joined to the first binding protein, e.g. the N- or C-terminal end of the second binding protein may be attached to the first binding protein, at the locations described above. In a particular embodiment, the or an N-terminus of the second binding protein is attached to the or a C-terminus of the first binding protein. In a preferred embodiment, when the first binding protein is a monoclonal antibody and the second binding protein is an scFv, the N-terminus of the scFv is attached to the C-terminus of the heavy chain of the antibody. In another preferred embodiment, the N-terminus of the scFv is attached to the C-terminus of the light chain of the antibody. Alternatively, the C-terminus of the scFv may be attached to the N-terminus of the heavy or light chain of the antibody. In another alternative, the C-terminus of the scFv may be joined via a linker molecule to the C-terminus of the heavy or light chain of the antibody.

In the above discussion of linkage of the first and second binding proteins by their termini, attachment to the C-terminus means attachment via the C-terminal carboxyl group and attachment to the N-terminus means attachment via the N-terminal amino group. Alternatively, rather than being joined at their termini the second binding protein may be joined to a side chain of an amino acid within the first binding protein and/or the first binding protein may be joined to a side chain of an amino acid within the second binding protein. In this instance the amino acid(s) may be located anywhere within the first and/or second binding proteins, i.e. at or near the N-terminus, at or near the C-terminus or at a position centrally within the polypeptide chain.

Any suitable type of covalent bond may be used to join the first and second binding proteins. For instance, the two proteins may be joined by a disulphide bond between the side chains of cysteine residues. Alternatively, the two proteins may be joined by an isopeptide bond, for instance between amino acid side chains (e.g. between the side chain of a lysine residue of one antigen binding protein and the side chain of a glutamic or aspartic acid residue of the other antigen binding protein), or between a side chain and a terminus (e.g. between the C-terminus of one binding protein and the side chain of a lysine residue of the other binding protein). In a preferred embodiment, the first and second binding proteins are joined by a peptide bond, i.e. the second binding protein (or at least one chain of the second binding protein) is located within the same polypeptide chain as at least one of the chains of the first binding protein.

As noted above, the second binding protein is preferably a single chain antibody derivative, e.g. an scFv, and the first binding protein is preferably a monoclonal antibody. In the instance that the second binding protein is a single chain antibody derivative (preferably an scFv) and the first binding protein is a monoclonal antibody, the second binding protein may be located within the same polypeptide chain as the light chain or the heavy chain of the antibody.

When the second binding protein and one chain of the first binding protein are located within a single polypeptide chain, the chain of the first binding protein is preferably located N-terminal to the second binding protein, though the second binding protein may alternatively be located N-terminal to the chain of the first binding protein.

In a particular embodiment the bispecific conjugate comprises a first binding protein which is a monoclonal antibody and a second binding protein which is an scFv, and the scFv is located within the same polypeptide chain as the heavy chain of the antibody. Preferably the scFv is located C-terminal to the antibody heavy chain, such that it is attached to the $C_H3$ domain of the antibody (though the scFv may be located N-terminal to the antibody heavy chain). Alternatively, the scFv may be located within the same polypeptide chain as the light chains of the antibody. Preferably the scFv is located C-terminal to the antibody light chain, such that it is attached to the $C_L$ domain of the antibody (though the scFv may be located N-terminal to the antibody light chain).

The first and second binding molecules may be directly joined to one another, or may be joined via a linker (i.e. joined indirectly to one another). It is well known in the art and widely described in the literature how to link two proteins together by means of a linker. For example, two proteins may be joined to one another via a linker between the thiol groups of two cysteine residues by reacting the proteins with a bifunctional agent capable of reacting with the two thiol groups, for example the N-hydroxysuccinimide ester of iodoacetic acid (NHIA) or N-succinimidyl-3-(2-pyridyldithio)propionate (SPDP). Amide and thioether bonds may for example be achieved with m-maleimidobenzoyl-N-hydroxysuccinimide ester (MBS) which can thus be used as a linker between the thiol groups of cysteine residues and/or amine groups. The linker may thus be a chemical reagent, i.e. a crosslinking agent, which reacts with functional groups in the first and second binding proteins to form covalent bonds between the two chains. Many linker molecules are known, and are standard in the art for linking the component parts of a conjugate together, including in the field of antibody constructs, and any such linker can be used.

In an alternative and preferred embodiment, as described above, the second binding protein (or a chain thereof) is located in the same polypeptide as the first binding protein (or a chain thereof). In this embodiment, the first and second binding proteins may be joined by a peptide linker. An exemplary peptide linker contains the potentially repeating $G_4S$ motif (SEQ ID NO: 21). This motif may be used in $(G_4S)n$ linkers, wherein n is typically 1-10, e.g. 2-6. A representative linker (where n=2, i.e. the linker is the $(G_4S)_2$ linker) is shown in SEQ ID NO: 22. Another example of a suitable linker is the rigid linker $EA_3K$ (SEQ ID NO: 80). This linker motif may also be repeated, such as for example in the form of the dimer $(EA_3K)_2$ (SEQ ID NO: 81). The linker peptide plays no functional or effector role, other than to link the two binding proteins (or chains thereof) together. The linker may function to spatially separate the two binding proteins, to avoid the function of either protein being sterically hindered by the other.

In a particular embodiment the bispecific conjugate comprises a first binding protein which is a monoclonal antibody and a second binding protein which is an scFv, and the scFv is: (i) located in a polypeptide chain which comprises, from N-terminus to C-terminus, the antibody heavy chain, a linker (in particular the linker of SEQ ID NO: 22) and the scFv; or (ii) located in a polypeptide chain which comprises, from N-terminus to C-terminus, the antibody light chain, a linker (in particular the linker of SEQ ID NO: 22) and the scFv.

As mentioned above, the second binding protein of the bispecific conjugate recognises a peptide moiety (i.e. a peptide sequence) that may be essentially any peptide or amino acid sequence. The peptide moiety may be a peptide which is not expressed on the surface of a human cell. Preferably, the peptide moiety has (i.e. consists of) a non-human amino acid sequence. By "a non-human amino acid sequence" is meant an amino acid sequence which is not obtained or derived from an amino acid sequence of or in a polypeptide which is encoded in the human genome. Thus in this embodiment the epitope recognised by the second binding protein is a non-human epitope, i.e. an epitope with a non-human sequence, and the second binding protein does not specifically bind or recognise a human protein.

The peptide moiety may be a natural peptide, i.e. a peptide with a sequence derived from a natural protein sequence. In this case, it is preferred that the peptide sequence is derived from a protein of non-human origin, e.g. the peptide sequence may be derived from a micro-organism. A peptide sequence derived from a micro-organism may be obtained from a prokaryote (i.e. a bacterium or an archaeon) or a microbial eukaryote (e.g. a yeast). Thus in a particular embodiment the peptide moiety has an amino acid sequence derived from a bacterium, i.e. a bacterial amino acid sequence (an amino acid sequence derived from a bacterial protein). A bacterial amino acid sequence may be derived from any suitable bacterium, e.g. a Gram-positive bacterium or a Gram-negative bacterium. In another embodiment the sequence of the peptide moiety is derived from a virus. That is to say the second binding protein may recognise an epitope from a microbial protein, e.g. a bacterial protein, or a viral protein.

In a particular embodiment the peptide moiety has an amino acid sequence derived from a microbial toxin (i.e. from a toxin produced by a microbe). Preferably the amino acid sequence is derived from a bacterial toxin (i.e. it is preferred that the second binding protein recognises a sequence derived from a bacterial toxin). Advantageously, the amino acid sequence is derived from a bacterial toxin used (in toxoid form) in standard vaccination schedules. The human immunological response to these toxoids are known, and it is known that such toxoids can be administered to humans without inducing a negative (i.e. damaging) immune response. Thus the use of such sequences as peptide tags in the context of the vaccine complexes of the invention can reasonably be assumed to be safe. Preferably the identified sequence does not bind endogenous antibodies with high affinity, or if endogenous antibodies bind, they do not out-compete the scFv binding of the bispecific conjugate.

Current toxoid vaccines include the tetanus and diphtheria vaccines, which use tetanus toxoid (Ttd, the inactive form of the tetanus toxin, Ttx) and diphtheria toxoid, respectively. The peptide moiety recognised by the second binding protein may thus be derived from *Clostridium tetani* (the causative agent of tetanus) or *Corynebacterium diphtheria* (the causative agent of diphtheria). In particular, the peptide moiety recognised by the second binding protein may be derived from tetanus toxin (SEQ ID NO: 23, UniProt accession number C4PD05) or diphtheria toxin (SEQ ID NO: 24, UniProt entry P00588). It is known to the skilled person that diphtheria toxin is technically encoded by the prophage *Corynephage beta*, rather than the *C. diphtheria* bacterial genome, but for the purpose of the current disclosure the diphtheria toxin is defined as being derived from *C. diphtheria*. In a preferred embodiment, the peptide moiety recognised by the second binding protein is derived from tetanus toxin (i.e. the second binding protein recognises an epitope within the tetanus toxin). By "derived from tetanus toxin" is meant that the peptide moiety recognised by the second binding protein comprises or consists of an amino acid sequence present in the tetanus toxin.

Alternatively, the tag peptide may have an artificial sequence, i.e. an amino acid sequence not found in nature, such that the second binding protein does not specifically bind any naturally-occurring protein.

In an embodiment, the tag peptide has an α-helical structure. In another embodiment, the tag peptide is unstructured, i.e. it does not adopt a particular secondary structure. Peptide secondary structure can be predicted using publicly-available software (e.g. Jpred4 (Drozdetskiy et al., Nucl. Acids Res. 43(W1): W389-W394, 2015) and PASTA 2.0 (Walsh et al., Nucl. Acids Res. 42(W): W301-W307, 2014). Peptide secondary structure can be experimentally determined by circular dichroism spectroscopy, as is well known in the art (see e.g. Greenfield, N., Nat Protoc. 1(6): 2876-2890, 2006).

One consideration in selecting a tag peptide may be that the peptide should not have a variable structure. In other words, without being bound by theory, it may be desirable that the structure of the tag peptide does not vary, or alter, depending on the context. For instance, it may be desirable that the structure of the tag peptide is the same when it is "naked" in solution (i.e. unmodified), when it is bound to a support (i.e. immobilised) and when its N-terminus and/or C-terminus is modified, e.g. if the peptide is synthesised in the context of a fusion protein (e.g. with an antigen), or chemically labelled, etc. If the peptide has a changeable structure it may not bind the second binding protein with high affinity in some contexts. Circular dichroism spectroscopy, for example, may be used to determine whether the structure of a tag peptide changes between contexts.

As detailed above, in a preferred embodiment the tag peptide is derived from tetanus toxin. Examples of suitable tag peptide sequences derived from tetanus toxin include the MTTE (SEQ ID NO: 25, WO 2011/115483), discussed further below, and the peptides of SEQ ID NOs: 11-15 (P001-P005, WO 2020/104690).

The MTTE is a known tetanus toxin-derived sequence and is a universal B cell epitope to which most individuals have developed endogenous antibodies. The present inventors have discovered when trimming the MTTE sequence (yielding the peptide set forth in SEQ ID NO: 16, corresponding to amino acids 1-12 of the MTTE of SEQ ID NO: 25) that scFv binding to this shorter peptide is retained. Thus in a particular embodiment, the tag peptide comprises or consists of the amino acid sequence set forth in SEQ ID NO: 16. In other embodiments the tag peptide may comprise or consist of a longer fragment of the MTTE, such as any one of those set forth in SEQ ID NOs: 26-29, or the full length MTTE set forth in SEQ ID NO: 25.

Alternatively, the tag peptide may comprise a variant of the minimal MTTE epitope of SEQ ID NO: 16 comprising up to two amino acid substitutions relative to SEQ ID NO: 16. Thus the tag peptide may comprise a variant of SEQ ID NO: 16 comprising one amino acid substitution relative to SEQ ID NO: 16, or a variant of SEQ ID NO: 16 comprising two amino acid substitutions relative to SEQ ID NO: 16. A number of such variants of SEQ ID NO: 16 are set forth in SEQ ID NOs: 30-41, and thus the tag peptide may comprise any one of the amino acid sequences set forth in SEQ ID NOs: 30-41. Accordingly, the second binding protein may recognise an epitope comprising the amino acid sequence of SEQ ID NO: 16 or an amino acid sequence comprising up to two amino acid substitutions relative to SEQ ID NO: 16.

The P001-P005 peptides (SEQ ID NOs: 11-15) are described in WO 2020/104690. As detailed therein, P001-P004 (SEQ ID NOs: 11-14) are derived from the tetanus toxin, while P005 (SEQ ID NO: 15) corresponds to P001 capped with an Asp residue at the N-terminus and an Arg residue at the C-terminus. N-biotinylated P001 (SEQ ID NO: 11), P004 (SEQ ID NO: 14) and P005 (SEQ ID NO: 15) were found to display an α-helical secondary structure, while P002-P003 were unstructured. As expected, the MTTE was found to be bound by antibodies from serum from subjects recently vaccinated against tetanus; P002 was bound by antibodies from serum from a minority of the same subjects, while P001 and P003-P005 were not bound by antibodies from serum from any of the subjects.

Thus in a particular embodiment the tag peptide comprises or consists of an amino acid sequence as set forth in any one of SEQ ID NOs: 11-15. The tag peptide may alternatively comprise or consist of a variant of any one of SEQ ID NOs: 11-15, i.e. an amino acid sequence comprising up to two amino acid substitutions relative to any one of SEQ ID NOs: 11-15 (e.g. an amino acid sequence comprising one amino acid substitution relative to any one of SEQ ID NOs: 11-15 or an amino acid sequence comprising two amino acid substitutions relative to any one of SEQ ID NOs: 11-15). In a further alternative, the tag peptide may comprise or consist of a part of one of the tetanus toxin-derived peptides of SEQ ID NOs: 11-15, for instance a fragment of at least 5, 6, 7 or 8 amino acids (e.g. a fragment of 8-15, 10-15, 8-12 or 10-12 amino acids). For instance, the tag peptide may comprise or consist of the tetanus toxin-derived peptide of SEQ ID NO: 42 (which is a fragment of P003, SEQ ID NO: 13) or any one of the tetanus toxin-derived peptides of SEQ ID NOs: 43, 44, 45 and 46 (which are fragments of P004, SEQ ID NO: 14). The tag peptide may alternatively comprise or consist of an amino acid sequence comprising up to two amino acid substitutions relative to any one of SEQ ID NOs: 42-46 (e.g. an amino acid sequence comprising one amino acid substitution relative to any one of SEQ ID NOs: 42-46 or an amino acid sequence comprising two amino acid substitutions relative to any one of SEQ ID NOs: 42-46). Thus the second binding protein may recognise an epitope with the amino acid sequence of any one of SEQ ID NOs: 11-16 or 25-46, and thus may bind tetanus toxin at an epitope with the sequence of any one of SEQ ID NOs: 11-16, 25 or 42-46.

Examples of scFvs which bind the MTTE fragment of SEQ ID NO: 16 (and the full length MTTE of SEQ ID NO: 25, as demonstrated in the Examples) include 14GIIICII-b (SEQ ID NO: 47) and 1BIIICI-b (SEQ ID NO: 48). The CDRs of the 14GIIICII-b scFv are set forth in SEQ ID NOs: 49-52, the amino acid sequence RMS, and SEQ ID NO: 54. VHCDR1, 2 and 3 of 14GIIICII-b have the amino acid sequences set forth in SEQ ID NOs: 49-51, respectively; VLCDR1, 2 and 3 of 14GIIICII-b have the amino acid sequences set forth in SEQ ID NOs: 52, the amino acid sequence RMS, and SEQ ID NO: 54, respectively. The CDRs of the 1BIIICI-b scFv are set forth in SEQ ID NO: 55-58, the amino acid sequence KAS, and SEQ ID NO: 60. VHCDR1, 2 and 3 of 1 BIIICI-b have the amino acid sequences set forth in SEQ ID NOs: 55-57, respectively; VLCDR1, 2 and 3 of 1 BIIICI-b have the amino acid sequences set forth in SEQ ID NO: 58, the amino acid sequence KAS, and SEQ ID NO: 60, respectively. In a particular embodiment the second binding protein is an scFv comprising six CDRs having the amino acid sequences set forth in SEQ ID NOs: 49-52, the amino acid sequence RMS, and SEQ ID NO: 54. In another embodiment, the second binding protein is an scFv comprising six CDRs having the amino acid sequences set forth in SEQ ID NOs: 55-58, the amino acid sequence KAS, and SEQ ID NO: 60. In yet another embodiment, the antigen binding protein is an scFv comprising the amino acid sequence set forth in SEQ ID NO: 47 or the amino acid sequence set forth in SEQ ID NO: 48, or an amino acid sequence having at least 80, 90 or 95% sequence identity thereto (with the proviso that the CDRs are as set out in SEQ ID NOs: 49-52, the amino acid sequence RMS, and SEQ ID NO: 54 or SEQ ID NOs: 55-58, the amino acid sequence KAS, and SEQ ID NO: 60, respectively).

Examples of scFvs which bind the P003 and P004 peptides of SEQ ID NOs: 13 and 14 include the scFvs Y-SM083-p03-C06 (SEQ ID NO: 68), Y-SM083-p04-C04 (SEQ ID NO: 69), Y-SM083-p04-D04 (SEQ ID NO: 70), Y-SM083-p04-F04 (SEQ ID NO: 71), Y-SM083-p04-G04 (SEQ ID NO: 72) and Y-SM083-p04-H04 (SEQ ID NO: 73). These scFvs are all described in WO 2020/104690. Y-SM083-p03-C06 binds P003 (SEQ ID NO: 13) and Y-SM083-p04-C04, Y-SM083-p04-D04, Y-SM083-p04-F04, Y-SM083-p04-G04 and Y-SM083-p04-H04 all bind P004 (SEQ ID NO: 14). In an embodiment, the second binding protein may thus be an scFv that binds P003 and comprises or consists of the amino acid sequence set forth in SEQ ID NO: 68, or an amino acid sequence having at least 80, 90 or 95% sequence identity thereto. In another embodiment, the second binding protein may be an scFv that binds P004 and comprises or consists of the amino acid sequence set forth in any one of SEQ ID NOs: 69-73, or an amino acid sequence having at least 80, 90 or 95% sequence identity thereto.

The bispecific conjugate of the invention may be synthesised by any method known in the art. In particular, as noted above it is preferred that the first and second binding proteins of the conjugate are provided in the context as a fusion protein (in particular a fusion protein comprising the heavy chain of an antibody (the first binding protein) and an scFv (the second binding protein), the light chain of the antibody being provided as a separate polypeptide). In this instance, the conjugate may be synthesised using a protein expression system, as described above in respect of production of the binding protein of the invention.

In another aspect, the invention provides a nucleic acid molecule that comprises a nucleotide sequence encoding a binding protein or a bispecific conjugate of the invention. The nucleotide sequence of the A9 light chain variable domain is set forth in SEQ ID NO: 75, and the nucleotide sequence of the A9 heavy chain variable domain is set forth in SEQ ID NO: 76. The nucleic acid molecule according to any embodiment of this aspect may be DNA or RNA. A nucleic acid molecule may encode one or more polypeptide chains. For example, a polynucleotide of the invention may encode a light chain, a heavy chain or both. Two nucleic acid molecules may be provided, one of which encodes a light chain and the other of which encodes the corresponding heavy chain. Such a nucleic acid molecule or pair of nucleic acid molecules may be expressed together such that a conjugate is generated. A polynucleotide encoding a light and a heavy chain may encode the two chains separately (i.e. as separate genes under the control of two separate promoters and other expression control elements) or may encode them polycistronically. Alternatively, the two chains may be encoded as a single polypeptide separated by a self-splicing linker (such as a 2A linker, see Lewis et al., 2015, J Neurosci Methods 256: 22-29).

The nucleic acid molecules of the invention can be synthesised according to methods well known in the art, as described by way of example in Sambrook et al. (1989, Molecular Cloning—a laboratory manual; Cold Spring Harbor Press).

The nucleic acid molecules may be provided in the form of an expression cassette which includes control sequences operably linked to the encoding nucleotide sequence, thus allowing for expression of the conjugate in a protein expression system. These expression cassettes, in turn, are typically provided within vectors (e.g. plasmids or recombinant viral vectors). A suitable vector may be any vector which is capable of carrying a sufficient amount of genetic information, and allowing expression of a conjugate or chain thereof.

The present disclosure and invention thus also includes a recombinant construct comprising a nucleic acid molecule as defined herein, preferably wherein the nucleic acid molecule is linked to a heterologous nucleic acid sequence. By "heterologous" as used herein is meant a nucleic acid sequence which is not natively linked to the nucleic acid molecule described herein, i.e. which is not linked to the nucleic acid molecule described herein in nature. In the construct, the nucleic acid molecule described herein may be flanked by restriction sites (i.e. nucleotide sequences recognised by one or more restriction enzymes) to enable easy cloning of the nucleic acid molecule of the invention. A "recombinant" construct is a nucleic acid construct synthesised using recombinant techniques, e.g. molecular cloning.

The term "linked" as used herein with respect to the construct may simply mean that the nucleic acid molecule is directly joined to a heterologous nucleic acid sequence. In a preferred embodiment, in the recombinant construct the nucleic acid molecule disclosed herein is operably linked to a heterologous expression control sequence, such that the expression control sequence regulates the expression of the nucleic acid molecule.

Thus, also provided is an expression cassette comprising a nucleic acid molecule as defined herein, or a vector that comprises a nucleic acid molecule or a recombinant construct as defined herein. Expression vectors are routinely constructed in the art of molecular biology and may for example involve the use of plasmid DNA and appropriate initiators, promoters, enhancers, terminators and other elements, such as for example polyadenylation signals which may be necessary, and which are positioned in the correct orientation, in order to allow for expression of conjugate, or chain thereof. Other suitable vectors would be apparent to persons skilled in the art, and include e.g. cloning vectors.

The invention also provides cells that comprise the nucleic acid molecule, recombinant construct, or vector of the invention. Such a cell is a cell into which such a molecule, construct or vector has been introduced. The cell may be defined as a host cell, e.g. a cloning host cell (used within the synthesis and/or production of the nucleic acid molecule, recombinant construct or vector) or a production host cell (used for expression of the protein(s) encoded by the nucleic acid molecule, recombinant construct or vector).

Such cells include transient, or preferably stable, higher eukaryotic cell lines, such as mammalian cells or insect cells, lower eukaryotic cells, such as yeast or prokaryotic cells such as bacterial cells. Particular examples of cells include mammalian HEK293T, CHO, HeLa, NSO and COS cells. Preferably the cell line selected will be one which is not only stable, but also allows for mature glycosylation and cell surface expression of a polypeptide. Such cells may be cultured using routine methods to produce the binding protein or bispecific conjugate of the invention.

As detailed above, in a further aspect the invention provides a complex comprising a bispecific conjugate of the second aspect of the invention and a tag construct comprising a peptide moiety recognised by the second binding protein of the conjugate covalently attached to an antigen, wherein the peptide moiety of the tag construct is non-covalently bound to the second binding protein of the conjugate. Such a complex may be formed by contacting the bispecific conjugate with the tag construct, such that the tag construct is bound by the second binding protein of the conjugate.

The peptide moiety recognised by the second binding protein is described above. As noted, it may be essentially any sequence, but is preferably a non-human sequence, preferably a bacterial sequence, most preferably a sequence derived from tetanus toxin.

As described in WO 2020/104690, a peptide library may be screened to identify possible tag peptides. For example, a library of peptides from, or derived from, a non-human protein sequence, for example a bacterial protein, e.g. tetanus toxin (TTx), may be obtained and screened to identify peptides with suitable characteristics. Such characteristics may include, for example, good aqueous solubility, and an α-helical structure or lack of secondary structure. Peptide libraries may be generated in various ways, including preparation of synthetic peptides. Screening may take place in silico using various available software programs, and/or by structural or other analysis.

As mentioned, the tag construct comprises the tag peptide covalently linked to an antigen. The covalent linkage may be as described above, with respect to covalent linkage of the first and second binding proteins in the conjugate. The linkage may be direct or indirect, i.e. the tag peptide may be joined to the antigen via a linker, as discussed above.

In a particular embodiment the tag construct is a polypeptide comprising a tag peptide linked to an antigenic peptide, i.e. as a fusion polypeptide. The fusion may be direct or indirect (via a linker peptide). The tag peptide and antigen peptide may be linked in either order, i.e. the tag peptide may be located N- or C-terminal to the antigen peptide. In another embodiment the antigen is embedded in the tag construct, i.e. there is a tag moiety both N- and C-terminal to the antigen. Thus the tag construct may comprise an antigen flanked by tag peptides, such that tag peptides are located at the N- and C-termini of the construct.

As noted above, the tag peptide may be essentially any peptide, though certain peptides are particularly preferred. The antigen may equally be any peptide against which it is desired to raise an immune response in a subject. Notably, however, the tag construct is not a naturally occurring peptide. Preferably the tag peptide and the antigen are derived from different proteins, more preferably from different species. Thus the tag construct is not a sequence found in nature, one part of which functions as the tag moiety and the other of which functions as the antigen. Rather, the tag construct has an artificial sequence.

The antigen may be any antigen that it is desired to deliver to a CD40-bearing cell, and in particular to an APC, e.g. a DC. Thus the antigen may be any antigen that it is desired for an APC to present. This may thus be an antigen, which when presented by the APC, is recognised by a T-cell it is desired to activate. In the context of therapy it is desirable to activate T-cells which recognise an antigen associated with a disease or condition it is desired to treat or prevent. Thus, the antigen may be an antigen expressed by (e.g. on the surface of) a cell it is desired to ablate, or more particularly to target for ablation. The antigen may thus be a cancer antigen (i.e. a sequence the expression of which is indicative of a cancer cell) or an antigen associated with an infection, e.g. an antigen of, or derived from, a pathogen. The target cell for the T-cell may thus be a cancer cell, or a cell infected by a pathogen. The pathogen may be a virus, or an intracellular pathogen, such as an intracellular bacterium (e.g. *Chlamydia* species) or a protozoan (e.g. apicomplexan, such as *Plasmodium*).

The antigen is thus a peptide containing one or more antigenic epitopes. The epitopes may be CD4+ and/or CD8+ T-cell epitopes, and/or B cell epitopes. The antigen may be a protein or polypeptide expressed by a cancer cell or pathogen, or a part thereof. In particular, the antigen may be a neo-antigen expressed by a cancer cell, that is an antigen generated by a somatic mutation in a cancer cell, which is not expressed by non-cancer cells. Thus, an antigenic peptide may comprise one or more neo-epitopes. Such neo-epitopes may for example be generated by frameshift mutations. Such mutations may occur in cancers which display microsatellite instability (MSI). Various neo-antigens and neo-epitopes are known and are described in the literature, in the context of various different cancers. Neo-antigens may alternatively be referred to as cancer-specific antigens. Alternatively or additionally, the antigenic peptide may be, or may comprise one or more epitopes from, a tumour-associated antigen or an antigen from an oncovirus. Again, tumour-associated antigens are well known in the art and widely described in the literature, including for example, cancer testis antigens and hTERT antigens. Oncoviral antigens are also well known and described, including for instance antigens from human papillomavirus (HPV) and Epstein-Barr virus (EBV). A comprehensive list of known, validated cancer antigens (both tumour-specific neo-epitopes and tumour-associated antigens) is publicly available online: at the "Cancer Antigenic Peptide Database". An extensive list of tumour antigens is also provided in Wang & Wang, Cell Research 27: 11-37, 2017. Neo-antigens, cancer-associated antigens and oncoviral antigens are defined herein as cancer antigens.

Viral antigens and antigens expressed by other intracellular pathogens are also well known in the art. The antigen can be or include one or more epitopes from one or more serotypes of a given pathogen, and can also include CD4 and CD8 epitopes, and/or linear or conformational B cell epitopes.

The antigen may thus be a naturally-occurring peptide molecule or a fragment or part of a naturally-occurring protein. It may alternatively be a synthetic peptide, for example a peptide designed and prepared to contain one or more different epitopes, for example epitopes which do not occur naturally together. Such a synthetic peptide may comprise two or more epitopes linked together directly, or indirectly by linker, or spacer, sequences. The synthesis of such synthetic epitope-containing peptides (e.g. synthetic long peptides, SLPs) is known in the art, and known SLP peptides may be used.

In a further aspect, the invention provides a pharmaceutical composition comprising (i) a binding protein of the invention, as described above; (ii) a bispecific conjugate of the invention, as described above, or (iii) a complex of the invention, as described above. In addition to the binding protein, bispecific conjugate or complex, the pharmaceutical composition also comprises at least one pharmaceutically acceptable carrier or excipient.

Also provided by the present invention are kits and products, as defined above, comprising, separately, a bispecific conjugate and a tag construct as described above. In such kits and products the conjugate and tag construct may be separately provided in compositions containing a pharmaceutically acceptable carrier or excipient.

As used herein, "pharmaceutically acceptable carrier or excipient" includes any and all solvents, dispersion media, coatings, antibacterial and antifungal agents, isotonic and absorption delaying agents and the like that are physiologically compatible.

Preferably, the carrier or excipient is suitable for parenteral, e.g. intradermal, intravenous, intramuscular or subcutaneous administration (e.g. by injection or infusion). Depending on the route of administration, the binding protein, bispecific conjugate, complex or constituent component thereof may be coated in a material to protect the it from the action of acids and other natural conditions that may inactivate or denature it.

Preferred pharmaceutically-acceptable carriers comprise aqueous carriers or diluents. Examples of suitable aqueous carriers that may be employed in the pharmaceutical compositions, kits and products include water, buffered water and saline. Examples of other carriers include ethanol, polyols (such as glycerol, propylene glycol, polyethylene glycol, and the like), and suitable mixtures thereof, vegetable oils and injectable organic esters, such as ethyl oleate. Proper fluidity can be maintained, for example, by the use of coating materials, such as lecithin, by the maintenance of the required particle size in the case of dispersions, and by the use of surfactants. In many cases, it will be preferable to include isotonic agents, for example, sugars, polyalcohols such as mannitol, sorbitol, sodium chloride and the like.

The pharmaceutical composition, product or kit also may include a pharmaceutically-acceptable anti-oxidant. They may also contain adjuvants such as preservatives, wetting agents, emulsifying agents and dispersing agents. Prevention of presence of microorganisms may be ensured both by sterilization procedures, and by the inclusion of various antibacterial and antifungal agents, for example, paraben, chlorobutanol, phenol sorbic acid, and the like. In addition, prolonged absorption of the injectable pharmaceutical form may be brought about by the inclusion of agents which delay absorption such as aluminum monostearate and gelatin.

Therapeutic compositions typically must be sterile and stable under the conditions of manufacture and storage. The composition can be formulated as a solution, microemulsion, liposome, or other ordered structure suitable to high drug concentration.

Sterile injectable solutions can be prepared by incorporating the active agent (e.g. complex) in the required amount in an appropriate solvent with one or a combination of ingredients enumerated above, as required, followed by sterilization microfiltration. Generally, dispersions are prepared by incorporating the active agent into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active agent plus any additional desired ingredient from a previously sterile-filtered solution thereof.

Pharmaceutical compositions, products and kits may comprise additional active ingredients as well as the binding protein, bispecific conjugate, complex or component thereof, for example they may comprise additional therapeutic or prophylactic agents. Thus, the complex may be used as a monotherapy or as part of a combination therapy, e.g. in the treatment of cancer. A kit or combination product as described herein may additionally contain instructions for use.

The binding protein of the present invention, bispecific conjugate of the present invention, complex of the present invention, pharmaceutical composition of the present invention, kit of the present invention and combination product of the present invention may be used in therapy. The invention thus provides the binding protein, bispecific conjugate, complex, pharmaceutical composition or kit of the invention for use in therapy. By therapy is meant the treatment of a subject. By "therapy" as used herein is meant the treatment of any medical condition. Such treatment may be prophylactic (i.e. preventative), curative (or treatment intended to be curative), or palliative (i.e. treatment designed merely to limit, relieve or improve the symptoms of a condition). In curative and palliative applications, complexes or compositions are administered to a subject already suffering from a disorder or condition, in an amount sufficient to cure, alleviate or partially arrest the condition or one or more of its symptoms. Such therapeutic treatment may result in a decrease in severity of disease symptoms, or an increase in frequency or duration of symptom-free periods. An amount adequate to accomplish this is defined as a "therapeutically effective amount". Effective amounts for a given purpose will depend on the disease or condition to be treated, its severity and the size/weight and general state of the subject.

Prophylactic treatment may include the prevention of a condition, or a delay in the development or onset of a condition. For example the complex may be used to prevent an infection, or to reduce the extent to which an infection may develop, or to prevent, delay or reduce the extent of a cancer developing, or recurring, or for example to prevent or reduce the extent of metastasis.

A subject, as defined herein, refers to any mammal, e.g. a farm animal such as a cow, horse, sheep, pig or goat, a pet animal such as a rabbit, cat or dog, or a primate such as a monkey, chimpanzee, gorilla or human. Most preferably the subject is a human.

The combination product of the invention comprises a bispecific conjugate as defined herein and a tag construct as defined herein as a combined preparation for simultaneous or sequential use in therapy. That is to say, when the combination product disclosed herein is used according to the invention, i.e. in therapy, the conjugate and tag construct are administered simultaneously or sequentially to the subject. Similarly, when the kit of the invention is used in therapy, the bispecific conjugate and tag construct are administered simultaneously or sequentially to the subject. By "simultaneous" administration, as used herein, means that the two components are administered to the subject at the same time, or at least substantially the same time, by the same administrative route and at substantially the same location. By "sequential" administration, as used herein, is meant that the two components are administered to the subject at different times. In particular, administration of the first component is completed before administration of the second component commences.

Due to the nature of the present invention, sequential administration of the bispecific conjugate and tag construct requires both to be administered by the same route and at substantially the same location. Furthermore, although the administration of the conjugate and tag construct may be temporally spaced, the interval between the administrations should be such as to allow a complex to be formed, when both components have been administered. Thus, for example, both components may be administered within 1 hour of each other, or more particularly within 40, 30, 20, 15, 10, 8, 7, 6, 5, 4, 3, 2 or 1 minute, or less than a minute, of each other.

Mention of the complex of the invention (or a pharmaceutical composition comprising such a complex) being administered to a subject for therapeutic purposes is to be understood as referring to a pre-mixed composition (e.g. solution) comprising both components of the complex (i.e. a bispecific conjugate of the invention and a tag construct as described above), which components may exist in a dynamic equilibrium comprising the complex and its two individual components.

In particular, the binding protein, bispecific conjugate, complex, composition, kit or combined product of the invention may be used in the treatment or prevention of cancer. By cancer is meant any malignant or pre-malignant neoplastic condition. The cancer may be thus be any cancer, of any organ, tissue or cell type. Cancers which present as solid tumours, and which do not exhibit solid tumours are included. Accordingly, haemopoietic cancers are included.

The cancer may be prostate cancer, breast cancer, colorectal cancer, pancreatic cancer, ovarian cancer, lung cancer, cervical cancer, rhabdomyosarcoma, neuroblastoma, multiple myeloma, leukemia, acute lymphoblastic leukemia, melanoma, bladder cancer, head and neck cancer, lymphoma, glioblastoma, or skin cancer. It may also be adrenal cancer, bone cancer, brain cancer, oespophageal cancer, eye cancer, gastric cancer, oral cancer, penile cancer, testicular cancer, thyroid cancer, uterine cancer, and vaginal cancer. Mast cell tumours and hemangiosarcoma may also be treated according to the present invention. The cancer may be newly diagnosed and naïve to treatment or it may be relapsed or refractory, or relapsed and refractory, primary or metastatic.

As explained above, the CD40-specific binding protein of the invention activates the immune system by agonising or stimulating CD40 on APCs, particularly on dendritic cells. In particular, this may lead to T-cell activation. The subsequent immune response exerts an anti-cancer effect on neighbouring or accessible tumour cells, without regard to CD40 expression by the tumour. The binding protein of the invention, or complex containing it, may therefore be effective against both CD40-positive and CD40-negative cancers. The binding protein can also exert its effect as an adjuvant within a vaccination regimen against a pathogen. If a vaccine platform (e.g. an attenuated virus or a DNA/RNA-based vaccine) does not stimulate a sufficient immune response by itself, CD40 activation may be required to stimulate effective anti-pathogen immune responses resulting in neutralising antibodies or T cell responses.

In addition to the agonistic immune activating effect provided by the CD40-specific binding protein, the complex of the invention also provides an antigen, which may be processed and presented to T-cells which are activated, and thus T-cells may be primed to target cancer cells which express the antigen or to a virally infected cell. This may be of particular benefit in circumstances where cancer antigen presence is low or reduced, for example where a tumour has been surgically removed, or in cases where an anti-CD40 therapeutic cannot be delivered intra-tumourally. The complex provides a means for providing cancer antigen in the vicinity of the agonistic activation signal.

The cancer antigen to be delivered by the complex may be selected based on the subject and the particular cancer, thus allowing personalised medicine. For example, the cancer of the subject may be subjected to genetic profiling, allowing a suitable antigen to be selected. A bank or library of antigens, or tag constructs comprising antigens, may be provided from which a suitable tag construct may be prepared or selected depending on the cancer type of the subject.

The binding protein, complex (and kit and combination product) of the invention may also be useful in the treatment or prevention of an infection. The present invention may in particular be used in therapy for (e.g. vaccination against) viral infections, in particular infections caused by RNA viruses. Infections caused by RNA viruses which may be treated of prevented (by vaccination) according to the present invention include infections caused by coronaviruses (such as SARS-CoV-1 (the causative agent of SARS), SARS-CoV-2 (the causative agent of COVID-19) and MERS-CoV), influenza viruses, ebola virus, hepatitis C virus (HCV), hepatitis E virus (HEV), rabies virus, poliovirus, Ross River virus and measles virus.

The invention may also be used in treatment for or vaccination against infections caused by Epstein-Barr virus (EBV), cytomegalovirus (CMV), human herpes viruses (e.g. HHV-6), parvovirus B19 and human papillomavirus (HPV), though any viral infection can, in principle, be treated or prevented according to the present invention.

Intracellular bacterial infections may also be treated according to the present invention, e.g. Brucellosis (caused by bacterial species of the genus *Brucella*), Q fever (caused by *Coxiella burnetii*), diseases caused by species of Chlamydiae, such as *chlamydia* (caused by *Chlamydia trachomatis*) and pneumonia (caused by *Chlamydia pneumoniae*), leprosy (caused by *Mycobacterium leprae* and *Mycobacterium lepromatosis*) and tuberculosis, including disseminated tuberculosis (caused by *Mycobacterium tuberculosis*). Intracellular fungal or protozoal infections may also be treated by the current invention, including leishmaniasis (caused by trypanosomes of the genus *Leishmania*) and toxoplasmosis (caused by the apicomplexan *Toxoplasma gondii*). The antigen may thus be derived from any of the aforementioned pathogens.

In the case of the CD40-specific binding protein, agonism of CD40 may activate the immune system to fight the infection (on a similar principle to use of the binding protein in therapy for cancer). In the case of the complex of the invention, as described above this may be provided with an antigen derived from the target pathogen, thus inducing a specific immune response against the pathogen. The vaccine platform is beneficially adaptable for e.g. a pandemic situation. This adaptability can in particular be provided by using a tag construct comprising an antigen that can be modified for viral diversity and antigen drift. Viral antigens can be selected based on HLA prevalence in a certain region along with viral serotype determinants.

The antigen (e.g. cancer antigen or pathogen-derived antigen) may be selected to be recognised by a particular subset of T-cells in the subject to be treated, the T-cells expressing a TCR known to recognise the chosen antigen. In particular, the antigen may be selected on the basis that it is recognised by T-cells used in adoptive cell therapy in the subject to be treated.

For instance, in adoptive cell therapy, T-cells may be obtained from the subject, and T-cells which recognise an antigen of interest isolated. The isolated T-cells may then be expanded and/or otherwise treated to stimulate their effector functionality, and then re-infused into the subject to be treated. In this context, the antigen recognised by the re-infused T-cells may be used in the tag construct. A complex of the invention may then be administered to the subject, so that the antigen activates the re-infused T-cells.

Alternatively, T-cells may be obtained from the subject to be treated or a donor, and genetically modified to express a TCR which recognises a target antigen. The genetically modified T-cells may then be expanded and/or otherwise treated to stimulate their effector functionality, and then infused (or re-infused) into the subject to be treated. In this context, the antigen recognised by the genetically modified T-cells may be used in the tag construct. A complex of the invention may then be administered to the subject, so that the antigen activates the infused T-cells. Methods in which administration of a complex of the invention is combined with adoptive cell therapy are particularly useful in the treatment of cancer, in which case the antigen used in the tag construct is a cancer antigen.

The invention thus provides a method of treating or preventing cancer, comprising administering to a subject a binding protein of the invention, a bispecific conjugate of the invention, a complex of the invention or a pharmaceutical composition of the invention.

Similarly, the invention provides a method of treating or preventing an infection, comprising administering to a subject a binding protein of the invention, a bispecific conjugate of the invention, a complex of the invention or a pharmaceutical composition of the invention.

In a particular embodiment, the invention provides a method of treating cancer in a subject, the method comprising:

(i) obtaining T-cells from the subject;

(ii) isolating T-cells which recognise a target cancer antigen, and optionally expanding the isolated T-cells;

(iii) re-infusing the isolated T-cells into the subject; and (iv) administering to the subject a complex of the present invention, wherein the tag construct comprises the target cancer antigen. Equivalently, in step (iv) the subject could alternatively be separately administered a bispecific conjugate of the invention and a tag construct comprising the target cancer antigen.

In another embodiment, the invention provides a method of treating cancer in a subject, the method comprising:

(i) obtaining T-cells from the subject or a donor;

(ii) genetically modifying the T-cells to express a TCR which recognises a target cancer antigen, and optionally expanding the T-cells before or after genetic modification;

(iii) infusing the genetically modified T-cells into the subject; and (iv) administering to the subject a complex of the present invention, wherein the tag construct comprises the target cancer antigen. Equivalently, in step (iv) the subject could alternatively be separately administered a conjugate of the invention and a tag construct comprising the target cancer antigen.

The invention similarly provides the use of a binding protein of the invention, a bispecific conjugate of the invention or a complex of the invention in the manufacture of a medicament for the treatment of prevention of cancer.

The invention also provides the use of a binding protein of the invention, a bispecific conjugate of the invention or a complex of the invention in the manufacture of a medicament for the treatment of prevention of an infection.

Throughout the above embodiments, reference to the use of a complex of the invention includes the combined use of a bispecific conjugate of the invention and a tag construct, which are separately or sequentially administered.

In an alternative embodiment, the complex of the invention may be used in gene therapy. In this embodiment, a gene therapy vector or delivery system encoding both a bispecific conjugate of the invention and a corresponding tag construct may be administered to the subject. Upon take up by cells of the subject, the conjugate and tag are expressed and secreted, and form a complex in vivo.

As noted above, the binding protein of the invention, bispecific conjugate of the invention or complex of the invention may be used as a monotherapy, or in conjunction with other therapeutic agents. Thus, in the treatment of cancer the other therapeutic agent may be an anti-cancer agent, such as a chemotherapeutic agent, numerous classes of which are known in the art, or an immunological agent, including for example, interferons, immune checkpoint inhibitors (e.g. anti-PD-1, -PD-L1 or -CTLA4 antibodies) and other immune-enhancing agents (e.g. anti-OX40 agonistic antibodies). Other therapeutic agents may be beneficial in the treatment of cancer or indeed an infection, e.g. anti-proliferative or anti-inflammatory cytokines, and anti-proliferative, immunomodulatory or factors influencing blood clotting, or inhibitors of angiogenesis. For treatment of an infection, the other (or second) therapeutic agent may be an anti-microbial agent, e.g. an antibiotic, anti-fungal or anti-viral agent.

The binding protein, bispecific conjugate, complex, or pharmaceutical composition comprising the binding protein, bispecific conjugate or complex (or the conjugate and tag construct components thereof) may be administered via one or more routes of administration using one or more of a variety of methods known in the art. Similarly, the conjugate and tag construct may be individually administered by these same methods. As will be appreciated by the skilled artisan, the route and/or mode of administration will vary depending upon the desired results. Preferred routes of administration include intravenous, intramuscular, intradermal, intraperitoneal, subcutaneous, spinal or other parenteral routes of administration, for example by injection or infusion, e.g. directly to the site of a tumour.

The phrase "parenteral administration" as used herein means modes of administration other than enteral and topical administration, usually by injection. Alternatively, a non-parenteral route may be used, such as a topical, epidermal or mucosal route of administration. Local administration is preferred, including peritumoral, juxtatumoral, intratumoral, intralesional, perilesional, intra cavity infusion, intravesicle administration, and inhalation. However, the antigen binding protein, complex or composition may also be administered systemically.

In embodiments where the bispecific conjugate and tag construct are administered individually, i.e. they are not first pre-mixed to form the complex, the conjugate and tag construct must be administered via the same route. Preferably, they are both administered locally, e.g. intradermally, at the same (or substantially the same) site, such that the two components mix, and thus combine to form the complex, rapidly after administration. In these embodiments, the two components must be administered to the subject either simultaneously or rapidly one after the other, avoiding delay between administration of the first component and administration of the second component. This ensures the second component is administered, and complex formation is enabled, before the first component degrades or becomes excessively disseminated from the administration site.

A suitable dosage of a specific binding protein, bispecific conjugate or complex of the invention may be determined by a skilled medical practitioner. Actual dosage levels of the active ingredients in the pharmaceutical compositions and products of the present invention may be varied so as to obtain an amount of the active ingredient which is effective to achieve the desired therapeutic response for a particular subject, i.e. patient, without being toxic to the patient. The selected dosage level will depend upon a variety of pharmacokinetic factors including the activity of the particular complex/conjugate employed, the route of administration, the time of administration, the rate of excretion of the complex, the duration of the treatment, other drugs, compounds and/or materials used in combination with the particular compositions employed, the age, sex, weight, condition, general health and prior medical history of the patient being treated, and like factors well known in the medical arts.

A suitable dose of a binding protein or complex of the invention may be, for example, in the range of from about 0.1 µg/kg to about 100 mg/kg body weight of the patient to be treated. For example, a suitable dosage may be from about 0.1 µg/kg to about 10 mg/kg body weight per day or from about 10 µg/kg to about 5 mg/kg body weight per day.

Dosage regimens may be adjusted to provide the optimum desired response (e.g. a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

The binding protein or complex (or conjugate and tag construct) may be administered in a single dose or in multiple doses. The multiple doses may be administered via the same or different routes and to the same or different locations. Alternatively, complexes can be administered as a sustained release formulation, in which case less frequent administration is required. Dosage and frequency may vary depending on the half-life of the administered species in the patient and the duration of treatment that is desired. The dosage and frequency of administration can also vary depending on whether the treatment is prophylactic or therapeutic. In prophylactic applications, a relatively low dosage may be administered at relatively infrequent intervals over a long period of time. In therapeutic applications, a relatively high dosage may be administered, for example until the patient shows partial or complete amelioration of symptoms of disease. In an exemplary dosage regime, the complex (or combination of the conjugate and tag construct) is administered to the subject once a week, once a fortnight or once every three weeks, in a cycle repeated from 2 to 10 times.

Combined administration of two or more agents may be achieved in a number of different ways. In one embodiment, the complex and the other agent may be administered together in a single composition. In another embodiment, the complex and the other agent may be administered in separate compositions as part of a combined therapy. For example, the complex may be administered before, after or concurrently with the other agent. The complex of the invention may be administered in combination with or sequentially to tumour targeting antibodies, target therapy, pathway inhibitors or other immunomodulatory antibodies targeting e.g. PD-1, PD-L1, CD137, GITR, OX40, CTLA-4, CD27, HVEM, LTpR, and LAG3. Further the complex may also be combined with local radiation. Similarly, such additional therapies may be co-administered when the conjugate and tag construct are individually administered to the subject.

As noted above, the invention also provides an in vitro or ex vivo method of activating a T-cell expressing a TCR which recognises an antigen, said method comprising contacting an antigen-presenting cell with:

i) a bispecific conjugate of the invention and a tag
　　　　construct as defined above, wherein said tag construct
　　　　comprises the antigen recognised by said TCR; or
　　ii) a complex of the invention, wherein the tag construct
　　　　of said complex comprises the antigen recognised by
　　　　said TCR.

Thus the complex or bispecific conjugate of the invention may be used to activate APCs in vitro or ex vivo, as well as in vivo as described above. The complex and bispecific conjugate (in combination with a tag peptide) thus have both medical and non-medical uses, and all such uses are encompassed herein. For example, isolated or cultured APCs may be contacted with the complex, e.g. in a laboratory setting, for example for research, development or testing purposes. This may be achieved by pre-mixing the conjugate and tag-construct, to form the complex, and then applying the complex to the APCs. Alternatively, the conjugate and tag construct can be individually applied to the APCs, such that the complex forms within the APC culture.

As noted above, the complex may be used to activate a T-cell which expresses a TCR which recognises the antigen present in the tag construct. Specifically, the TCR recognises the antigen when presented by an APC (i.e. in the context of an MHC). Thus, an APC activated by the complex, or for activation by the complex, may be contacted with the T-cell. Thus for example, APCs may be cultured or incubated in the presence of the complex (or constituent parts thereof), following which the APCs may be contacted with the T-cells, e.g. co-cultured, or further incubated in the presence of the T-cells. Alternatively, the complex (or constituent parts thereof), APCs and T-cells may be incubated or co-cultured together. Thus the antigen is delivered to the APCs and presented to the T-cells, resulting in their activation.

EXAMPLES

Example 1

Phage Display Selection on Human CD40 Using a Human scFv Library

Phage display selections were performed to enable isolation of scFv fragments with specificity for human CD40.

Materials and Methods

Phage Display Selection

Biopanning was performed using four selection rounds of enrichment employing two human synthetic scFv phage libraries, SciLifeLib1 and SciLifeLib2 (SciLifeLab, Stockholm, Sweden). SciLifeLib 1 and 2 are naive human synthetic scFv libraries, similar in design and construction to previously reported (Säll et al., *Protein Eng Des Sel* (2016) 29: 427-437). Briefly, human germline genes IGHV3-23 and IGKV1-39 were used as library scaffold and Kunkel mutagenesis was used to introduce diversity into four of the six CDRs, namely VHCDR1, VHCDR2, VHCDR3 and VLCDR3. The selection was performed using streptavidin-coated magnetic beads (DYNABEADS® M-280, ThermoFisher Scientific®, #11206D) and Avi-tagged human CD40 extracellular domain (AcroBiosystems, #CD0-H82E8, amino acids 21-193), referred to as hCD40-avi. The Avi-tag allows site-specific incorporation of biotin. The selection pressure was increased by gradually decreasing the antigen amount (327 nM to 35 nM) and by increasing the number and intensity of washes between the different rounds.

In order to remove non-specific or streptavidin binders, pre-selection was performed by incubation of the phage stocks against empty streptavidin coated magnetic beads prior round 1 and 2. Also, 1% bovine serum albumin (BSA) was included as blocking agent throughout the selection procedure. Elution of antigen-bound phages was performed using a trypsin-aprotinin approach. The entire selection process, except the phage-target protein incubation step, was automated and performed with a Kingfisher Flex robot. Recovered phages were propagated in XL1 blue E. coli, either on agar plates at 37° C. overnight (Round 1 and 2) or in solution at 30° C. overnight (Rounds 3 and 4). Phage stocks were made by infecting with an excess of M13K07 helper phage (New England Biolabs, #N0315S) and scFv expression induced by the addition of IPTG. The overnight cultures were PEG/NaCl-precipitated, resuspended in selection buffer and used for the next round of selection.

Re-Cloning and Expression of scFv

To allow production of soluble scFv, phagemid DNA from the third and fourth round of each selection track was isolated. In pools, the genes encoding the scFv fragments were restriction enzyme digested and sub-cloned into a screening vector, providing a signal for secretion of the scFv along with a triple-Flag tag and a hexahistidine (His) tag at the C-terminus. The constructs were subsequently transformed into TOP10 E. coli. Single colonies were picked, cultivated and IPTG-induced for soluble scFv expression in 96-well format. In total, 940 scFv clones present in bacterial supernatant were prepared for a primary ELISA screen.

ELISA Screen

Streptavidin was coated onto a 384-well ELISA plate at 1 μg/ml in PBS, 4° C. overnight, and hCD40-avi added after washing, diluted to 0.1 μg/ml in blocking buffer (PBS supplemented with 0.5% BSA+0.05% Tween20). Two negative control proteins, streptavidin and BSA, were also coated onto plates. Flag-tagged scFv clones present in bacterial supernatant were diluted 1:3 in blocking buffer and allowed to bind to the coated proteins. Detection of binding was enabled through an HRP-conjugated α-Flag M2 antibody (Sigma-Aldrich #A8592) followed by incubation with 3,3', 5,5'-tetramethylbenzidine (TMB) ELISA substrate (Thermo Fisher Scientific® #34029). The colorimetric-signal development was stopped by adding 1 M sulphuric acid and the plate was read at 450 nm. All samples were assayed in duplicate.

DNA Sequencing 157 positive scFv clones showing binding to hCD40-avi were sent for Sanger DNA sequencing by GATC Biotech (Ebergsberg, Germany).

Results

Two selection tracks were carried out in parallel on human CD40 using SciLifeLib 1 and 2. Following re-cloning of selected scFv clones, a total of 940 colonies were picked from selection rounds 3 and 4. A primary ELISA screen resulted in 159 potential hits. DNA sequencing of these resulted in the identification of 59 sequence unique clones.

Example 2

Kinetic Screen of 59 Sequence Unique scFvs by SPR

The 59 sequence unique scFv clones from Example 1 were selected for further characterisation by surface plasmon resonance (SPR) in a kinetic screen-based approach to enable ranking of the different clones.

Materials and Methods

The kinetic screen was performed on a Biacore T200 instrument (GE Healthcare). An α-Flag M2 antibody (Sigma-Aldrich #F1804), functioning as a capture ligand, was immobilised onto all four surfaces of a CM5-S amine sensor chip according to the manufacturer's recommendations.

59 Flag-tagged scFv-clones present in bacterial supernatant were injected and captured on the chip surfaces, followed by injection of 25 nM human CD40 extracellular domain-Fc fusion construct (R&D Systems, #1493-CDB, CD40 amino acids 21-193; hCD40-Fc). The surfaces were regenerated with 10 mM glycine-HCl pH 2.2. All experiments were performed at 25° C. in running buffer (HBS supplemented with 0.05% Tween20, pH 7.5).

By subtracting the response curve of a reference surface (an α-Flag M2 antibody immobilised surface), response curve sensorgrams were obtained. Data was analysed using the Biacore T200 Evaluation 3.1 software.

Results

An α-Flag M2 antibody was immobilised onto all four surfaces of a CM5-S chip and similar RU-levels of captured scFv clones were obtained. Following hCD40-Fc injection at 25 nM, each surface was successfully regenerated using a low pH acid solution.

Analysis of data was performed by visual inspection of the sensorgrams (not shown). 15 of the tested scFvs were considered promising based on binding to hCD40. In particular, a high binding response and favourable slow off-rate were considered.

Example 3

Conversion to Full Antibody Format

Twelve of the most promising scFvs from phage selection were selected for conversion to full-length human IgG2 antibody format. The rationale for including these particular clones was their performance in a panel of binding assays (see Examples 1 and 2) and sequence analysis. Two negative controls were similarly converted to human IgG2: G-Strep-1 (GS1, an in-house anti-streptavidin scFv) and B1-8 (an anti-4-hydroxy-3-nitrophenylacetyl (NP) scFv, Reth et al., European Journal of Immunology 8(6): 393-400, 1978) as well as two agonistic anti-CD40 antibodies found in the literature, namely 1150/1151 (WO 2015/091853) and CP-870,893 (US 2017/0342159). As a comparison, the latter two were also converted to human IgG1 format. 1150/1151 as hIgG1 and hIgG2 is referred to herein as X-SM083-Ab-1 and X-SM083-Ab-2, respectively; CP-870,893 as hIgG1 and hIgG2 is referred to herein as X-SM083-Ab-4 and X-SM083-Ab-5, respectively (Ab-1, Ab-2, Ab-4 and Ab-5, respectively, for short). The twelve IgG2 antibodies produced from the scFvs from phage selection are referred to as Y-SM083-A1, Y-SM083-A6, Y-SM083-A9, Y-SM083-B1, Y-SM083-B3, Y-SM083-B8, Y-SM083-C6, Y-SM083-E7, Y-SM083-E8, Y-SM083-F4, Y-SM083-F7 and Y-SM083-G2 (A1, A6, A9, B1, B3, B8, C6, E7, E8, F4, F7 and G2, respectively, for short).

Materials and Methods

In-Fusion Cloning, Transfection into HEK293, Expression and Purification

The VH and VL regions of the chosen scFvs were PCR amplified and inserted into the in house-constructed vector pHAT-hIgG2 using the In-Fusion HD Plus Cloning Kit (Clontech #638909). Transfection of plasmid DNA into expiHEK293 cells was performed using an Expi-Fectamine™ 293 Transfection Kit (Thermo Fisher Scientific® #A14525) in 80 ml cultures. The cultures were harvested after 5 days and antibodies purified by affinity chromatography using a HiTrap Protein A HP column (GE Healthcare) followed by buffer exchange to PBS using a HiTrap Desalting column (GE healthcare). Endotoxin levels were <1 EU/mg as determined by LAL chromogenic endotoxin assay. SDS-PAGE was performed to determine purity and integrity of the purified IgG and concentrations determined using an Implen NP80 UV-Vis Spectrophotometer. In addition, size exclusion chromatography was run on each of the purified antibodies (Agilent Bio SEC-3).

ELISA

Biotinylated antigens were immobilised in the wells of a 384-well ELISA plate via streptavidin (1 µg/ml) at a concentration of 0.1 µg/ml for hCD40-avi (AcroBiosystems, #CD0-H82E8) or 1 µg/ml for NP and nitrohydroxyiodophenylacetate (NIP, also recognised by the B1-8 scFv) in PBS. Purified antibodies were diluted in blocking buffer (PBS+ 0.5% BSA+0.05% Tween20) to a final concentration of 1, 0.2 or 0.04 µg/ml, and added to the wells. Detection of bound IgG was performed using a horseradish peroxidase (HRP)-labelled anti-human IgG kappa antibody, followed by incubation with the chromogen Ultra TMB-ELISA (Thermo Scientific Pierce, Rockford, IL, USA). The signal development was stopped by the addition of 1 M sulphuric acid and the absorbance was measured at 450 nm.

Results

All CD40-binding antibodies and controls were successfully re-cloned to human IgG format, expressed in HEK293 cells and purified by Protein A-conjugated magnetic beads on a Kingfisher Flex instrument. All antibodies were of the expected molecular weight and demonstrated an acceptable level of purity, as evaluated by SDS-PAGE. ELISA confirmed retained antigen binding of all clones after conversion, except for Y-SM083-C6 (data not shown). This clone was therefore excluded from further analysis.

The VL and VH sequences of Y-SM083-A9 are set forth in SEQ ID NOs: 7 and 8, respectively; the VL and VH sequences of Y-SM083-B8 are forth in SEQ ID NOs: 61 and 62, respectively. The VL and VH sequences of 1150/1151 and CP-870,893 are known from the prior art (see above). The sequences of the other scFv clones converted to IgG2 format are not shown.

Example 4

Kinetic Measurements of Eleven Anti-CD40 hIgG2 Antibodies

The kinetic constants of 11 of the IgG2 antibodies against human CD40 (produced in Example 3) were determined by surface plasmon resonance (SPR) using a single cycle kinetic (SCK) approach. Also, cross-species binding was assessed to both mouse CD40 (mCD40) and cynomolgus CD40 (cCD40).

Materials and Methods

The kinetic constants were determined by SPR on a BIAcore T200 instrument (GE Healthcare) using single cycle kinetics (SCK) or a single injection approach.

An α-kappa antibody (GE Healthcare #28958325), functioning as a capture ligand, was immobilised by EDC/NHS chemistry onto all 4 surfaces of a CM5-S amine sensor chip according to the manufacturer's recommendations. Protein A-purified IgG2 antibodies (Example 3) were injected and captured on the chip surface, aiming for equal response units (RU) between clones.

A 3-fold dilution series of hCD40-avi and 4-fold dilution series of hCD40-Fc and cCD40-Fc, consisting of 5 concentrations ranging from 100 nM-1.2 nM and 80 nM-0.31 nM, respectively, were prepared in running buffer (HBS supplemented with 0.05% Tween20 at pH 7.5) and sequentially injected over the chip surfaces. Following a dissociation phase, the surfaces were regenerated with 10 mM glycine-HCl, pH 2.1. Single concentration injections at 80 nM were also made with mCD40. Details on the CD40 proteins used in this study are given in Table 1.

By subtracting the response curve of a reference surface (an α-kappa antibody immobilised surface), response unit sensorgrams for all antibodies were obtained. Reaction rate kinetics constants were calculated using the Biacore T200 Evaluation Software 3.1 and the 1:1 Langmuir binding model.

TABLE 1

| | | | |
|---|---|---|---|
| CD40 reagents | | | |
| Name | Short name | Source | Characteristics |
| Bio-tinylated human CD40 | hCD40-avi | Aero Biosystems #CD0-H82E8 | Produced in HEK293 cells; Biotinylated on C-terminal avi-tag. CD40 amino acids: E21-R193 (Accession# P25942-1) |
| Human CD40 Fc chimera | hCD40-Fc | RnD Systems (#1493-CDB) | Produced in mouse myeloma cell line; Fc-chimera (disulfide-linked homodimer) CD40 amino acids: E21-R193 (Accession# P25942-1) |
| Cyno-molgus CD40 Fc chimera | cCD40-Fc | RnD Systems (#9660-CD) | Produced in HEK293 cells Fc-chimera (disulphide-linked homodimer) CD40 amino acids: E21-R193 (Accession # XP 005569274.1) |
| Mouse CD40 | mCD40 | Aero Biosystems #TN5-M52H8 | Produced in HEK293 cells. CD40 amino acids: V24-R193 (Accession# P27512-1) |

Results

Equal capture levels (RU) were obtained for all antibodies. Following injection of analyte, chip surfaces were successfully regenerated leaving an active surface ready for the next antibody-capture cycle. See Table 2 for summary of determined kinetic constants and affinities.

It is important to remember that two of the antigens used here are Fc-fused and these will therefore combine and form homodimers. Binding strength is traditionally reported by the affinity constant ($K_D$). However, this constant is used to describe the strength of a monovalent interaction and given that the Fc-fused antigens most likely interact with the antibody surface in a bivalent fashion, thereby potentially giving rise to synergy and an apparent increase in affinity, we instead report the apparent affinity (denoted as $^{app}K_D$).

The avidity contribution of an interaction will not only depend on the antigen being a monomer or a dimer but also on the antibody itself. Binders specific for one and the same antigen may have very different avidity effects due to differences in binding kinetics. Despite the potential avidity contribution for some of the binders, we have chosen a Langmuir 1:1 binding model for calculation of $^{app}K_D$ for the interaction with both hCD40-fc and cCD40-Fc This was considered to provide an average picture that allowed us to, in a pragmatic way, to select the best binders to move forward with.

As expected, all antibodies showed binding towards the human CD40 proteins. Some clones however, only displayed binding towards hCD40-Fc and no binding towards hCD40-avi (or too low a binding response for kinetic measurements). The $^{app}K_D$ for binding to hCD40-Fc were in the range of 5-20 nM for all Y-SM083 antibodies, whereas the corresponding values for hCD40-avi was considerable higher. This discrepancy can most likely be explained by the fact that hCD40-Fc is a dimer, which can potentially give rise to an avidity effect (accumulated strength of multiple affinities). All antibodies, except Y-SM083-B1 and –G2, also showed cross-binding to cynomolgus CD40-Fc. Binding to mouse CD40 could not be detected for any of the antibodies, which is somewhat expected given the relatively low sequence homology (58%) between human and mouse CD40.

TABLE 2

| Antibody Kinetic Parameters | | | |
|---|---|---|---|
| | Human CD40-avi | | |
| Clone Name | ka (1/Ms) | kd (1/s) | $K_D$ (M) |
| Y-SM083-F4 | ** | ** | ** |
| Y-SM083-A9 | 1.7E+05 | 6.1E–03 | 3.7E–08 |
| Y-SM083-B8 | 4.5E+09 | 6.9E+01 | 1.5E–08 |
| Y-SM083-B3 | ** | ** | ** |
| Y-SM083-A1 | ** | ** | ** |
| Y-SM083-B1 | ** | ** | ** |
| Y-SM083-F7 | ** | ** | ** |
| Y-SM083-E7 | 2.5E+05 | 1.1E–02 | 4.4E–08 |
| Y-SM083-G2 | -- | -- | -- |
| X-SM083-ab-2 | 7.5E+05 | 1.4E–01 | 1.8E–07 |
| X-SM083-ab-5 | 6.2E+04 | 1.1E–03 | 1.8E–08 |
| | Human CD40-Fc* | | |
| Clone Name | ka (1/Ms) | kd (1/s) | $^{app}K_D$ (M) |
| Y-SM083-F4 | 5.3E+05 | 4.0E–03 | 7.6E–09 |
| Y-SM083-A9 | 3.1E+05 | 1.6E–03 | 5.1E–09 |
| Y-SM083-B8 | 1.2E+05 | 1.5E–03 | 1.3E–08 |
| Y-SM083-B3 | 2.2E+09 | 4.4E+01 | 2.0E–08 |
| Y-SM083-A1 | 8.1E+04 | 1.4E–03 | 1.7E–08 |
| Y-SM083-B1 | 9.0E+04 | 1.8E–03 | 2.0E–08 |
| Y-SM083-F7 | 1.0E+06 | 5.9E–03 | 5.8E–09 |
| Y-SM083-E7 | 1.5E+05 | 9.1E–04 | 6.3E–09 |
| Y-SM083-G2 | 6.5E+05 | 5.0E–03 | 7.8E–09 |
| X-SM083-ab-2 | 3.2E+05 | 1.4E–03 | 4.6E–09 |
| X-SM083-ab-5 | 6.6E+04 | 3.2E–05 | 4.8E–10 |

TABLE 2-continued

| Antibody Kinetic Parameters | | | |
|---|---|---|---|
| | Cynomolgus CD40-Fc* | | |
| Clone Name | ka (1/Ms) | kd (1/s) | $^{app}K_D$ (M) |
| Y-SM083-F4 | 4.9E+05 | 3.9E–03 | 8.1E–09 |
| Y-SM083-A9 | 5.0E+05 | 2.2E–03 | 4.5E–09 |
| Y-SM083-B8 | 9.5E+09 | 1.3E+02 | 1.3E–08 |
| Y-SM083-B3 | ** | ** | ** |
| Y-SM083-A1 | ** | ** | ** |
| Y-SM083-B1 | -- | -- | -- |
| Y-SM083-F7 | ** | ** | ** |
| Y-SM083-E7 | 1.5E+05 | 1.9E–03 | 1.3E–08 |
| Y-SM083-G2 | -- | -- | -- |
| X-SM083-ab-2 | 4.9E+05 | 1.8E–03 | 3.8E–09 |
| X-SM083-ab-5 | 9.1E+04 | 2.5E–05 | 2.8E–10 |

-- No binding was detected.
*Avidity effects may contribute to kinetic values and therefore, $^{app}K_D$ rather than $K_D$ is given for these antigens.
** Binding detected but too low a binding response (RU) and/or too fast on (ka) and off (kd) rates to determine kinetic parameters.

Example 5

Assessment of Binding to Canine CD40 by Surface Plasmon Resonance

In Example 4, cross-species binding for a set of novel anti-CD40 antibodies was assessed to both mouse CD40 (mCD40) and cynomolgus CD40 (cCD40). In this Example, a subset of the same antibodies was analyzed for binding to canine CD40 (caCD40) by surface plasmon resonance (SPR).

Materials and Methods

The SPR experiments were run on a BIAcore T200 instrument (GE Healthcare) using a single cycle kinetics (SCK) approach. An α-Fab antibody (GE Healthcare #28958325), functioning as capture ligand, was immobilized through EDC/NHS chemistry onto all four surfaces of a CM5-S amine sensor chip according to the manufacturer's recommendations. Seven Protein A purified IgG2 antibodies from Example 3 (Y-SM083-A1, Y-SM083-A9, Y-SM083-B1, Y-SM083-B8, Y-SM083-F7, X-SM083-Ab-2, X-SM083-Ab-5) were injected and captured onto the chip surface, aiming for equal response units (RU) between clones (400-500 RU). A five-fold dilution series of hCD40-Fc (Sino Biological, #10774-H38H) and caCD40-Fc (Sino Biological, #70105-D02H) at five concentrations ranging between 0.16-100 nM was prepared in running buffer (HBS supplemented with 0.05% Tween-20 at pH 7.5) and sequentially injected over the chip surfaces, using an association time of 120 seconds. Following a dissociation phase of 600 seconds, the surfaces were regenerated with 10 mM glycine-HCl, pH 2.1.

In order to get a more reliable determination of the kinetic constants for CP-870,893 (X-SM083-Ab-5), the experimental parameters were optimized in a follow-up experiment. Here, the antibody capture levels were decreased from approximately 400 to 200 RU, the antigen concentration range was decreased to 0.62-50 nM (five concentrations, three-fold dilution series), and the association and dissociation time increased to 240 and 1200 seconds, respectively. By subtracting the response curve of a reference surface having an α-kappa antibody immobilized thereto, response unit sensorgrams for all antibodies were obtained. Data was analysed using the software BIAeval v.3.1 (GE Healthcare).

Results

As expected, all analysed antibodies showed binding towards human CD40. The obtained sensorgrams (data not shown) looked similar to those obtained previously, and kinetic parameters were similar to those reported in Table 2. In contrast, only one of the antibodies, namely X-SM083-Ab-5 (CP-870,893), also exhibited binding to canine CD40. However, the affinity of Ab-5 for canine CD40 was approximately 10 times lower than for the human orthologue (0.2 vs 2.5 nM), which is mainly due to a faster dissociation time for the former interaction. In Table 3, the obtained kinetic parameters for Ab-5 (CP-870,893) towards human and canine CD40 are given. Both antigens are Fc fusions and hence dimeric, so will most likely give rise to kinetic constants with avidity effect contributions. Therefore, $^{app}K_D$ rather than $K_D$ is given. Despite the potential avidity contribution, we selected a Langmuir 1:1 binding model for calculation of $^{app}K_D$ for the interaction to both human and canine CD40.

TABLE 3

|  | $K_a$ (1/Ms) | $k_d$ (1/s) | $^{app}K_D$ (nM) | Model |
|---|---|---|---|---|
| Human CD40-FC | 1.9E+05 | 3.6E−05 | 0.2 | 1:1 Binding |
| Canine CD40-Fc | 1.7E+05 | 4.1E−04 | 2.5 | 1:1 Binding |

Conclusions

The difference in cross-species binding between the different anti-CD40 antibodies can most likely be explained by difference in epitope. The CD40 ligand inhibition experiment presented below in Example 6 grouped X-SM083-Ab-5 and Y-SM083-A9 together, as they were the only two antibody candidates that were seemingly unaffected by the presence of CD40 ligand. Nevertheless, the data presented here show that only Ab-5 (CP-870,893) binds canine CD40, which suggest that these antibodies bind to different epitopes on CD40. Surprisingly, and contradictory to the finding here, the inventors in US2006-0093600 state that CP-870,893 does not bind to canine (dog) CD40. The reason for the discrepancy between what is reported in US2006-0093600 and the results of this SPR study is currently not known.

Example 6

CD40 Ligand Inhibition

This experiment describes, using an SPR-based approach, blocking of/interference with the interaction between CD40 ligand (CD40L) and human CD40 by eleven anti-CD40 antibodies.

Materials and Methods

An α-human Fab antibody (GE Healthcare #28958325), functioning as a capture ligand, was immobilised onto all four surfaces of a CM5-S amine chip according to manufacturer's recommendations. Eleven anti-CD40 antibodies (listed in Table 2 in Example 4) were injected and captured on the chip surface, aiming for equal response units (RU) between clones. Human CD40-Fc (RnD systems #1493-

CDB) was diluted to 20 nM in running buffer (HBS supplemented with 0.05% Tween20) and injected either alone or pre-incubated with 10 times molar excess of human CD40 ligand (RnD Systems #6420-CL). A single injection of 200 nM CD40 ligand alone was also performed. Following a dissociation phase, the chip surfaces were regenerated with 10 mM glycine-HCl, pH 2.1. The anti-NP antibody B1-8 (Example 3) was included as a negative control.

By subtracting the response curve of a reference surface (an α-human Fab antibody immobilised surface), response sensorgrams and binding levels (response units (RU)) for each antibody interacting with hCD40-Fc alone or pre-incubated with CD40L could be retrieved. Data was analysed using software BIAeval v.3.1 (GE Healthcare).

Results

An α-human Fab antibody mix was successfully immobilised on all four surfaces of the chip and similar capture levels could be obtained for all antibody clones. Following injection of analyte, chip surfaces could successfully be regenerated leaving an active surface ready for the next antibody-capture cycle.

Figure 1:
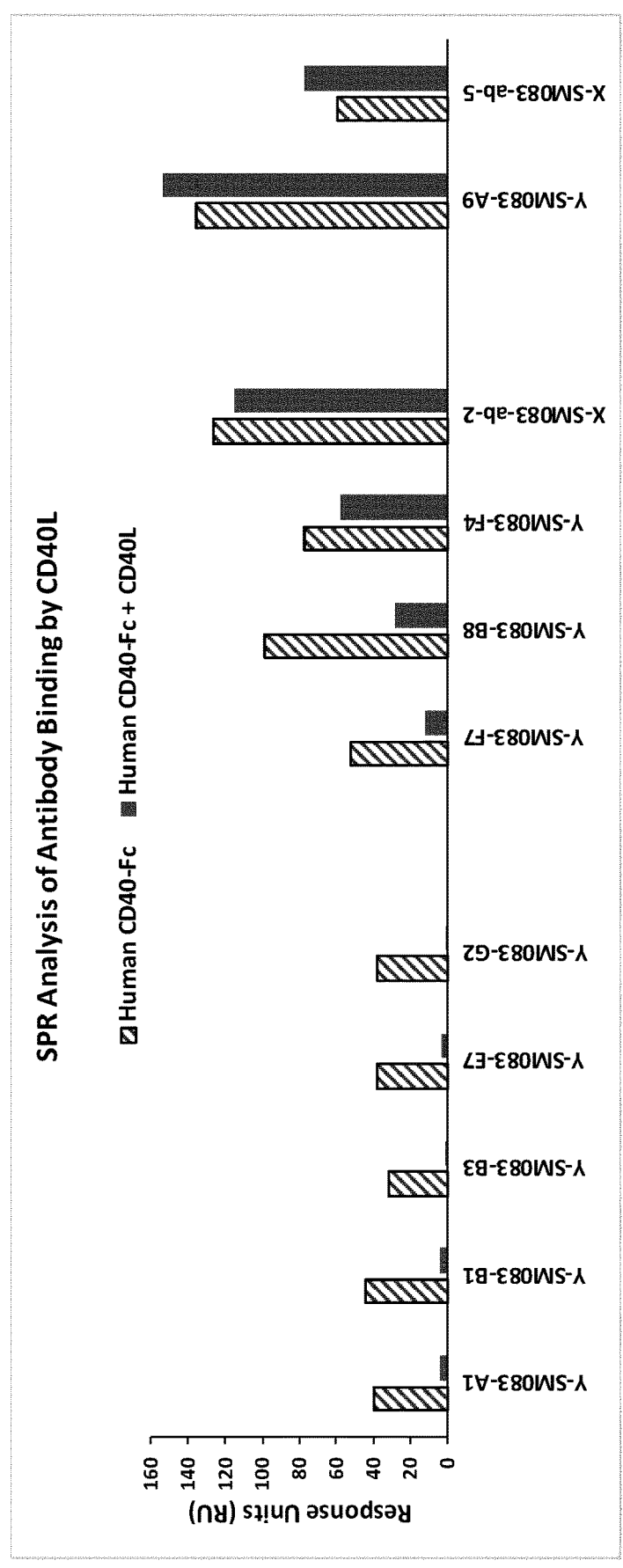
FIG. 1 shows the binding of 11 anti-CD40 antibodies to CD40 (as measured by SPR) in the presence and absence of CD40L. A reduction in binding to CD40 in the presence of CD40L indicates that the interaction between CD40 and CD40L interferes with binding of that antibody to CD40.

Obtained binding units (RU) for each antibody towards CD40-Fc were compared with obtained binding units for CD40-Fc pre-incubated with CD40 ligand (FIG. 1). It was shown that nine of the clones displayed reduced binding to CD40-Fc with CD40 ligand present, whereas binding of two of the antibodies (X-SM083-ab-5 and Y-SM083-A9) seemed to be unaffected by the presence of CD40 ligand. Among the clones displaying a reduction in binding, five were more or less completely blocked (Y-SM083-A1, -B1, -B3, -E7 and -G2), while four were only partially blocked by the presence of the ligand (Y-SM083-F7, -B8, -F4 and X-SM083-ab-2).

As expected, BI-8 hIgG2 did not display binding towards CD40-Fc, nor towards CD40-Fc pre-incubated with CD40 ligand or CD40 ligand alone (data not shown).

Conclusions

The data obtained here is largely consistent with what has been described in the literature. Yu et al. (*Cancer Cell* 33(4): 664-675, 2018) demonstrated that the agonistic antibody CP-870,893 i.e. the antibody referred to here as X-SM083-ab-5, binds the membrane-distal cysteine-rich domain 1 (CRD1) of CD40 without blocking CD40 ligand interaction. Similarly, the epitope of X-SM083-ab-2 (1150/1151) has been reported as located in this domain. No competition between this antibody and CD40 ligand was observed in previous studies (WO 2015/091853). In contrast, here, we do observe a small effect on antibody binding when ligand is present. The discrepancy could be explained by the different methods used.

Example 7

Agonistic Activity of Novel Binders

The agonistic activity of eleven CD40 binders selected for continued study was tested, as determined by their ability to activate dendritic cells. Dendritic cell activation was assessed based on the up-regulation of activation markers and IL-12 expression in response to antibody binding.

Materials and Methods

Human Monocyte-Derived DC (MoDC) Differentiation

Peripheral blood mononuclear cells (PBMCs) were isolated from buffy coats, donated by healthy volunteers, by Ficoll separation using SepMate (85450, Stemcell Technologies) together with cell density gradient Ficoll®-Paque Premium (17-5442-02, GE Healthcare) according to the manufacturer's protocol. Further separation of CD14$^{Pos}$ (CD14$^+$) monocytes was performed by positive selection using MACS cell separation CD14+ beads according to the manufacturer's protocol.

Solutions and cells were kept on ice for the duration of the isolation with wash steps performed in PBS (0.5% BSA, 2 mM EDTA). Purity of the isolated CD14+ cell fraction was evaluated by flow cytometry (for CD14 expression). Isolated CD14+ monocytes were cultured with a density of $4 \times 10^5$ cells/ml in ø10 cm tissue-treated culture plate. The cells were cultured for six days in RPMI medium supplemented with 10% FBS, 1% Pen-Strep, 1% HEPES and 0.2% β-mer-captoethanol supplemented with 150 ng/ml hGM-CSF (Pre-Protech) and 50 ng/ml IL-4 (PreProtech) at 37° C. in 5% CO$_2$. Half of the medium was exchanged with complete medium supplemented with hGM-CSF (150 ng/ml) and IL-4 (50 ng/ml) at day 3 and day 5.

MoDC Activation

Following on from above, on day 6, cultured monocytes were harvested and their differentiation status evaluated by flow cytometry by staining for CD14 and CD1a. DC activation was performed in a 96-well TCT plate (Standard F, Sarsted) with $1 \times 10^5$ immature MoDC seeded per well in complete medium supplemented with hGM-CSF and IL-4 (concentrations used as previously described) using a panel of different anti-CD40 antibodies. 1:2 serial dilutions were performed starting from 500 nM. Supernatant was collected after 48 h of culture for IL-12 ELISA and cells were analysed by flow cytometry for surface marker expression.

Flow cytometry analysis was performed by staining of extracellular expression of CD14-APC-Cy7 (HCD14), HLA-DR-PE-Cy5 (L243), CD86-BV421 (IT2.2), CD40-FITC (5C3), CD1a-PE (H1149) and CD83-APC (HB15e). All antibodies were purchased from BioLegend. The cells were incubated with the antibodies for 20 min at 4° C. and thereafter washed with PBS containing 3 mM EDTA and centrifuged for 5 min at 1500 rpm.

tSNE Analysis

T-Distributed Stochastic Neighbor Embedding (t-SNE) was performed on the flow cytometry data (Rtnse package in R; van der Maaten and Hinton (2008), J Mach Learn Res 9:2579-2605; van der Maaten (2014), J Mach Learn Res 15:3221-3245) to identify antibodies with similar properties to previously validated Ab1 (X-SM083-Ab-1) and Ab2 (X-SM083-Ab-2). LPS was used as an additional positive control. MFI (mean fluorescence intensity) values from the CD14-APC-Cy7 (HCD14), HLA-DR-PE-Cy5 (L243), CD86-BV421 (IT2.2), CD40-FITC (5C3), CD1a-PE (H1149) and CD83-APC (HB15e) panel were used as variables when performing the analysis. Scaling was performed for each marker prior to t-SNE analysis. Perplexity was set to 2 in all analyses.

IL-12 ELISA

The ELISA was performed using the human IL-12p40 ELISA Maxi kit (430704, BioLegend). Costar high binding 96-well plates (Sarstedt) were coated with human IL-12p40 capture antibodies. Plates were blocked with 1× Assay Diluent A for 1 h on a shaking table (500 rpm). All incubations were at RT with shaking. Washing was performed 4 times with 300 µl/well of PBS containing 0.05% Tween-20 (Sigma-Aldrich). The washing procedure was repeated after each step if not stated otherwise. The samples were diluted in 1× Assay Diluent A, as for the standard. IL-12 standard was diluted 1:1 with a starting concentration of 4000 µg/ml. The samples and standard were added to the plate and incubated for 2 h. Subsequently, the plate was incubated with 1× detection antibody (100 µl/well) for 1 h. Lastly, 1× Avidin-HRP solution (100 µl/well) was added to all wells and incubated for 30 min at RT with shaking. Plates were washed 5 times, soaked for 30-60 s per wash. TMB solution (100 µl/well) was added and incubated for 15 min before reactions were stopped with an equal amount of 1 M H$_2$SO$_4$. Absorbance was measured at 450 nM with FLUO-star Omega (BMG Labtech).

Results

Figure 2:
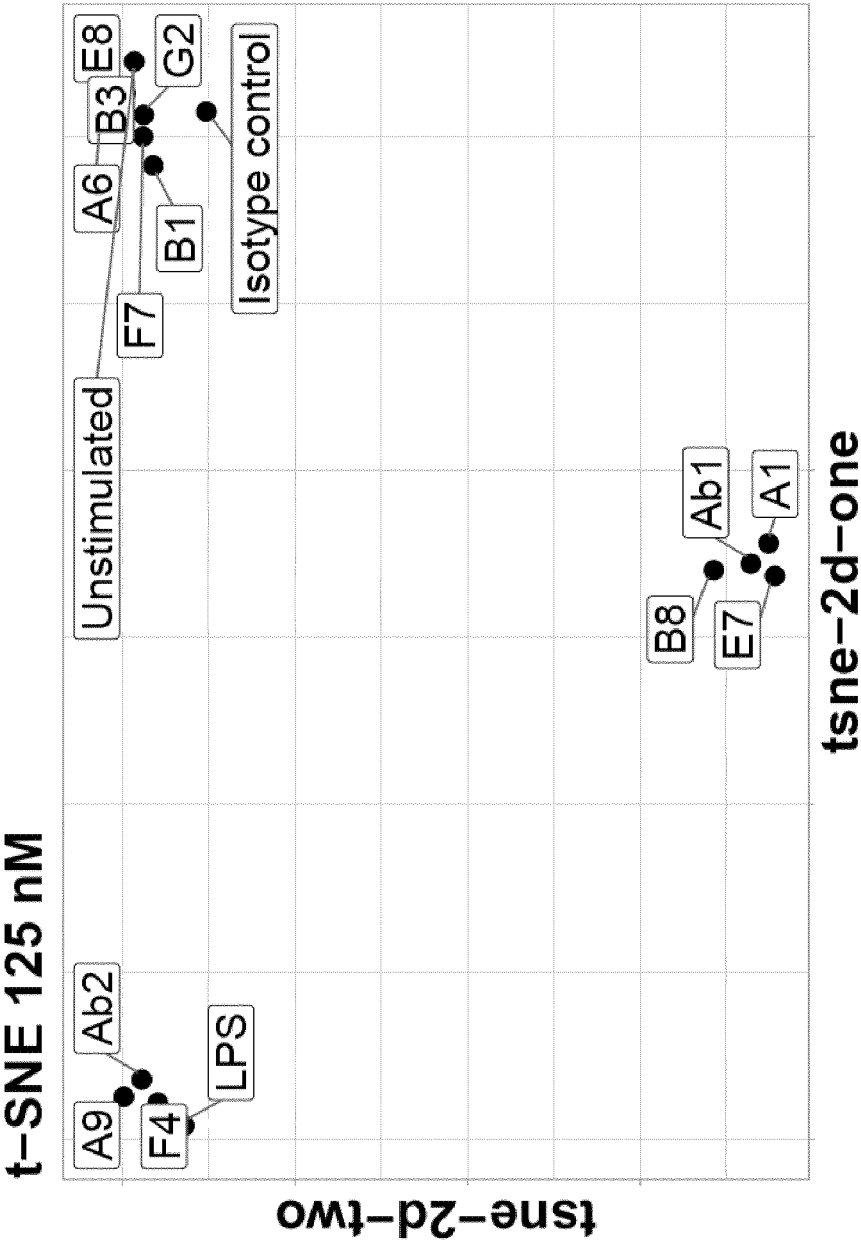
FIG. 2 shows a t-SNE FACS analysis of aggregated data for surface expression of CD14, CD1a, CD40, HLA-DR, CD86 and CD83 after 48 hours of stimulation with various anti-CD40 antibodies. The antibodies tested could be divided into three clusters: non-agonistic including an IgG2 isotype control, intermediate agonists including Ab1 (i.e. 1150/1151 with IgG1 isotype) and strong agonists including Ab2 (i.e. 1150/1151 with IgG2 isotype) and the LPS control. Of the novel antibodies disclosed herein, only the A9 and F4 antibodies showed potent agonistic potential.

The result of the tSNE analysis is shown in FIG. 2 for a concentration of stimulating antibodies of 125 nM. Aggregated data on the surface expression of CD14, CD1a, CD40, HLA-DR, CD86 and CD83 after 48 hours of stimulation leads to three clusters: one cluster of cells that are not stimulated, one cluster with an intermediate activation profile (clustering with Ab1, i.e. 1150/1151 of IgG1 isotype) and one cluster with a potent agonistic profile (clustering with LPS and Ab2, i.e. 1150/1151 of IgG2 isotype). The A9 and F4 antibodies show potent agonistic potential. Several antibodies are intermediate agonists and a number show no agonistic activity.

Figure 3:
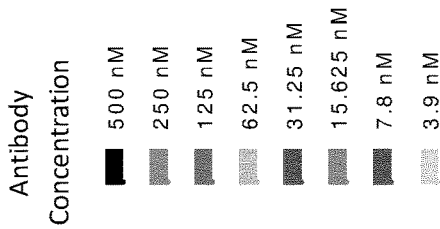
FIG. 3 shows IL-12 production by dendritic cells stimulated with a variety of anti-CD40 antibodies at a range of concentrations (listed in legend), as measured by ELISA.
Figure 3:
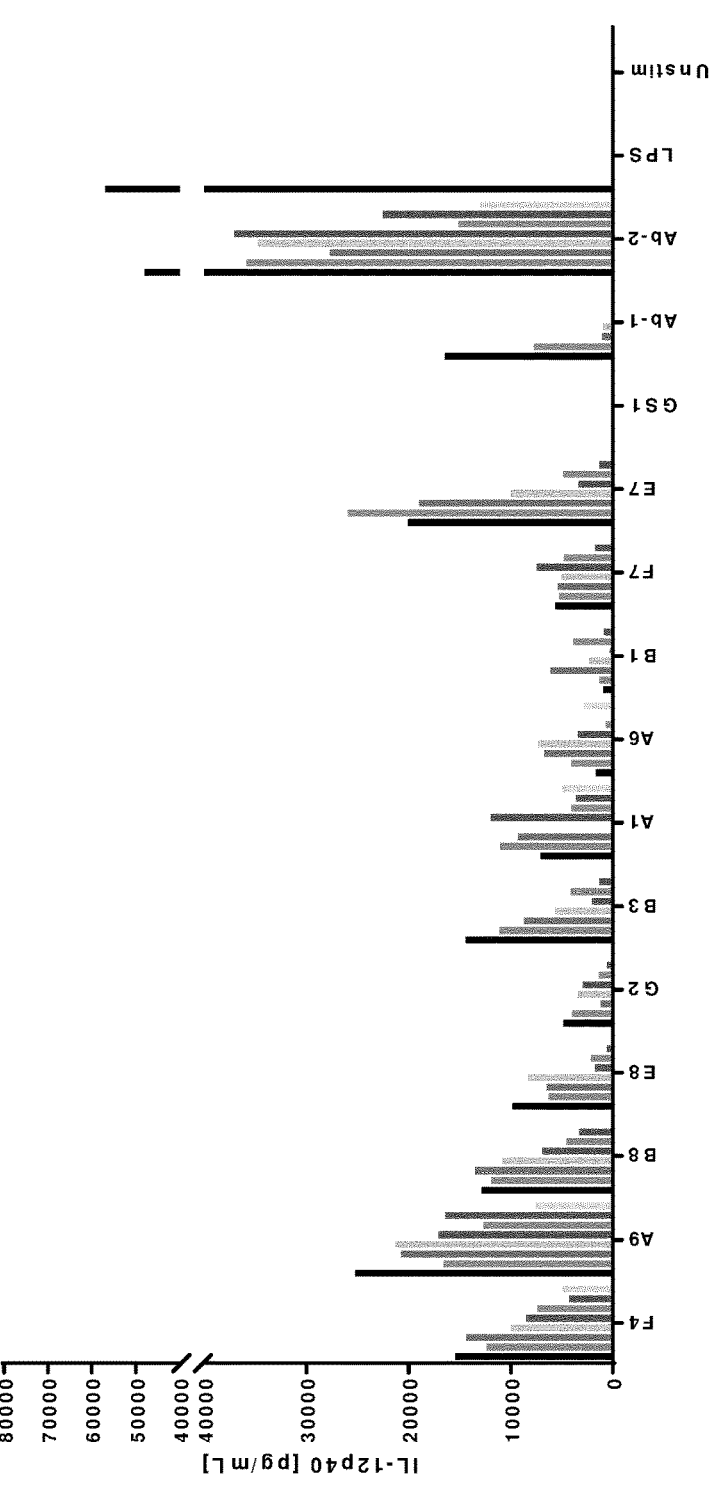

The results of the IL-12 ELISA are similar (FIG. 3). By this measure A9 and E7 appeared to have the highest agonistic activity of the new antibodies. The other new antibodies tested displayed low or moderate levels of agonistic activity. As the antibody displaying the highest level of agonistic activity across the two experiments, A9 was selected as lead candidate.

Example 8

Epitope Mapping by HDX-MS

In this Example hydrogen-deuterium exchange mass spectrometry (HDX-MS) was performed on the Y-SM083-A9 antibody together with human CD40 in order to map its epitope.

When proteins are dissolved in a buffer containing heavy water (D$_2$O), their hydrogen atoms attached to heteroatoms (e.g. in the context of —OH, —NH or —SH groups) are replaced by deuterium. The degree of deuterium incorporation can be monitored by MS since each D atom is one mass unit heavier than an H atom. Additionally, when deuterium labelling is further combined with enzymatic proteolysis, the deuteration profile of different areas within the protein can be monitored. Binding of a ligand to a protein target produces local changes in hydrogen bonding, e.g. structure stabilisation or destabilisation, and thus the HDX-MS technique can be used to identify the binding interfaces of protein complexes.

Materials and Methods

4 µl of a 0.92 mg/ml hCD40-Fc (RnD Systems, #1493-CDB) solution in PBS was mixed with 105.7 µl of 1 mg/ml Y-SM083-A9 for a 1:1 molar ratio. The CD40/antibody complex was concentrated to 36 µl using a 10K Centrifugal filter unit (Amicon Ultra, Merck). In parallel, a sample containing hCD40-Fc only, without the addition of antibody, was prepared analogously. The samples were analysed in an automated HDX-MS system (CTC PAL/Biomotif HDX) in which samples were automatically labelled, quenched, digested, cleaned and separated at 2° C. More specifically, samples were labelled by mixing 4 μl of hCD40-Fc (or hCD40-Fc/antibody complex) with 24 μl of deuterated PBS and incubated at 4° C. for three labelling time points: 10 min, 25 min and 60 min.

The labelling reaction was stopped/quenched by decreasing the pH to ~2.3 and temperature to ~4° C. through the addition of 25 μl of a solution containing 6 M Urea, 417 mM TCEP and 0.5% TFA. Samples were digested using an immobilised pepsin column (2.1 column (2.1×30 mm) at 60 μl/min for 2 min, followed by an on-line desalting step using a 2 mm I.D×10 mm length C-18 pre-column (ACE HPLC Columns, Aberdeen, UK) using 0.2% formic acid at 400 μl/min for 1 min. Peptic peptides were then separated by an 18 min 8-55% linear gradient of ACN in 0.1% formic acid using a 2 mm I.D×50 mm length HALO C18/1.8 μm analytical column operated at 60 μl/min. An Orbitrap Q Exactive mass spectrometer (Thermo Fisher Scientific) operated at 70,000 resolution at m/z 400 was used for analysis. The software Mascot was used for peptide identification and HDExaminer (Sierra Analytics, USA) was used to process all HDX-MS data. Statistical analysis was performed using a 95% confidence interval.

Results

The deuteration kinetics of 25 peptides were followed by HDX-MS covering 50% of the protein construct. Deuterium labelling (10, 25 and 60 min) and differential deuteration uptake kinetics between CD40 alone and in the presence of Y-SM083-A9 were calculated. Peptides close to the N-terminus showed statistically lower deuterium uptake in the presence of Y-SM083-A9 antibody, mapping the epitope to this region (Table 4).

TABLE 4

CD40 Peptides with Lowered Deuterium Exchange Identified by HDX-MS

| Peptide | Amino Acid Positions | Sequence | SEQ ID NO: |
|---|---|---|---|
| 1 | 21-30 | EPPTACREKQ | 63 |
| 2 | 21-32 | EPPTACREKQYL | 64 |
| 3 | 58-67 | ECLPCGESEF | 65 |

Peptides 1 and 2 are overlapping and located in the N-terminus of CRD1 of CD40 and peptide 3 is located in the N-terminus of CRD2 (or in the bridging sequence between CRD1 and CRD2, depending on how this is defined). It is possible that these constitute two parts of a conformational epitope recognised by A9.

Example 9

Epitope Mapping by Comparison with the Anti-CD40 Antibody 5C3

In this Example, flow cytometry and competitive binding are used to compare the CD40 epitope bound by the novel antibody A9 with that of known antibody CP-870,893 (Ab-5), using the known CD40-binding antibody 5C3 with a fluorescent label as a reference. If 5C3 staining does not occur after cells have been treated with the A9 or Ab-5 antibody, it means that there is a steric hindrance which prevents simultaneous binding. In other words, if there is no 5C3 staining after exposure to a tested candidate antibody, it would indicate that the tested antibody and 5C3 share similar epitopes on the CD40 receptor.

Materials and Methods

PBMC were isolated as in Example 7. In this Example, the CD14 negative cell fraction was used for incubation with 25 nM-50 nM of the antibodies A9 and Ab-5 for 30 min on ice to let the antibodies bind their target without internalisation. After terminated incubation, the cells were washed once with cold PBS, and then stained with CD3-BV510 (clone: UCHT1), CD19-APC (clone: H1149) and CD40-FITC (clone: 5C3) as described in Example 7. The cells were analysed in a Cytoflex flow cytometer (Beckman Coulter), and then the CD19+ cells were gated out to investigate CD40 expression. The experiment was performed on two separate donors, both stained with the same labelled anti-CD40 clone (5C3) and using the same experimental setup.

Results

Figure 4:
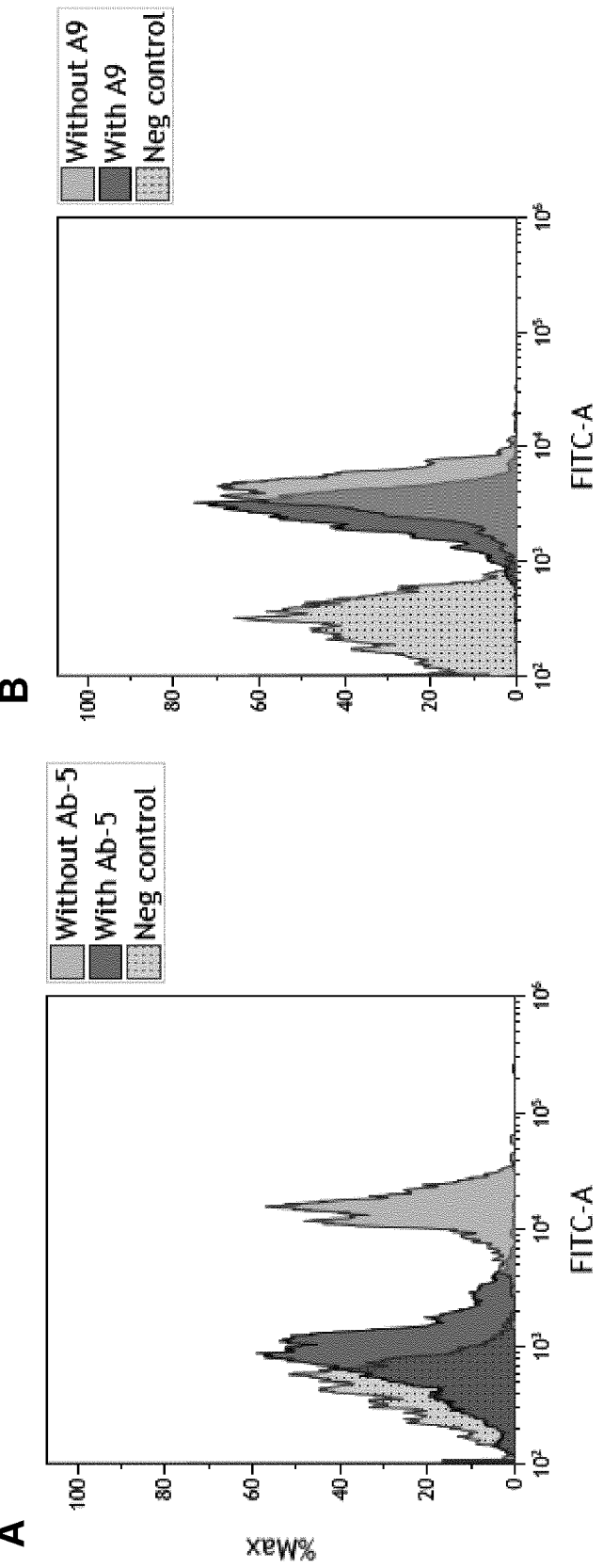
FIG. 4 is a pair of FACS histograms showing detection of staining with the anti-CD40-FITC antibody 5C3. The light grey histograms display staining only with 5C3 on CD19+ cells. The dark grey histograms display 5C3 staining after pre-incubation with non-labelled CD40-binding antibodies Ab-5 (A) or A9 (B). The dotted grey histogram displays unstained CD19+ cells as negative control background reference.

In FIG. 4, light grey histograms display detection of the anti-CD40 antibody (5C3) in comparison with unstained CD19$^+$ cells. In FIG. 4A, the dark grey histogram shows staining with 5C3 after pre-incubation with the Ab-5 antibody. In FIG. 4B, the dark grey histogram shows staining with 5C3 after pre-incubation with the A9 antibody instead. As seen in FIG. 4A, pre-staining with Ab-5 leads to loss of the FITC signal (a histogram which is similar to the negative control). Conversely, FIG. 4B shows that pre-incubation with A9 retained the FITC signal from 5C3. The loss of signal seen with the Ab-5 clone is likely due to shared epitope binding with the staining 5C3 antibody, leading to competition upon binding of Ab-5. Pre-incubation with the A9 antibody, however, did not lead to blockage of the 5C3 antibody binding, which indicates that A9 and 5C3 do not share the same binding epitope on CD40.

Conclusion

The results indicate that the known antibody Ab-5 (CP-870,893) and the novel antibody A9 do not share the same CD40 binding epitope, because Ab-5 blocks binding of the labelled 5C3 antibody, while A9 does not.

Example 10

Internalisation of the A9 Antibody

In the context of the present invention, internalisation of an agonistic CD40 antibody is of great importance for its ability to deliver a cargo in the bispecific format. This Example studies the ability of the novel A9 antibody to be internalised into dendritic cells (DCs).

Materials and Methods

MoDCs were isolated and cultured as described in Example 7. At day 6, the cells were harvested and re-plated into two 96-well tissue treated plates and incubated for 2 h at 37° C. with 5% $CO_2$. The test antibodies Ab-2 and A9 were then added at a concentration of 125 nM and incubated on ice for 30 min to allow receptor binding. The cells were then washed three times with cold, serum-free RMPI and centrifuged at 250 g for 5 min at 4° C. The supernatant was discarded between washes. The cells were resuspended in warm complete medium for internalisation and in cold medium for use in a control plate. One plate was incubated at 4° C. the whole time and one plate was incubated at 37° C. with 5% $CO_2$. The incubation was terminated at different time-points from 5 min to 4 h by addition of cold PBS. Antibodies bound to the surface of cells were then detected through staining with an anti-kappa-APC (cat no:9230-11, Biolegend) antibody for 30 min at 4° C. before analysis with flow cytometry (Cytoflex). The degree of internalisation was calculated as follows:

$$\frac{(MF1 \text{ at } 37° \text{ C.} - MF1 \text{ from secondary } Ab \text{ only at } 4° \text{ C.})}{(MF1 \text{ at } 4° \text{ C.} - MF1 \text{ from secondary } Ab \text{ only at } 4° \text{ C.})} \times 100$$

Result

Figure 5:
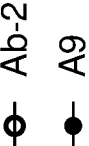
FIG. 5 is a diagram showing the internalisation pattern of the A9 antibody (black circles) and the Ab-2 antibody (1150; white circles) over a time period from 5 min to 4 h using human monocyte-derived dendritic cells.
Figure 5:
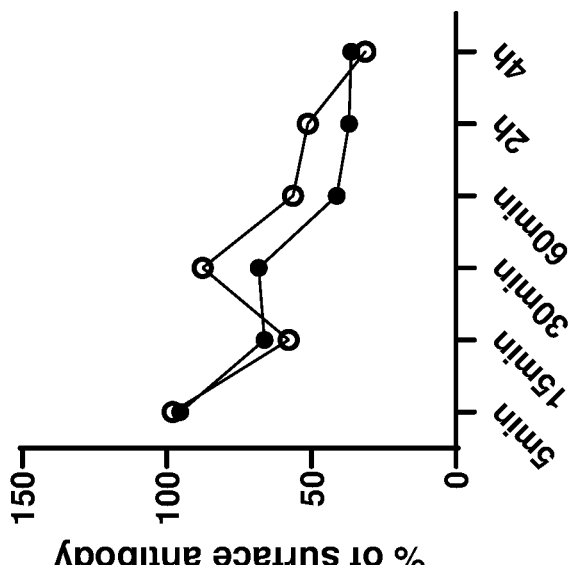

The internalisation of the A9 (monoclonal IgG2) antibody was compared to the Ab-2 antibody (1150 as monoclonal IgG2). As shown in FIG. 5, the internalisation patterns of the two antibodies were similar, with a slow internalisation over time reaching 50% internalisation after 60 min. Approximately 30% of the antibodies remained extracellular after 4 h incubation. To conclude, internalisation of the novel A9 antibody occurs slowly over a period of several hours and is comparable to internalisation of the known Ab-2 antibody (1150).

Example 11

Design and Generation of Bispecific Antibodies (Conjugates)

A number of bispecific antibodies (bispecific conjugates) based on A9 were generated. For comparison, bispecific antibodies based on B8, which displays moderate agonistic activity, were also generated. Details of the bispecific antibodies generated are set forth in Table 5.

TABLE 5

| | Bispecific Antibodies | | | | |
|---|---|---|---|---|---|
| | Anti-CD40 IgG | Subclass | scFv | scFv Append-ing Position | Link-er |
| X-SM083-bi-21 | Y-SM083-A9 | IgG2 | 14GIIICII-b | CH3 | $(G_4S)_2$ |
| X-SM083-bi-22 | Y-SM083-A9 | IgG2 | 14GIIICII-b | CL | $(G_4S)_2$ |
| X-SM083-bi-23 | Y-SM083-A9 | IgG2 | FITC8 | CH3 | $(G_4S)_2$ |
| X-SM083-bi-24 | Y-SM083-B8 | IgG2 | 14GIIICII-b | CH3 | $(G_4S)_2$ |
| X-SM083-bi-25 | Y-SM083-B8 | IgG2 | 14GIIICII-b | CL | $(G_4S)_2$ |
| X-SM083-bi-26 | Y-SM083-B8 | IgG2 | FITC8 | CH3 | $(G_4S)_2$ |
| X-SM083-bi-28 | Y-SM083-A9 | IgG2 | FITC8 | CL | $(G_4S)_2$ |
| X-SM083-bi-29 | Y-SM083-A9 | IgG2 C127S | FITC8 | CH3 | $(G_4S)_2$ |
| X-SM083-bi-30 | Y-SM083-A9 | IgG2 C127S | FITC8 | CL | $(G_4S)_2$ |
| X-SM083-bi-31 | Y-SM083-A9 | IgG2 C127S | FITC8 | CH3 | $G_4S$ |
| X-SM083-bi-32 | Y-SM083-A9 | IgG2 C127S | FITC8 | CH3 | $(G_4S)_4$ |
| X-SM083-bi-33 | Y-SM083-A9 | IgG2 C127S | FITC8 | CL | $(G_4S)_2$ |

The 14GIIICII-b scFv is described above, and binds a known B cell epitope derived from tetanus toxin and denoted MTTE. The FITC8 scFv binds FITC, and has the amino acid sequence set forth in SEQ ID NO: 66 (originally described in Söderlind et al, Nature Biotechnology 18(8): 852-856, 2000). As described above, the scFvs were encoded as a single polypeptide chain with either the heavy chain or the light chain of the anti-CD40 antibody. As set forth in the table, in each bispecific antibody the scFv was fused to the C-terminus of the relevant antibody chain, and thus was located either C-terminal to the heavy chain $C_H3$ domain or to the light chain $C_L$ domain, as shown. As previously described, in each bispecific antibody the scFv was joined to the antibody by a linker as indicated in Table 5.

As previously described, bispecific antibodies were expressed in HEK293 cells, and purified by affinity chromatography using protein A followed by preparative size exclusion chromatography (SEC). Retained binding to hCD40 and MTTE or FITC was verified by ELISA.

Example 12

Activation of Dendritic Cells with Bispecific Antibodies

Materials and Methods

Dendritic Cell Microscopy

Pictures of cultured human moDCs were taken at 10× magnification using a Visiscope microscope with a Moticam 1080 camera.

IL-12 ELISA

ELISA experiments were performed as described above in Example 7, except the 1:2 serial dilutions were performed starting from 200 nM.

Flow Cytometry

Flow cytometry was performed as described above in Example 7, using the antibodies HLA-DR-PE-Cy5 (L243), CD86-BV421 (IT2.2) and CD83-APC (HB15e) to measure expression of their target cell surface activation markers.

Results

Figure 6:
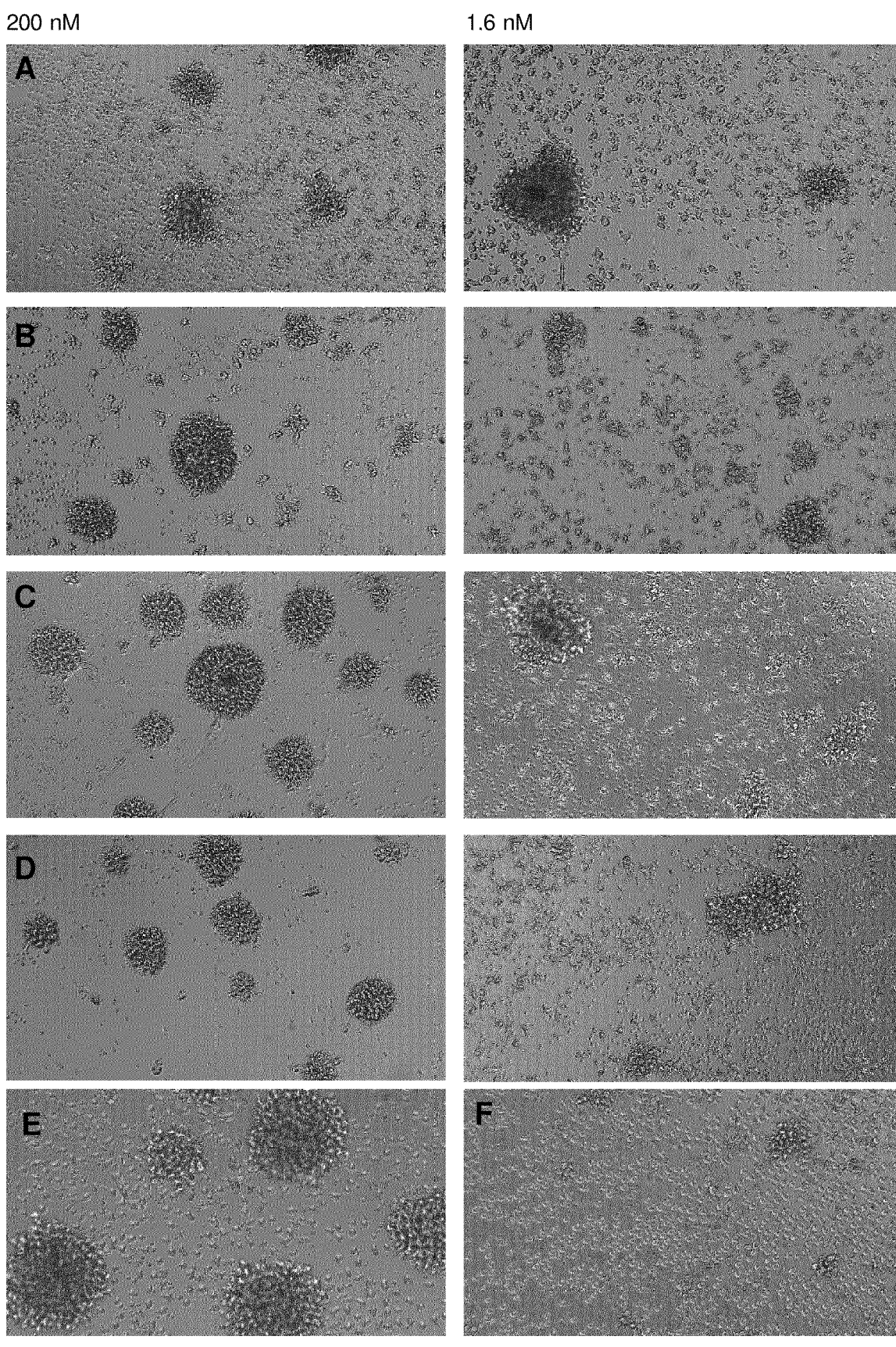
FIG. 6 shows microscopy images of dendritic cells stimulated with a high concentration (200 nM) or low concentration (1.6 nM) of A9 antibody (D) and the A9-based bispecific conjugates Bi-21 (A), Bi-22 (B) and Bi-23 (C). An unstimulated negative control (F) and LPS-stimulated positive control (E) are also shown.

Upon activation, dendritic cells form characteristic clusters (as shown by the appearance of unactivated dendritic cells (FIG. 6F) compared to dendritic cells activated with LPS (FIG. 6E). Dendritic cells were treated with the A9 and B8 antibodies, and with bispecific antibodies derived therefrom, and then visualised to assess activation, as determined by clustering. As expected, the A9 antibody induced significant clustering (indicative of dendritic cell activation) at both a high concentration (200 nM) and low concentration (1.6 nM) (FIG. 6D). The A9 bispecific antibodies Bi-22 (which has the 14GIIICII-b scFv appended at the C-terminus of the A9 $C_L$ domain) and Bi-23 (which has the FITC8 scFv appended at the C-terminus of the A9 $C_H3$ domain) were found to induce a similar level of clustering (FIG. 6B-C) indicating a similar level of agonistic activity. The Bi-21 bispecific antibody (which has the 14GIIICII-b scFv appended at the C-terminus of the A9 $C_H3$ domain) was found to drive a lower level of clustering (FIG. 6A), which could indicate a reduction in agonistic activity relative to the A9 parental antibody, though Bi-21 was also found to be challenging to produce, which could alternatively indicate that this bispecific antibody is generally problematic to use.

Figure 7:
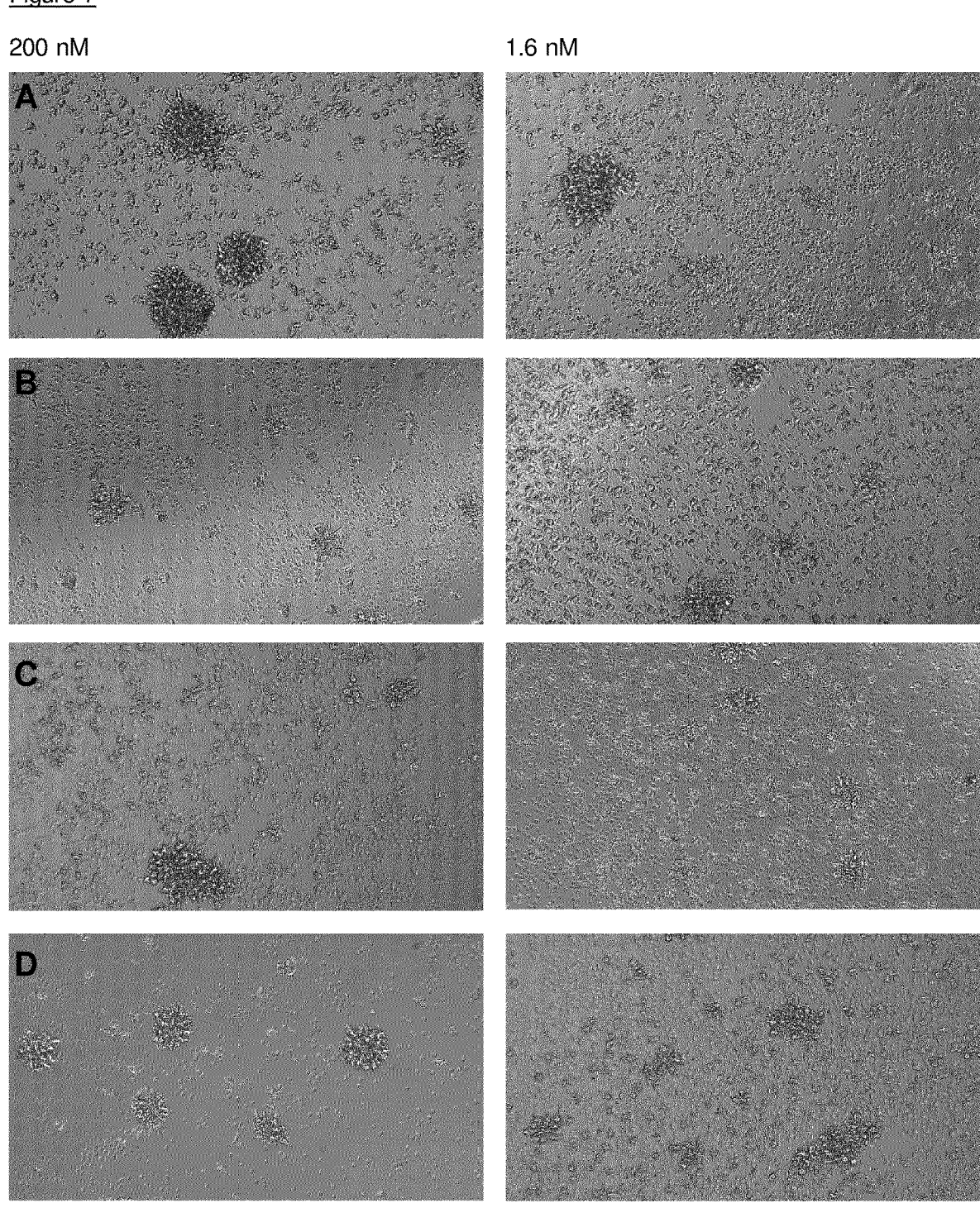
FIG. 7 shows microscopy images of dendritic cells stimulated with a high concentration (200 nM) or low concentration (1.6 nM) of B8 antibody (A) and the B8-based bispecific conjugates Bi-24 (B), Bi-25 (C) and Bi-26 (D).

As expected for a moderate CD40 agonist, the B8 antibody induced some clustering, indicating a degree of dendritic cell activation, particularly at 200 nM (FIG. 7D). However, the bispecific antibodies Bi-24, Bi-25 and Bi-26 all displayed significantly lower levels of agonistic activity than the B8 antibody (FIG. 7A-C). Indeed, the Bi-25 and Bi-26 antibodies induced almost no clustering even at the highest, 200 nM concentration (FIG. 7B-C), while Bi-24 induced a low level of clustering at the highest concentration (FIG. 7A). This suggested that the B8 antibody suffered a substantial loss of agonistic activity upon conversion to bispecific format, not seen in the A9 antibody.

Figure 8:
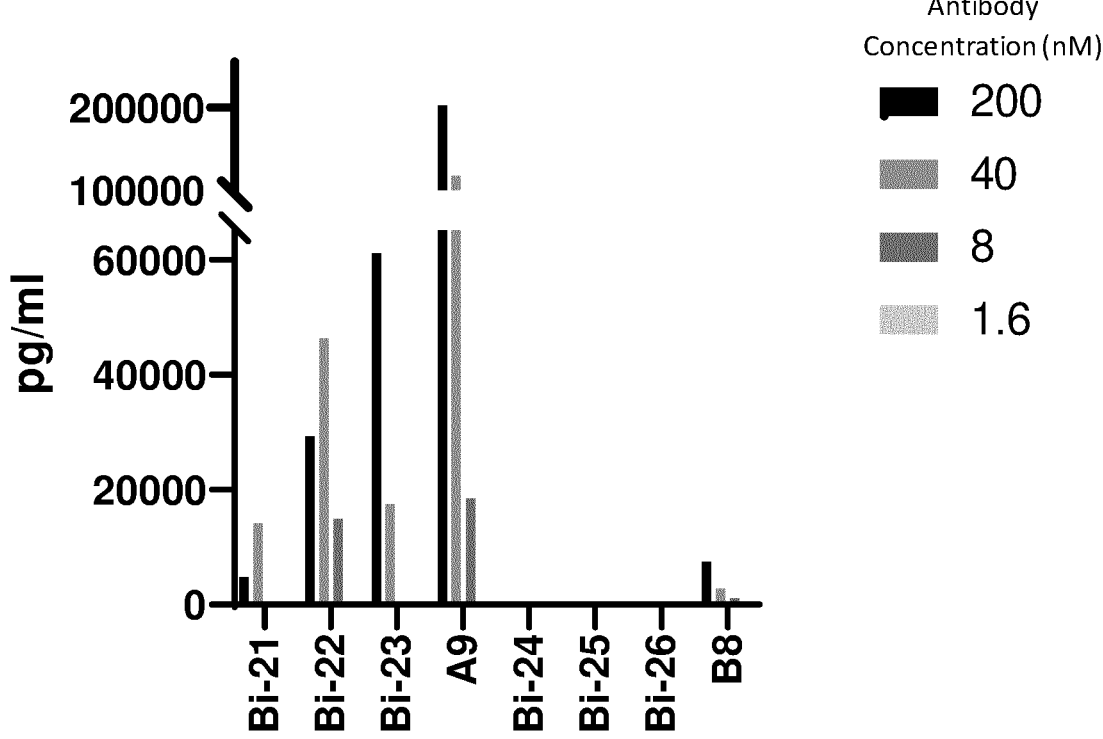
FIG. 8 shows concentration in pg/ml of IL-12 (y axis) in the supernatant of dendritic cells stimulated with the anti-CD40 antibodies A9 and B8, the A9-based bispecific conjugates Bi-21, Bi-22 and Bi-23, and the B8-based bispecific

When analysing dendritic cell activation by IL-12 production, the A9 clone induced substantial cytokine release, while the A9-based bispecific antibodies also induced cytokine release but not to the same levels. Bi-23 induced the highest levels of IL-12 among the bispecific antibodies derived from the A9 clone and Bi-21 the lowest levels (FIG. 8). As expected, B8 induced a lower level of IL-12 production than A9, but the Bi-24, Bi-25 and Bi-26 antibodies unexpectedly did not induce a detectable level of IL-12 production at any antibody concentration.

Figure 9C:
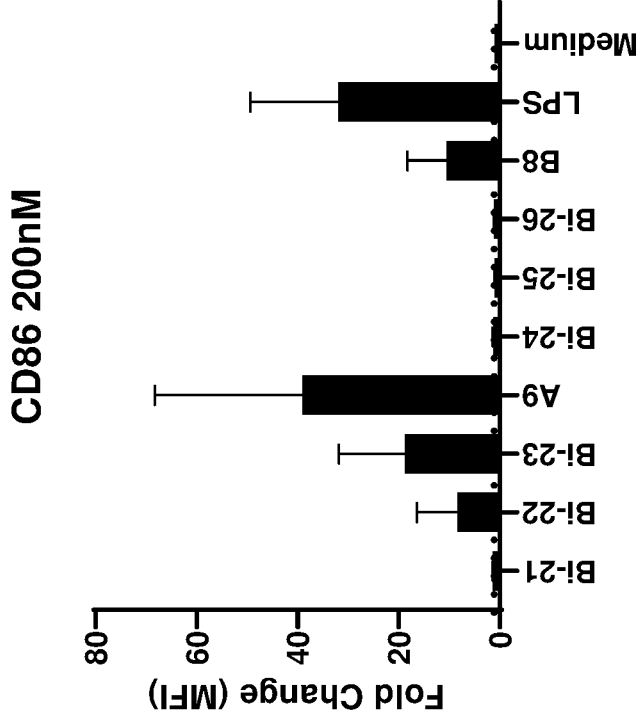

Similarly, both A9 and B8 induced expression of the dendritic cell surface activation markers HLA-DR (an MHC-II component, FIG. 9A), CD83 (FIG. 9B) and CD86 (FIG. 9C). The A9-based bispecific antibody Bi-23 retained most of the agonistic activity of A9, inducing expression of all three surface markers, whereas Bi-22 and Bi-21 (in particular) had decreased agonistic activity. The B8-based bispecific antibodies Bi-24, Bi-25 and Bi-26 induced a minimal level of HLA-DR expression and undetectable or almost undetectable levels of CD83 and CD86 expression as in concordance with IL-12 data.

Conclusions

These results unexpectedly showed that B8, despite displaying a moderate degree of agonistic activity in the context of a standard monoclonal antibody, lost all agonistic activity in the bispecific context. This demonstrates that not all anti-CD40 antibodies are suitable for use in the bispecific antibodies of the invention. The A9 antibody has high agonistic activity, and although some degree of agonism is lost when A9 is converted to bispecific format, sufficient activity is generally retained for efficacy. Accordingly, it is clear that A9 is a particularly suitable antibody for use in the bispecific conjugates of the invention.

The complete loss of agonism in bispecific format is a phenomenon which, to our knowledge, has not been previously observed. The location of the B8 epitope has not been established, but the antibody is known to bind at a site close to or overlapping with the CD40L binding site, since interaction of CD40 with CD40L blocks binding of the antibody (FIG. 1). Meanwhile, the A9 antibody is known to bind in the N-terminal region of CD40, away from the CD40L binding site (see Example 8 and FIG. 1). This has led to the hypothesis that to be active in the bispecific antibody of the invention, an anti-CD40 antibody must bind to CD40 at a highly accessible location, distal to the membrane, to avoid the bulky scFv molecules sterically hindering access to the epitope. Alternative hypotheses also exist: it is possible that depending on the location of the epitope, the bulky scFv molecules can block the trimerisation of CD40 that occurs during activation, or blocks conformational changes that take place in CD40 upon activation. Presently, it is not clear whether the loss of agonism stems from loss of binding to CD40 in the bispecific format, or if the antibody still binds CD40 in the bispecific format but has lost the capability to activate signalling through the receptor.

Example 13

Activation of Dendritic Cells by Additional Bispecific Conjugates

In this Example, additional bispecific constructs derived from the A9 clone and prepared as described in Example 11 were used to evaluate the impact of linker length together with the C127S mutation in the IgG2 constant region. The scFv in the tested bispecific conjugates was a human anti-FITC scFv, positioned either at CH3 or CL as indicated in Table 5. The Example was performed to investigate the potential steric hindrance by the scFv due to linker length and how it affects the agonistic capacity of the bispecific conjugate.

Materials and Methods

CD14+ cell isolation and differentiation were performed as described in Examples 7 and 12, with the exception that 75 ng/ml GM-CSF was used. MoDCs were treated with antibody A9 with IgG2 or IgG2 C127S constant regions or bispecific test conjugates Bi-23, Bi-28, Bi-29, Bi-30, Bi-31, Bi-32, Bi-33 at concentrations between 100-12.5 nM, or with 1 μg/ml of LPS as positive control, for 48 hours before supernatants were collected and IL-12 production was measured using IL-12p40 ELISA as described in Example 7.

Results

IL-12 production from MoDCs in a titration of A9 and the A9 based bispecific antibodies (Bi23, Bi28) and the A9 C127S and A9 C127S bispecific antibodies (Bi29, Bi30, Bi31, Bi32 and Bi33) was measured, and the results are presented in FIG. 10. There was a dose-dependent agonistic potential of the parental antibodies A9 and A9 C127S. As observed for the previously tested bispecific conjugates in Example 12, the bispecific conjugates Bi-23, Bi-28, Bi-29, Bi-30, Bi-31, Bi-32 and Bi-33 retained their respective agonistic potential in a dose-dependent manner, although IL-12 production from these bispecific conjugates was at lower levels than for their parental counterparts. To conclude, linker length and position did not adversely impact the agonistic activity of the tested bispecific conjugates.

Example 14

Design and Generation of Further Bispecific Conjugates

Materials and Methods

Design and Protein Expression in CHO Cells

Further variants of antibodies and bispecific conjugates according to the disclosure were designed. Briefly, the three different antibody isotypes were used: IgG1, IgG2, and a hybrid consisting of said IgG1 sequence with human IgG2 hinge and CH1 sequence grafted into the IgG1 architecture. In bispecific conjugates, a humanized tag-binding scFv sequence was linked C-terminally to the CH3 domain to either of the three isotype variants by either a flexible $(G_4S)_2$ or rigid $(EA_3K)_2$ linker. DNA encoding each variant was transfected into cells using the ExpiCHO™ transfection system (ThermoFisher) in 24 deep well plates. Transfection was performed in duplicates with a total of 2 µg plasmid DNA in 2.5 ml culture volumes. For scaled-up production, ExpiCHO™ cells were transfected as suggested by the manufacturer with a total of 20 µg plasmid DNA per transfection of each construct, in 25 ml culture volumes.

IgG Quantification

IgG concentrations in the supernatant of transfected CHO cells were determined by bio-layer interferometry measurements in an Octet® RED96e system (Fortébio Biologics by Molecular Devices, USA) with Dip and Read™ Protein A biosensors (Fortébio Biologics by Molecular Devices) according to the manufacturer's instructions. The supernatant samples from day 5 of cultivation were diluted 1:1 in 20 mM citric acid pH 4.0, 0.1% BSA (w/v), 0.1% Tween-20, 0.5 M NaCl. A standard curve was prepared from a sample IgG with concentrations from 700 to 1 µg/ml.

IgG Purification

For size exclusion chromatography analysis, the expressed constructs were purified by Protein A facilitated purification on an ÄktaSTART system (GE Healthcare) using mAbSelect SuRe columns (GE Healthcare). A 20 mM sodium phosphate, 0.15 M sodium chloride (pH 7.3) buffer was used as binding and wash buffer, 0.1 M glycine (pH 2.5) as elution buffer and 1 M Tris-HCl (pH 8.5) as neutralization buffer. Endotoxin levels were measured with LAL Cartridges and Endosafe Nextgen-PTS system (Charles River, MA, USA) according to manufacturer's instructions.

SDS-PAGE

A total of 4 µg of each sample purified as above were mixed with 3× loading buffer (0.1 M Tris-HCl, 45% glycerol, 0.03% bromophenol blue, 0.3% SDS) for non-reducing conditions and, for the reducing analysis, mixed with 3× loading buffer containing 0.15 M Tris 2-carboxyethyl-phosphine hydrochloride and incubated at 95° C. for 7 min. The samples were run on a 4-20% Criterion™ TGX Stain-Free™ protein gel (Bio-Rad Laboratories) according to the company's protocol. The bands were visualized by staining the gel in GelCode™ Blue Safe protein stain (Thermo Fisher Scientific) for 1 h at room temperature and gentle shaking.

Size Exclusion Chromatography (SEC)

In total, 25 µg of each expressed conjugate in 100 µl were injected onto a Superdex Increase 200 10/30 GL gel filtration column (GE Healthcare) coupled to an Agilent 1200 series HPLC system (Agilent Technologies). SEC runs were performed at a 0.5 ml/min flow rate with PBS as a running buffer. Eluted protein fragments were detected by an online 280 nm absorption measurement. Data analysis and peak integrations were performed using GraphPad prism 8.0 (GraphPad Software).

Results

Expression and Characterisation of Novel Antibodies and Bispecific Conjugates

The designed constructs (Table 6) were successfully expressed and purified with endotoxin levels below the threshold limit of 0.5 EU/ml. A reducing SDS-PAGE on the purified samples exhibited bands at the expected sizes for the antibody heavy and light chains respectively.

Size Exclusion Chromatography

The SEC analysis showed no signs of significant amounts of heavy molecular weight aggregates in the purified constructs. Non-native populations in the form of lower molecular weight species were observed across the tested constructs to varying degrees.

Summary of Expressed Antibodies and Bispecific Conjugates

The antibodies and bispecific conjugates listed in Table 6 were successfully designed, expressed and purified. In all bispecific conjugates, a variant of the previously tested scFvs was used as second binding protein.

TABLE 6

| Further Antibodies and Bispecific Conjugates | | | | |
|---|---|---|---|---|
| Designation | Anti-CD40 IgG | Subclass | scFv Appending Position | Linker |
| SP2 | A9 | IgG1 | CH3 | $(G_4S)_2$ |
| SP3 | A9 | IgG1 | CH3 | $(EA_3K)_2$ |
| SP4 | A9 | IgG 1/2 hybrid | No scFv | None |
| SP5 | A9 | IgG 1/2 hybrid | CH3 | $(G_4S)_2$ |
| SP6 | A9 | IgG 1/2 hybrid | CH3 | $(EA_3K)_2$ |
| SP7 | A9 | IgG2 | CH3 | $(G_4S)_2$ |
| SP8 | A9 | IgG1 | No scFv | None |
| SP9 (=A9) | A9 | IgG2 | No scFv | None |

Example 15

Activation of Dendritic Cells with Further Antibodies and Bispecific Conjugates

In this Example, the constructs prepared as described in Example 14 were analysed for their agonistic activity.

Materials and Methods

Isolation and differentiation of CD14+ cells were performed as described in Examples 7, 12 and 13 using 75 ng/ml of GM-CSF and 50 ng/ml IL-4. The MoDCs were treated with antibodies or bispecific conjugates with and without the tag peptide UU01 (SEQ ID NO: 79) for 24 h or 48 h, before supernatants were collected and IL-12 production was measured using IL-12p40 ELISA. For the 24 h incubation, cells were additionally stained for the previously described activation markers.

Results

The measured IL-12 production is summarized below in Table 7, giving the relative % activity after 48 h, compared to the A9 (herein named SP9) antibody.

TABLE 7

| Construct | % agonistic activity of A9 at 25 nM |
|---|---|
| SP2 | 9 |
| SP3 | 70 |
| SP4 | 123 |
| SP5 | 82 |
| SP6 | 23 |
| SP7 | 105 |
| SP8 | 11 |
| SP9 | 100 (reference) |

Table 7 summarizes the agonistic activity of the tested constructs SP2-SP8 in comparison with the SP9 (A9) antibody. IgG1-based antibodies, i.e. the parental antibody SP8 and bispecific versions SP2 and SP3, had lower agonistic activities than the reference. The IgG1/2 hybrid versions, i.e. the parental antibody SP4 and bispecific versions SP5 and SP6, had an increased agonistic activity compared to the IgG1-based clones. SP5 (flexible linker) retained agonistic activity better than SP6 (rigid linker). Furthermore, SP7, the bispecific version of the reference A9 IgG2 antibody retained similar agonistic activity.

Also, the parental (Ab5) and bispecific version of the CP-870,893 antibody (Bi2) (see WO 2020/104690) were assessed side-by side with the different A9-based constructs. Bi2 carries the murine 14GIIICII-b clone as scFv. In this version, the agonistic activity of Bi2 was 43% of the parental antibody Ab-5 (CP-870,893). The A9 based bispecific antibody Bi23 carrying the FITC8 scFv retained 92% of the agonistic activity when compared with the SP9 (A9) parental version.

Further, the agonistic activities of the bispecific conjugate SP7 and parental antibody SP9 (A9) were assessed in the presence of the UU01 peptide (SEQ ID NO: 79). Binding of peptide to the bispecific antibody did not affect the agonistic activity in terms of upregulation of activation markers (FIG. 11) or IL-12 secretion (FIG. 12) after 24 h compared to the parental SP9 (A9) antibody.

Example 16

In Vitro Assay of CMV-Specific T Cell Proliferation

Interaction with an activated dendritic cell (DC) is required for efficient activation of a T cell. A T cell receptor (TCR) will recognize a peptide loaded onto an MHC molecule on the DC, and then interact with the co-stimulatory molecules CD83/CD86 through the CD28 receptor. Cytokines like IL-12 will be produced by the activated DC that acts on the T cell. This Example is essentially a repetition of Example 4 on pages 64-65 of WO 2020/104690, performed in order to also compare the ability of a bispecific conjugate based on the novel A9 antibody to stimulate the expansion of a pathogen-specific population of T cells, in comparison with the bispecific conjugate denoted Bi-17 in WO 2020/104690, which is based on the known CD40 binding antibody CP-870,893. It is shown that the bispecific conjugate based on the A9 antibody induces activation through CD40 binding, and that it transports the tag/antigen peptide intracellularly through the interaction between the second binding protein (scFv) and the tag. The fluorescence of the tag provides a detectable signal.

Materials and Methods

An HLA*2A and CMV positive donor was used. CD14+ cell isolation and differentiation was performed essentially as described in Examples 7, 12, 13 and 15. At day 6, the MoDCs were stimulated with the bispecific conjugates Bi-23 (Table 5) and Bi-17 (Table 1 on page 53 of WO 2020/104690), each tested both alone and in complex with the peptide designated UU-44 (SEQ ID NO: 87), which comprises a FITC tag for interaction with the scFv part of the respective bispecific conjugate and an epitope from cytomegalovirus (CMV). In the complexes, the ratio between conjugate and peptide was 1:2 at a concentration of 50 nM of conjugate. The bispecific conjugates and complexes were incubated for 24 h at 37° C. with 5% $CO_2$. Stimulated DCs were split into two replicates in a 6-well plate. The CD14 negative population from the same donor was thawed and mixed at a 1:10 ratio with the stimulated DCs. The co-culture was incubated for another 11 days before specific CMV CD8$^+$ T cells were measured. Cells were stained as described in Example 7 with CMV tetramer-PE (MBL International; cat. no. TB-0010-1), CD3-BV510 (clone: UCHT1) and CD8-FITC (clone: SK1). Samples were pre-incubated with the CMV tetramer for 10 min at room temperature before staining with antibodies.

Results

The results are shown in FIG. 13. Neither the UU-44 peptide alone nor the bispecific conjugates alone induced any specific T cell expansion. However, the complexes of bispecific conjugates with tag peptides comprising the CMV antigen sequence increased the CMV population from 0.6% to a mean of 9-10%. To conclude, the complexes of bispecific antibodies with UU44 peptide led to an expansion of the CMV-specific CD8$^+$ T cells compared to only peptide alone or antibodies alone.

Example 17

Determination of the Minimal Epitope Recognised by 14GIIICII and IBIIICI

Mouse monoclonal antibodies 14GIIICII and IBIIICI were originally raised by immunisation of mice with the 18-mer MTTE peptide (FIGITELKKLESKINKVF, SEQ ID NO: 25). Conversion of these two antibodies to scFv-format and subsequent binding characterisation by SPR of binding to the MTTE is described in Example 10 of WO 2020/104690.

In the below example we demonstrate that C-terminal shortening of the MTTE sequence can be performed without loss of scFv binding. A shortening of the peptide can potentially have several advantages for production purposes, including more efficient protection of the whole tag construct (tag peptide plus tumour/pathogen antigen) from degradation by e.g. proteases and more efficient manufacture.

Materials and Methods

The peptides (Capra Science, Lund, Sweden) used in this example are listed in Table 8:

TABLE 8

| Peptide | Sequence | Length (aa) | MW (Da) | Modification | SEQ ID NO |
|---------|----------|-------------|---------|--------------|-----------|
| UU24 | FIGITELKKLESKINKVF | 18 | 2462.0 | C-term K-biotin | 25 |
| UU70 | FIGITELKKLESKINK | 16 | 1861.3 | none | 29 |
| UU71 | FIGITELKKLESKIN | 15 | 1733.1 | none | 28 |
| UU72 | FIGITELKKLESKI | 14 | 1619.0 | none | 27 |

TABLE 8-continued

| Peptide | Sequence | Length (aa) | MW (Da) | Modification | SEQ ID NO |
|---------|----------|-------------|---------|--------------|-----------|
| UU73 | FIGITELKKLESK | 13 | 1505.8 | none | 26 |
| UU74 | FIGITELKKLES | 12 | 1377.6 | none | 16 |

Affinity measurements for the 14GIIICII and IBIIICI scFv clones were performed by SPR using a Biacore T200 platform (GE Healthcare) and a single cycle kinetics (SCK) approach. The α-FLAG M2 antibody (Sigma-Aldrich) was immobilised onto a CM5-S chip by primary amine coupling using NHS-EDC chemistry, allowing capture of the scFvs via their FLAG tags. A 5-fold dilution series comprising five different concentrations (0.16 nM to 100 nM) of the different peptides (Table 8) was sequentially injected over the flow cells, allowing binding to the captured scFvs. Following a dissociation phase, regeneration of the surface was accomplished under acidic conditions using 10 mM glycine-HCl at pH 2.2. By subtracting the response curve of a reference surface (an α-FLAG antibody immobilised surface), response unit sensorgrams for all peptides were obtained. Data was analysed using the software BIAeval v.3.1 (GE Healthcare).

Results

Similar capture levels (RU) could be obtained for all cycles. Following injection of analyte, chip surfaces could successfully be regenerated leaving an active surface ready for the next antibody-capture cycle.

Surprisingly, the binding of the IBIIICI scFv is seemingly unaffected by shortening of the peptide from 18 to 12 amino acids. Visual inspection of the sensorgrams (not shown) shows a very similar binding pattern to all of the tested peptides. This is illustrated in Table 9, where the kinetic parameters of the different peptides are given, and in FIG. 14. The 14GIIICII scFv also shows clear binding to all of the tested peptides. However, in contrast to IBIIICI, the affinity ($K_D$) is somewhat increased with the shortening of the peptide. This is mainly a result of increases in the off rate (the dissociation rate constant ($k_d$)), as shown in Table 9.

The results presented here suggest that the MTTE tag peptide can be shortened to 12 or 13 amino acids without considerable loss of binding to IBIIICI or 14GIIICII, respectively. The kinetic parameters reported here differ somewhat to those reported previously for the same scFv clones. This discrepancy could be explained by differences in experimental set-up, including different peptide designs. Also, the obtained $k_d$ values are very close to the limit of detection of the instrument ($<10^{-5}$). This is particularly true for the different peptides binding to IBIIICI. In order to get a more accurate estimation of the off-rates a considerably longer dissociation time is recommended. Hence, the reported kinetic parameters should be viewed with care and should primarily be used to compare the binding of the different peptides to the two scFv rather than as providing accurate absolute kinetic parameters.

TABLE 9

| | IBIIICI scFv | | | 14GIIICII scFv | | |
|---|---|---|---|---|---|---|
| | $k_a$ (1/Ms) | $k_d$ (1/s) | $K_D$ (M) | $k_a$ (1/Ms) | $k_d$ (1/s) | $K_D$ (M) |
| UU24 | 1.9E+05 | 2.3E−05 | 1.2E−10 | 6.6E+05 | 2.0E−04 | 3.0E−10 |
| UU70 | 2.3E+05 | 3.7E−05 | 1.6E−10 | 6.5E+05 | 1.9E−04 | 2.9E−10 |
| UU71 | 2.3E+05 | * | n/a | 5.4E+05 | 3.2E−04 | 6.0E−10 |
| UU72 | 2.5E+05 | * | n/a | 5.7E+05 | 3.4E−04 | 6.0E−10 |
| UU73 | 2.0E+05 | 6.7E−05 | 3.4E−10 | 5.1E+05 | 4.4E−04 | 8.7E−10 |
| UU74 | 2.8E+05 | 3.3E−05 | 1.2E−10 | 5.7E+05 | 9.5E−04 | 1.7E−09 |

Kinetic parameters for 14GIIICII and IBIIICI scFv clones towards the MTTE sequence and trimmed versions thereof. The dissociation rate constant ($k_d$) values reported as "*" indicate that these are too low for, or very close to the detection limit of, instrument specification ($<10^{-5}$).

SEQUENCE LISTING

Sequences in upper case are protein sequences; those in lower case are nucleic acid sequences.

SEQ ID NO: 1
QSISSY

SEQ ID NO: 2
AAS

SEQ ID NO: 3
QQGYPYPFT

SEQ ID NO: 4
GFTFSSYA

SEQ ID NO: 5
ISGYSGST

Sequences in upper case are protein sequences; those in lower case are nucleic acid
sequences.

SEQ ID NO: 6
ARYYSYYGYYYFDY

SEQ ID NO: 7
DIQMTQSPSSLSASVGDRVTITCRASQSISSYLNWYQQKPGKAPKLLIYAASSLQSGVPSRF
SGSGSGTDFTLTISSLQPEDFATYYCQQGYPYPFTFGQGTKLEIK

SEQ ID NO: 8
EVQLLESGGGLVQPGGSLRLSCAASGFTFSSYAMSWVRQAPGKGLEWVSGISGYSGSTY
YADSVKGRFTISRDNSKNTLYLQMNSLRAEDTAVYYCARYYSYYGYYYFDYWGQGTLVTV
SS

SEQ ID NO: 9
DIQMTQSPSSLSASVGDRVTITCRASQSISSYLNWYQQKPGKAPKLLIYAASSLQSGVPSRF
SGSGSGTDFTLTISSLQPEDFATYYCQQGYPYPFTFGQGTKLEIKRTVAAPSVFIFPPSDEQ
LKSGTASVVCLLNNFYPREAKVQWKVDNALQSGNSQESVTEQDSKDSTYSLSSTLTLSKA
DYEKHKVYACEVTHQGLSSPVTKSFNRGEC

SEQ ID NO: 10
EVQLLESGGGLVQPGGSLRLSCAASGFTFSSYAMSWVRQAPGKGLEWVSGISGYSGSTY
YADSVKGRFTISRDNSKNTLYLQMNSLRAEDTAVYYCARYYSYYGYYYFDYWGQGTLVTV
SSASTKGPSVFPLAPCSRSTSESTAALGCLVKDYFPEPVTVSWNSGALTSGVHTFPAVLQS
SGLYSLSSVVTVPSSNFGTQTYTCNVDHKPSNTKVDKTVERKCCVECPPCPAPPVAGPSV
FLFPPKPKDTLMISRTPEVTCVVVDVSHEDPEVQFNWYVDGVEVHNAKTKPREEQFNSTFR
VVSVLTVVHQDWLNGKEYKCKVSNKGLPAPIEKTISKTKGQPREPQVYTLPPSREEMTKN
QVSLTCLVKGFYPSDIAVEWESNGQPENNYKTTPPMLDSDGSFFLYSKLTVDKSRWQQGN
VFSCSVMHEALHNHYTQKSLSLSPGK

SEQ ID NO: 11
GILFLQWVRDIIDDFTNESSQK

SEQ ID NO: 12
DSDKDRFLQTMVKLFNRIKNN

SEQ ID NO: 13
IKNDLYEKTLNDYKAIANKLSQV

SEQ ID NO: 14
QDPALLLMHELIHVLHGLYGM

SEQ ID NO: 15
DGILFLQWVRDIIDDFTNESSQKR

SEQ ID NO: 16
FIGITELKKLES

SEQ ID NO: 17
MVRLPLQCVLWGCLLTAVHPEPPTACREKQYLINSQCCSLCQPGQKLVSDCTEFTETECLP
CGESEFLDTWNRETHCHQHKYCDPNLGLRVQQKGTSETDTICTCEEGWHCTSEACESCV
LHRSCSPGFGVKQIATGVSDTICEPCPVGFFSNVSSAFEKCHPWTSCETKDLVVQQAGTNK
TDVVCGPQDRLRALVVIPIIFGILFAILLVLVFIKKVAKKPTNKAPHPKQEPQEINFPDDLPGSN
TAAPVQETLHGCQPVTQEDGKESRISVQERQ

SEQ ID NO: 18
ASTKGPSVFPLAPCSRSTSESTAALGCLVKDYFPEPVTVSWNSGALTSGVHTFPAVLQSSG
LYSLSSVVTVPSSNFGTQTYTCNVDHKPSNTKVDKTVERKCCVECPPCPAPPVAGPSVFLF
PPKPKDTLMISRTPEVTCVVVDVSHEDPEVQFNWYVDGVEVHNAKTKPREEQFNSTFRVV
SVLTVVHQDWLNGKEYKCKVSNKGLPAPIEKTISKTKGQPREPQVYTLPPSREEMTKNQVS
LTCLVKGFYPSDIAVEWESNGQPENNYKTTPPMLDSDGSFFLYSKLTVDKSRWQQGNVFS
CSVMHEALHNHYTQKSLSLSPGK

SEQ ID NO: 19
RTVAAPSVFIFPPSDEQLKSGTASVVCLLNNFYPREAKVQWKVDNALQSGNSQESVTEQD
SKDSTYSLSSTLTLSKADYEKHKVYACEVTHQGLSSPVTKSFNRGEC

SEQ ID NO: 20
ASTKGPSVFPLAPSSRSTSESTAALGCLVKDYFPEPVTVSWNSGALTSGVHTFPAVLQSSG
LYSLSSVVTVPSSNFGTQTYTCNVDHKPSNTKVDKTVERKCCVECPPCPAPPVAGPSVFLF
PPKPKDTLMISRTPEVTCVVVDVSHEDPEVQFNWYVDGVEVHNAKTKPREEQFNSTFRVV
SVLTVVHQDWLNGKEYKCKVSNKGLPAPIEKTISKTKGQPREPQVYTLPPSREEMTKNQVS
LTCLVKGFYPSDIAVEWESNGQPENNYKTTPPMLDSDGSFFLYSKLTVDKSRWQQGNVFS
CSVMHEALHNHYTQKSLSLSPGK

SEQ ID NO: 21
GGGGS

-continued

Sequences in upper case are protein sequences; those in lower case are nucleic acid
sequences.

SEQ ID NO: 22
GGGGSGGGGS

SEQ ID NO: 23
MPITINNFRYSDPVNNDTIIMMEPPYCKGLDIYYKAFKITDRIWIVPERYEFGTKPEDFNPPSS
LIEGASEYYDPNYLRTDSDKDRFLQTMVKLFNRIKNNVAGEALLDKIINAIPYLGNSYSLLDKF
DTNSNSVSFNLLEQDPSGATTKSAMLTNLIIFGPGPVLNKNEVRGIVLRVDNKNYFPCRDGF
GSIMQMAFCPEYVPTFDNVIENITSLTIGKSKYFQDPALLLMHELIHVLHGLYGMQVSSHEIIP
SKQEIYMQHTYPISAEELFTFGGQDANLISIDIKNDLYEKTLNDYKAIANKLSQVTSCNDPNIDI
DSYKQIYQQKYQFDKDSNGQYIVNEDKFQILYNSIMYGFTEIELGKKFNIKTRLSYFSMNHDP
VKIPNLLDDTIYNDTEGFNIESKDLKSEYKGQNMRVNTNAFRNVDGSGLVSKLIGLCKKIIPPT
NIRENLYNRTASLTDLGGELCIKIKNEDLTFIAEKNSFSEEPFQDEIVSYNTKNKPLNFNYSLD
KIIVDYNLQSKITLPNDRTTPVTKGIPYAPEYKSNAASTIEIHNIDDNTIYQYLYAQKSPTTLQRI
TMTNSVDDALINSTKIYSYFPSVISKVNQGAQGILFLQWVRDIIDDFTNESSQKTTIDKISDVS
TIVPYIGPALNIVKQGYEGNFIGALETTGVVLLLEYIPEITLPVIAALSIAESSTQKEKIIKTIDNFL
EKRYEKWIEVYKLVKAKWLGTVNTQFQKRSYQMYRSLEYQVDAIKKIIDYEYKIYSGPDKEQ
IADEINNLKNKLEEKANKAMININIFMRESSRSFLVNQMINEAKKQLLEFDTQSKNILMQYIKA
NSKFIGITELKKLESKINKVFSTPIPFSYSKNLDCWVDNEEDIDVILKKSTILNLDINNDIISDISG
FNSSVITYPDAQLVPGINGKAIHLVNNESSEVIVHKAMDIEYNDMFNNFTVSFWLRVPKVSA
SHLEQYGTNEYSIISSMKKHSLSIGSGWSVSLKGNNLIWTLKDSAGEVRQITFRDLPDKFNA
YLANKWVFITITNDRLSSANLYINGVLMGSAEITGLGAIREDNNITLKLDRCNNNNQYVSIDKF
RIFCKALNPKEIEKLYTSYLSITFLRDFWGNPLRYDTEYYLIPVASSSKDVQLKNITDYMYLTN
APSYTNGKLNIYYRRLYNGLKFIIKRYTPNNEIDSFVKSGDFIKLYVSYNNNEHIVGYPKDGN
AFNNLDRILRVGYNAPGIPLYKKMEAVKLRDLKTYSVQLKLYDDKNASLGLVGTHNGQIGND
PNRDILIASNWYFNHLKDKILGCDWYFVPTDEGWTND

SEQ ID NO: 24
MLVRGYWSRKLFASILIGALLGIGAPPSAHAGADDWDSSKSFVMENFSSYHGTKPGYVDS
IQKGIQKPKSGTQGNYDDDWKGFYSTDNKYDAAGYSVDNENPLSGKAGGVVKVTYPGLTK
VLALKVDNAETIKKELGLSLTEPLMEQVGTEEFIKRFGDGASRVVLSLPFAEGSSSVEYINN
WEQAKALSVELEINFETRGKRGQDAMYEYMAQACAGNRVRRSVGSSLSCINLDWDVIRDK
TKTKIESLKEHGPIKNKMSESPNKTVSEEKAKQYLEEFHQTALEHPELSELKTVTGTNPVFA
GANYAAWAVNVAQVIDSETADNLEKTTAALSILPGIGSVMGIADGAVHHNTEEIVAQSIALSS
LMVAQAIPLVGELVDIGFAAYNFVESIINLFQVVHNSYNRPAYSPGHKTQPFLHDGYAVSWN
TVEDSIIRTGFQGESGHDIKITAENTPLPIAGVLLPTIPGKLDVNKSKTHISVNGRKIRMRCRAI
DGDVTFCRPKSPVYVGNGVHANLHVAFHRSSSEKIHSNEISSDSIGVLGYQKTVDHTKVNS
KLSLFFEIKS

SEQ ID NO: 25
FIGITELKKLESKINKVF

SEQ ID NO: 26
FIGITELKKLESK

SEQ ID NO: 27
FIGITELKKLESKI

SEQ ID NO: 28
FIGITELKKLESKIN

SEQ ID NO: 29
FIGITELKKLESKINK

SEQ ID NO: 30
YIGITELKKLES

SEQ ID NO: 31
FVGITELKKLES

SEQ ID NO: 32
FIVITELKKLES

SEQ ID NO: 33
FIGVTELKKLES

SEQ ID NO: 34
FIGISELKKLES

SEQ ID NO: 35
FIGITDLKKLES

SEQ ID NO: 36
FIGITEVKKLES

SEQ ID NO: 37
FIGITELVKLES

-continued

Sequences in upper case are protein sequences; those in lower case are nucleic acid
sequences.

SEQ ID NO: 38
FIGITELKVLES

SEQ ID NO: 39
FIGITELKKVES

SEQ ID NO: 40
FIGITELKKLDS

SEQ ID NO: 41
FIGITELKKLET

SEQ ID NO: 42
NDYKAIANKLS

SEQ ID NO: 43
LMHELIHVLHGLY

SEQ ID NO: 44
LMHELIHVLHGLYGM

SEQ ID NO: 45
LIHVLHGLY

SEQ ID NO: 46
PALLLMHELIHVLH

SEQ ID NO: 47
QVQLQQPGAELVMPGASVNLSCKASGYTFTDYWMHWVKQRPGQGLEWIGEIDPSDNFSN
LNQNFRGKATLTVDKSSRTAFLQLSSLTSEDSAVYYCAVEDYWGQGTTLTVSSGGGGSGG
GGSGGGGSGGGGSDIVMTQATPSVLVTPGEAVSISCRASRSLLHSNGITYLYWFLQRPGQ
SPQVLIYRMSNLVSGVPDRFSGSGSGTAFTLRISRVEAEDVGVYYCMQHLEFPYTFGGGTK
LEIK

SEQ ID NO: 48
EVRLLQSGAALVRPGASVKLSCTASGFNIKDFNIHWVKQRPEQGLEWIGRIDPENGDAEYV
PKFQVRATMTTDTSSNTVYLHLSSLTSGDTAVYYCTTGSYDLDVEYWGQGTTLTVSSGGG
GSGGGGSGGGGSGGGGSELQMTQSPSSLSASLGDTVTITCHASQNINVWLSWYQQRPG
NIPKLLIYKASTLHTGVPSRFRGSGSGTGFTLTISSLQPEDIATYYCQQGQSYPLTFGAGTKL
ELK

SEQ ID NO: 49
GYTFTDYW

SEQ ID NO: 50
IDPSDNFS

SEQ ID NO: 51
AVEDY

SEQ ID NO: 52
RSLLHSNGITY

SEQ ID NO: 53
RMS

SEQ ID NO: 54
MQHLEFPYT

SEQ ID NO: 55
GFNIKDFN

SEQ ID NO: 56
IDPENGDA

SEQ ID NO: 57
TTGSYDLDVEY

SEQ ID NO: 58
QNINVW

SEQ ID NO: 59
KAS

-continued

Sequences in upper case are protein sequences; those in lower case are nucleic acid
sequences.

```
SEQ ID NO: 60
QQGQSYPLT

SEQ ID NO: 61
DIQMTQSPSSLSASVGDRVTITCRASQSISSYLNWYQQKPGKAPKLLIYAASSLQSGVPSRF
SGSGSGTDFTLTISSLQPEDFATYYCQQGYGYPPFTFGQGTKLEIK

SEQ ID NO: 62
EVQLLESGGGLVQPGGSLRLSCAASGFTFSSYAMSWVRQAPGKGLEWVSAISGSGGSTY
YADSVKGRFTISRDNSKNTLYLQMNSLRAEDTAVYYCARYVWGIDYWGQGTLVTVSS

SEQ ID NO: 63
EPPTACREKQ

SEQ ID NO: 64
EPPTACREKQYL

SEQ ID NO: 65
ECLPCGESEF

SEQ ID NO: 66
EVQLLESGGGLVQPGGSLRLSCAASGFTFSNYWMSWVRQAPGKGLEWVSGISGNGGYTY
FADSVKDRFTISRDNSKNTLYLQMNSLRAEDTAVYYCAGGDGSGWSFWGQGTLVTVSSG
GGGSGGGGSGGGGSGGGGSQSVLTQPPSASGTPGQRVTISCTGSSSNIGAGYDVHWYQ
QLPGTAPKLLIYGNNNRPSGVPDRFSGSKSGTSASLAISGLRSEDEADYYCAAWDDSLSGR
VFGGGTKLTVL

SEQ ID NO: 67
FIGITELKKLESKINKVFAVGALKVPRNQDWLGVPRQL

SEQ ID NO: 68
EVQLLESGGGLVQPGGSLRLSCAASGFTFSSYAMSWVRQAPGKGLEWVSSISSSSGSTYY
ADSVKGRFTISRDNSKNTLYLQMNSLRAEDTAVYYCARHGRWGYYFDYWGQGTLVTVSS
GGGGSGGGGSGGGGSDIQMTQSPSSLSASVGDRVTITCRASQSISSYLNWYQQKPGKAP
KLLIYAASSLQSGVPSRFSGSGSGTDFTLTISSLQPEDFATYYCQQISGPFTFGQGTKLEIK

SEQ ID NO: 69
EVQLLESGGGLVQPGGSLRLSCAASGFTFSSYAMSWVRQAPGKGLEWVSAISGSGGSTY
YADSVKGRFTISRDNSKNTLYLQMNSLRAEDTAVYYCARTPPPSSSRSYLDYWGQGTLVT
VSSGGGGSGGGGSGGGGSDIQMTQSPSSLSASVGDRVTITCRASQSISSYLNWYQQKPG
KAPKLLIYAASSLQSGVPSRFSGSGSGTDFTLTISSLQPEDFATYYCQQYYPLFTFGQGTKL
EIK

SEQ ID NO: 70
EVQLLESGGGLVQPGGSLRLSCAASGFTFSGYYMYWVRQAPGKGLEWVSYIGYSGGGTG
YADSVKGRFTISRDNSKNTLYLQMNSLRAEDTAVYYCARVPFGAFDYWGQGTLVTVSSGG
GGSGGGGSGGGGSDIQMTQSPSSLSASVGDRVTITCRASQSISSYLNWYQQKPGKAPKLL
IYAASSLQSGVPSRFSGSGSGTDFTLTISSLQPEDFATYYCQQYYGFPYTFGQGTKLEIK

SEQ ID NO: 71
EVQLLESGGGLVQPGGSLRLSCAASGFTFSSYAMSWVRQAPGKGLEWVSAISGSGGSTY
YADSVKGRFTISRDNSKNTLYLQMNSLRAEDTAVYYCARYPRPYSIFISIDYWGQGTLVTV
SSGGGGSGGGGSGGGGSDIQMTQSPSSLSASVGDRVTITCRASQSISSYLNWYQQKPGK
APKLLIYAASSLQSGVPSRFSGSGSGTDFTLTISSLQPEDFATYYCQQTYGTPFTFGQGTKL
EIK

SEQ ID NO: 72
EVQLLESGGGLVQPGGSLRLSCAASGFTFSSYAMSWVRQAPGKGLEWVSAISGSGGSTY
YADSVKGRFTISRDNSKNTLYLQMNSLRAEDTAVYYCARYSVPYSPYYSFDYWGQGTLVT
VSSGGGGSGGGGSGGGGSDIQMTQSPSSLSASVGDRVTITCRASQSISSYLNWYQQKPG
KAPKLLIYAASSLQSGVPSRFSGSGSGTDFTLTISSLQPEDFATYYCQQTYSPPTFGQGTKL
EIK

SEQ ID NO: 73
EVQLLESGGGLVQPGGSLRLSCAASGFTFSSYAMSWVRQAPGKGLEWVSAISGSGGSTY
YADSVKGRFTISRDNSKNTLYLQMNSLRAEDTAVYYCARYTYGGFPFSSFDYWGQGTLVT
VSSGGGGSGGGGSGGGGSDIQMTQSPSSLSASVGDRVTITCRASQSISSYLNWYQQKPG
KAPKLLIYAASSLQSGVPSRFSGSGSGTDFTLTISSLQPEDFATYYCQQYRFLSTFGQGTKL
EIK

SEQ ID NO: 74
EVQLLESGGGLVQPGGSLRLSCAASGFTFSSYAMSWVRQAPGKGLEWVSGISGYSGSTY
YADSVKGRFTISRDNSKNTLYLQMNSLRAEDTAVYYCARYYSYYGYYYFDYWGQGTLVTV
SSASTKGPSVFPLAPSSRSTSESTAALGCLVKDYFPEPVTVSWNSGALTSGVHTFPAVLQS
SGLYSLSSVVTVPSSNFGTQTYTCNVDHKPSNTKVDKTVERKCCVECPPCPAPPVAGPSV
```

Sequences in upper case are protein sequences; those in lower case are nucleic acid
sequences.

```
FLFPPKPKDTLMISRTPEVTCVVVDVSHEDPEVQFNWYVDGVEVHNAKTKPREEQFNSTFR
VVSVLTVVHQDWLNGKEYKCKVSNKGLPAPIEKTISKTKGQPREPQVYTLPPSREEMTKN
QVSLTCLVKGFYPSDIAVEWESNGQPENNYKTTPPMLDSDGSFFLYSKLTVDKSRWQQGN
VFSCSVMHEALHNHYTQKSLSLSPGK
```

SEQ ID NO: 75
```
gacatccagatgacccagtctccatcctccctgagcgcatctgtaggagaccgcgtcaccatcacctgcagggcaagtcagag
cattagcagctatttaaattggtatcagcagaaaccagggaaagcccctaagctcctgatctatgctgcatccagtttgcaaagtg
gggtcccatcacgtttcagtggcagtggaagcgggacagatttcactctcaccatcagcagtctgcaacctgaagattttgcaactt
attactgtcaacagggttacccgtacccgttcacttttggccaggggaccaagctggagatcaaa
```

SEQ ID NO: 76
```
gaggtgcaattgttggagagcggggaggcttggtacagcctggggggtccctgcgcctctcctgtgcagccagcggattcacc
tttagcagctatgccatgagctgggtccgccaggctccagggaaggggctggagtgggtctcaggtatttctggttacagtggttct
acatactatgcagactccgtgaaggrccggttcaccatctcccgtgacaattccaagaacacgctgtatctgcaaatgaacagc
ctgcgtgccgaggacacggctgtatattattgtgcgcgctactactcttactacggttactactactttgactattggggccaaggaac
cctggtcaccgtctcctca
```

SEQ ID NO: 77
```
ASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVERKCCVECPPCPPCPAPELLGGPS
VFLFPPKPKDTLMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYTLPPSRDELTKN
QVSLTCLVKGFYPSDIAVEWESNGQPENNYKTTPPVLDSDGSFFLYSKLTVDKSRWQQGN
VFSCSVMHEALHNHYTQKSLSLSPGK
```

SEQ ID NO: 78
```
ASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELLGGPS
VFLFPPKPKDTLMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYTLPPSRDELTKN
QVSLTCLVKGFYPSDIAVEWESNGQPENNYKTTPPVLDSDGSFFLYSKLTVDKSRWQQGN
VFSCSVMHEALHNHYTQKSLSLSPGK
```

SEQ ID NO: 79
```
FIGITELKKLESKINKVFAGILARNLVPMVATVQGQNLKY
```

SEQ ID NO: 80
```
EAAAK
```

SEQ ID NO: 81
```
EAAAKEAAAK
```

SEQ ID NO: 82
```
GGGSGGGSGGGS
```

SEQ ID NO: 83
```
GGGSGGGSGGGSGGGS
```

SEQ ID NO: 84
```
GGGSGGGSGGGSGGGSGGGS
```

SEQ ID NO: 85
```
EVQLLESGGGLVQPGGSLRLSCAASGFTFSSYAMSWVRQAPGKGLEWVSGISGYSGSTY
YADSVKGRFTISRDNSKNTLYLQMNSLRAEDTAVYYCARYYSYYGYYYFDYWGQGTLVTV
SSASTKGPSVFPLAPSSKSTSGGTAALGCLVKDYFPEPVTVSWNSGALTSGVHTFPAVLQS
SGLYSLSSVVTVPSSSLGTQTYICNVNHKPSNTKVDKKVERKCCVECPPCPPCPAPELLGG
PSVFLFPPKPKDTLMISRTPEVTCVVVDVSHEDPEVKFNWYVDGVEVHNAKTKPREEQYNS
TYRVVSVLTVLHQDWLNGKEYKCKVSNKALPAPIEKTISKAKGQPREPQVYTLPPSRDELTK
NQVSLTCLVKGFYPSDIAVEWESNGQPENNYKTTPPVLDSDGSFFLYSKLTVDKSRWQQG
NVFSCSVMHEALHNHYTQKSLSLSPGK
```

SEQ ID NO: 86
```
EVQLLESGGGLVQPGGSLRLSCAASGFTFSSYAMSWVRQAPGKGLEWVSGISGYSGSTY
YADSVKGRFTISRDNSKNTLYLQMNSLRAEDTAVYYCARYYSYYGYYYFDYWGQGTLVTV
SSASTKGPSVFPLAPSSKSTSGGTAALGCLVKDYFPEPVTVSWNSGALTSGVHTFPAVLQS
SGLYSLSSVVTVPSSSLGTQTYICNVNHKPSNTKVDKKVEPKSCDKTHTCPPCPAPELLGG
PSVFLFPPKPKDTLMISRTPEVTCVVVDVSHEDPEVKFNWYVDGVEVHNAKTKPREEQYNS
TYRVVSVLTVLHQDWLNGKEYKCKVSNKALPAPIEKTISKAKGQPREPQVYTLPPSRDELTK
NQVSLTCLVKGFYPSDIAVEWESNGQPENNYKTTPPVLDSDGSFFLYSKLTVDKSRWQQG
NVFSCSVMHEALHNHYTQKSLSLSPGK
```

SEQ ID NO: 87
```
AGILARNLVPMVATVQ
```

The invention claimed is:

1. A binding protein that specifically binds CD40, wherein said binding protein is an agonist of CD40 and comprises a binding domain of an antibody, the binding domain comprising a heavy chain variable domain and a light chain variable domain, each comprising three complementarity determining domains (CDRs), wherein:

VLCDR1 has the sequence set forth in SEQ ID NO: 1;

VLCDR2 has the amino acid sequence AAS;

VLCDR3 has the sequence set forth in SEQ ID NO: 3;

VHCDR1 has the sequence set forth in SEQ ID NO: 4;

VHCDR2 has the sequence set forth in SEQ ID NO: 5; and

VHCDR3 has the sequence set forth in SEQ ID NO: 6.

2. The binding protein of claim 1, wherein the binding protein binds, and is an agonist of, human CD40.

3. The binding protein of claim 1, wherein the binding protein is a monoclonal antibody, an antibody fragment or an scFv.

4. The binding protein of claim 3, wherein the antibody, antibody fragment or scFv is human.

5. The binding protein of claim 3, wherein the antibody fragment is a Fab or F(ab')₂ antibody fragment.

6. The binding protein of claim 3, wherein the light chain variable domain comprises the amino acid sequence set forth in SEQ ID NO: 7, or an amino acid sequence having at least 80% sequence identity thereto; and the heavy chain variable domain comprises the amino acid sequence set forth in SEQ ID NO: 8, or an amino acid sequence having at least 80% sequence identity thereto.

7. The binding protein of claim 3, wherein said specific binding molecule is a monoclonal antibody of the IgG2 isotype.

8. The binding protein of claim 7, wherein the antibody comprises a light chain comprising the amino acid sequence set forth in SEQ ID NO: 9, or an amino acid sequence having at least 80% sequence identity thereto; and a heavy chain comprising the amino acid sequence set forth in SEQ ID NO: 10, or an amino acid sequence having at least 80% sequence identity thereto.

9. A bispecific conjugate comprising:

(i) at least one first binding protein, wherein said first binding protein is the binding protein of claim 1; and (ii) at least one second binding protein, which comprises a binding domain of an antibody and binds a peptide moiety;

wherein the first and second binding proteins are covalently linked.

10. The bispecific conjugate of claim 9, wherein the first binding protein is a monoclonal antibody and the second binding protein is an scFv.

11. The bispecific conjugate of claim 10, wherein the scFv is covalently linked to:

(i) a $C_H3$ domain of the antibody; or (ii) a $C_L$ domain of the antibody.

12. The bispecific conjugate of claim 11, wherein the conjugate comprises one monoclonal antibody and two scFvs, and:

(i) one scFv is conjugated to the $C_H3$ domain of each heavy chain of said antibody; or (ii) one scFv is conjugated to the $C_L$ domain of each light chain of said antibody.

13. The bispecific conjugate of claim 10, wherein the monoclonal antibody is of the IgG2 isotype.

14. The bispecific conjugate of claim 9, wherein the peptide moiety has a non-human amino acid sequence.

15. The bispecific conjugate of claim 14, wherein the peptide moiety has an amino acid sequence derived from a micro-organism.

16. The bispecific conjugate of claim 14, wherein the peptide moiety has an amino acid sequence derived from a bacterial toxin.

17. The bispecific conjugate of claim 16, wherein the peptide moiety has an amino acid sequence derived from tetanus toxin.

18. The bispecific conjugate of claim 16, wherein:

(i) the peptide moiety consists of the amino acid sequence set forth in SEQ ID NO: 16 and the second binding moiety is a scFv comprising the amino acid sequence set forth in SEQ ID NO: 47 or 48, or an amino acid sequence having at least 80% sequence identity thereto, with the proviso that the CDRs are as set out in SEQ ID NOs: 49-54 or 55-60 respectively; or (ii) the peptide moiety consists of the amino acid sequence set forth in SEQ ID NO: 13, and the second binding moiety is an scFv comprising the amino acid sequence set forth in SEQ ID NO: 68, or an amino acid sequence having at least 80% sequence identity thereto; or (iii) the peptide moiety consists of the amino acid sequence set forth in SEQ ID NO: 14, and the second binding moiety is an scFv comprising the amino acid sequence set forth in any one of SEQ ID NOs: 69-73, or an amino acid sequence having at least 80% sequence identity thereto.

19. A complex comprising the bispecific conjugate of claim 9 and a tag construct, the tag construct comprising the peptide moiety of (ii) covalently attached to an antigen;

wherein the peptide moiety of said tag construct is non-covalently bound to the second binding protein of the bispecific conjugate.

20. The complex of claim 19, wherein said antigen is a cancer antigen.

21. The complex of claim 20, wherein said cancer antigen is a neoantigen, a tumour-associated antigen, or an antigen derived from an oncovirus.

22. The complex of claim 19, wherein said antigen is derived from a pathogen.

23. A kit comprising:

(i) a bispecific conjugate as defined in claim 9; and (ii) a tag construct comprising a peptide moiety recognised by the second binding protein of the conjugate of (i), covalently linked to an antigen.

24. A pharmaceutical composition comprising:

(i) a binding protein as defined in claim 1; or (ii) a bispecific conjugate comprising a first binding protein and two second binding proteins attached to the first binding protein, wherein:

(a) the first binding protein is the binding protein of (i) and is an IgG2 antibody; and (b) the two second binding proteins are each a scFv which binds a peptide moiety, and each second binding protein is covalently linked to the C-terminal end of a heavy or light chain of the IgG2 antibody of (a); or (iii) a complex between the bispecific conjugate of (ii) and a tag construct comprising a peptide moiety covalently attached to an antigen, wherein the peptide moiety of said tag construct is non-covalently bound by each of said scFvs of (ii)(b); and at least one pharmaceutically acceptable carrier or excipient.

25. A method of treating or preventing cancer or an infection, comprising administering to a subject in need thereof a therapeutically effective amount of:

(i) a binding protein as defined in claim 1; or (ii) a bispecific conjugate and a tag construct, wherein the bispecific conjugate comprises a first binding protein and two second binding proteins attached to the first binding protein, wherein:

(a) the first binding protein is the binding protein of (i) and is an IgG2 antibody; and (b) the two second binding proteins are each a scFv which binds a peptide moiety, and each second binding protein is covalently linked to the C-terminal end of a heavy or light chain of the IgG2 antibody of (a);

and the tag construct comprises said peptide moiety covalently attached to a cancer antigen, wherein the bispecific conjugate and tag construct are administered to the same site simultaneously or within 1 hour of each other; or (iii) a complex between the bispecific conjugate and tag construct of (ii) wherein the peptide moiety of said tag construct is non-covalently bound by each of said scFvs of said conjugate.

* * * * *